US008188254B2

(12) United States Patent
Uhlmann et al.

(10) Patent No.: US 8,188,254 B2
(45) Date of Patent: May 29, 2012

(54) C-CLASS OLIGONUCLEOTIDE ANALOGS WITH ENHANCED IMMUNOSTIMULATORY POTENCY

(75) Inventors: Eugen Uhlmann, Glashuetten (DE); Jörg Vollmer, Duesseldorf (DE); Arthur M. Krieg, Wellesley, MA (US); Bernhard O. Noll, Neuss (DE)

(73) Assignees: Coley Pharmaceutical GmbH, Dusseldorf (DE); Coley Pharmaceutical Group, Inc., New York, NY (US)

( * ) Notice: Subject to any disclaimer, the term of this patent is extended or adjusted under 35 U.S.C. 154(b) by 926 days.

(21) Appl. No.: 10/978,283

(22) Filed: Oct. 29, 2004

(65) Prior Publication Data
US 2005/0239734 A1 Oct. 27, 2005

Related U.S. Application Data

(60) Provisional application No. 60/516,193, filed on Oct. 30, 2003.

(51) Int. Cl.
C07H 21/04 (2006.01)
(52) U.S. Cl. ........................................ 536/24.2; 514/44
(58) Field of Classification Search .................. None
See application file for complete search history.

(56) References Cited

U.S. PATENT DOCUMENTS

| | | |
|---|---|---|
| 4,806,463 A | 2/1989 | Goodchild et al. |
| 5,004,810 A | 4/1991 | Draper |
| 5,166,195 A | 11/1992 | Ecker |
| 5,194,428 A | 3/1993 | Agrawal et al. |
| 5,264,423 A | 11/1993 | Cohen et al. |
| 5,276,019 A | 1/1994 | Cohen et al. |
| 5,527,899 A | 6/1996 | Froehler |
| 5,646,126 A | 7/1997 | Cheng et al. |
| 5,663,153 A | 9/1997 | Hutcherson et al. |
| 5,696,248 A | 12/1997 | Peyman et al. |
| 5,723,335 A | 3/1998 | Hutcherson et al. |
| 5,856,462 A * | 1/1999 | Agrawal ................ 536/24.5 |
| 5,939,421 A | 8/1999 | Palanki et al. |
| 6,194,388 B1 | 2/2001 | Krieg et al. |
| 6,207,646 B1 | 3/2001 | Krieg et al. |
| 6,207,819 B1 | 3/2001 | Manoharan et al. |
| 6,214,806 B1 | 4/2001 | Krieg et al. |
| 6,218,371 B1 | 4/2001 | Krieg et al. |
| 6,221,882 B1 | 4/2001 | Macfarlane |
| 6,239,116 B1 | 5/2001 | Krieg et al. |
| 6,339,068 B1 | 1/2002 | Krieg et al. |
| 6,399,630 B1 | 6/2002 | Macfarlane |
| 6,406,705 B1 | 6/2002 | Davis et al. |
| 6,429,199 B1 | 8/2002 | Krieg et al. |
| 6,479,504 B1 | 11/2002 | Macfarlane et al. |
| 6,514,948 B1 | 2/2003 | Raz et al. |
| 6,521,637 B2 | 2/2003 | Macfarlane |
| 6,653,292 B1 | 11/2003 | Krieg et al. |
| 6,727,230 B1 | 4/2004 | Hutcherson et al. |
| 6,821,957 B2 | 11/2004 | Davis et al. |
| 6,943,240 B2 | 9/2005 | Bauer et al. |
| 6,949,520 B1 | 9/2005 | Hartmann et al. |
| 7,001,890 B1 | 2/2006 | Wagner et al. |
| 7,176,296 B2 | 2/2007 | Agrawal et al. |
| 7,223,741 B2 | 5/2007 | Krieg |
| 7,262,286 B2 | 8/2007 | Kandimalla et al. |
| 7,271,156 B2 | 9/2007 | Krieg et al. |
| 7,276,489 B2 | 10/2007 | Agrawal et al. |
| 7,354,711 B2 | 4/2008 | Macfarlane |
| 7,354,909 B2 | 4/2008 | Klinman et al. |
| 7,402,572 B2 | 7/2008 | Krieg et al. |
| 7,405,285 B2 | 7/2008 | Agrawal et al. |
| 7,407,944 B2 | 8/2008 | Agrawal et al. |
| 7,410,975 B2 | 8/2008 | Lipford et al. |
| 7,488,490 B2 | 2/2009 | Davis et al. |
| 7,517,861 B2 | 4/2009 | Krieg et al. |
| 7,521,063 B2 | 4/2009 | Klinman et al. |
| 7,524,828 B2 | 4/2009 | Krieg et al. |
| 7,534,772 B2 | 5/2009 | Weiner et al. |
| 7,566,703 B2 | 7/2009 | Krieg et al. |
| 7,569,553 B2 | 8/2009 | Krieg |
| 7,576,066 B2 | 8/2009 | Krieg |
| 7,585,847 B2 | 9/2009 | Bratzler et al. |
| 7,605,138 B2 | 10/2009 | Krieg |
| 7,615,539 B2 | 11/2009 | Krieg et al. |
| 7,674,777 B2 | 3/2010 | Krieg |

(Continued)

FOREIGN PATENT DOCUMENTS

CN 1468957 1/2004

(Continued)

OTHER PUBLICATIONS

Hartmann et al., Rational design of new CpG oligonucleotides that combine B cell activation with high IFN-a induction in plasmacytoid dendritic cells, 2003, European Journal of Immunology, vol. 33, pp. 1633-1641.*
Kandimalla et al., Secondary structures in CpG oligonucleotides affect immunostimulatory activity, 2003, Biochemical and Biophysical Research Communication, vol. 306, pp. 948-953.*
Stern et al., Vaccination with Tumor Peptide in CpG Adjuvant Protects Via IFN-g-Dependent CD4 Cell Immunity, 2002, The Journal of Immunology, vol. 168, pp. 6099-6105.*
Agrawal et al., Medicinal chemistry and therapeutic potential of CpG DNA. Trends Mol Med. Mar. 2002;8(3):114-21.
Agrawal et al., Pharmacokinetics of oligonucleotides. Ciba Found Symp. 1997;209:60-75; discussion 75-8.
Boggs et al., Characterization and modulation of immune stimulation by modified oligonucleotides. Antisense Nucleic Acid Drug Dev. Oct. 1997;7(5):461-71.

(Continued)

Primary Examiner — Benjamin P Blumel
(74) Attorney, Agent, or Firm — Wolf, Greenfield & Sacks, P.C.; Gregg C. Benson

(57) ABSTRACT

The invention relates to a class of CpG immunostimulatory oligonucleotides containing a CpG immunostimulatory motif and a second motif which is capable of forming secondary structure, including duplex and higher order structures, in vitro and in vivo. The oligonucleotides of the invention are useful as adjuvants in vaccination. The oligonucleotides are also useful for inducing an immune response, inducing expression of a type I interferon (IFN), inducing expression of gamma interferon (IFN-γ), and for treating a variety of conditions, including allergy, asthma, infection, and cancer.

50 Claims, 7 Drawing Sheets

U.S. PATENT DOCUMENTS

| | | |
|---|---|---|
| 7,713,529 B2 | 5/2010 | Krieg et al. |
| 7,723,022 B2 | 5/2010 | Krieg et al. |
| 7,723,500 B2 | 5/2010 | Krieg et al. |
| 7,776,344 B2 | 8/2010 | Hartmann et al. |
| 7,795,235 B2 | 9/2010 | Krieg et al. |
| 7,807,803 B2 | 10/2010 | Krieg et al. |
| 7,820,379 B2 | 10/2010 | Bauer et al. |
| 7,879,810 B2 | 2/2011 | Krieg et al. |
| 2001/0044416 A1 | 11/2001 | Davis et al. |
| 2002/0064515 A1 | 5/2002 | Krieg et al. |
| 2002/0091097 A1 | 7/2002 | Peterson et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0198165 A1 | 12/2002 | Bratzler et al. |
| 2003/0026782 A1 | 2/2003 | Krieg |
| 2003/0026801 A1 | 2/2003 | Weiner et al. |
| 2003/0032443 A1 | 2/2003 | Johnson et al. |
| 2003/0050261 A1 | 3/2003 | Krieg et al. |
| 2003/0050263 A1 | 3/2003 | Krieg et al. |
| 2003/0050268 A1 | 3/2003 | Krieg et al. |
| 2003/0055014 A1 | 3/2003 | Bratzler |
| 2003/0091599 A1 | 5/2003 | Davis et al. |
| 2003/0100527 A1 | 5/2003 | Krieg et al. |
| 2003/0104523 A1 | 6/2003 | Lipford et al. |
| 2003/0139364 A1 | 7/2003 | Krieg et al. |
| 2003/0148316 A1 | 8/2003 | Lipford et al. |
| 2003/0148976 A1 | 8/2003 | Krieg et al. |
| 2003/0166001 A1 | 9/2003 | Lipford |
| 2003/0175731 A1 | 9/2003 | Fearon et al. |
| 2003/0176389 A1 | 9/2003 | Raz et al. |
| 2003/0181406 A1 | 9/2003 | Schetter et al. |
| 2003/0191079 A1 | 10/2003 | Krieg et al. |
| 2003/0199466 A1 | 10/2003 | Fearon et al. |
| 2003/0212026 A1 | 11/2003 | Krieg et al. |
| 2003/0212029 A1 | 11/2003 | Agrawal et al. |
| 2003/0224010 A1 | 12/2003 | Davis et al. |
| 2003/0225016 A1 | 12/2003 | Fearon et al. |
| 2003/0232074 A1 | 12/2003 | Lipford et al. |
| 2003/0232443 A1 | 12/2003 | Bennett et al. |
| 2003/0232856 A1 | 12/2003 | Macfarlane |
| 2004/0006010 A1 | 1/2004 | Carson et al. |
| 2004/0009949 A1 | 1/2004 | Krieg |
| 2004/0030118 A1 | 2/2004 | Wagner et al. |
| 2004/0053880 A1 | 3/2004 | Krieg |
| 2004/0067902 A9 | 4/2004 | Bratzler et al. |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092468 A1 | 5/2004 | Schwartz |
| 2004/0092472 A1 | 5/2004 | Krieg |
| 2004/0097719 A1 | 5/2004 | Agrawal et al. |
| 2004/0106568 A1 | 6/2004 | Krieg et al. |
| 2004/0131628 A1 | 7/2004 | Bratzler et al. |
| 2004/0132677 A1 | 7/2004 | Fearon et al. |
| 2004/0132685 A1 | 7/2004 | Krieg et al. |
| 2004/0136948 A1 | 7/2004 | Fearon et al. |
| 2004/0142469 A1 | 7/2004 | Krieg et al. |
| 2004/0143112 A1 | 7/2004 | Krieg |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1* | 11/2004 | Davis et al. .................... 514/44 |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |
| 2005/0026861 A1 | 2/2005 | Kandimalla et al. |
| 2005/0032734 A1 | 2/2005 | Davis et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0130918 A1 | 6/2005 | Agrawal et al. |
| 2005/0148537 A1 | 7/2005 | Krieg et al. |
| 2005/0169888 A1 | 8/2005 | Hartmann et al. |
| 2005/0171047 A1 | 8/2005 | Krieg et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0209184 A1 | 9/2005 | Klinman et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250726 A1 | 11/2005 | Krieg et al. |
| 2005/0256073 A1 | 11/2005 | Lipford et al. |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1* | 1/2006 | Ahluwalia et al. ............... 514/44 |
| 2006/0019909 A1 | 1/2006 | Agrawal et al. |
| 2006/0019916 A1 | 1/2006 | Krieg et al. |
| 2006/0019918 A1 | 1/2006 | Agrawal et al. |
| 2006/0019923 A1 | 1/2006 | Davis et al. |
| 2006/0058251 A1 | 3/2006 | Krieg et al. |
| 2006/0089326 A1 | 4/2006 | Krieg et al. |
| 2006/0094680 A1 | 5/2006 | Agrawal et al. |
| 2006/0094681 A1 | 5/2006 | Agrawal et al. |
| 2006/0094683 A1 | 5/2006 | Krieg et al. |
| 2006/0140875 A1 | 6/2006 | Krieg et al. |
| 2006/0154890 A1 | 7/2006 | Bratzler et al. |
| 2006/0172966 A1 | 8/2006 | Lipford et al. |
| 2006/0188913 A1 | 8/2006 | Krieg et al. |
| 2006/0211639 A1 | 9/2006 | Bratzler et al. |
| 2006/0211644 A1 | 9/2006 | Krieg et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |
| 2006/0286070 A1 | 12/2006 | Hartmann et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1 | 2/2007 | Bratzler et al. |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0202128 A1 | 8/2007 | Krieg et al. |

| | | | |
|---|---|---|---|
| 2007/0202575 | A1 | 8/2007 | Klinman et al. |
| 2007/0224210 | A1 | 9/2007 | Krieg et al. |
| 2007/0232622 | A1 | 10/2007 | Lipford et al. |
| 2008/0009455 | A9 | 1/2008 | Krieg et al. |
| 2008/0026011 | A1 | 1/2008 | Krieg et al. |
| 2008/0031936 | A1 | 2/2008 | Krieg et al. |
| 2008/0045473 | A1 | 2/2008 | Uhlmann et al. |
| 2008/0113929 | A1 | 5/2008 | Lipford et al. |
| 2008/0152662 | A1 | 6/2008 | Agrawal et al. |
| 2008/0226649 | A1 | 9/2008 | Schetter et al. |
| 2009/0017021 | A1 | 1/2009 | Davis et al. |
| 2009/0060927 | A1 | 3/2009 | Wagner et al. |
| 2009/0117132 | A1 | 5/2009 | Readett et al. |
| 2009/0137519 | A1 | 5/2009 | Krieg et al. |
| 2009/0142362 | A1 | 6/2009 | Krieg et al. |
| 2009/0155212 | A1 | 6/2009 | Bratzler et al. |
| 2009/0155307 | A1 | 6/2009 | Davis et al. |
| 2009/0191188 | A1 | 7/2009 | Krieg et al. |
| 2009/0202575 | A1 | 8/2009 | Krieg et al. |
| 2009/0214578 | A1 | 8/2009 | Bauer |
| 2009/0306177 | A1 | 12/2009 | Uhlmann et al. |
| 2009/0311277 | A1 | 12/2009 | Krieg |
| 2010/0125101 | A1 | 5/2010 | Krieg et al. |
| 2010/0166780 | A1 | 7/2010 | Debelak et al. |
| 2010/0183639 | A1 | 7/2010 | Uhlmann et al. |
| 2010/0285041 | A1 | 11/2010 | Uhlmann et al. |

FOREIGN PATENT DOCUMENTS

| | | |
|---|---|---|
| EP | 0 468 520 A2 | 1/1992 |
| RU | 2185819 C1 | 7/2002 |
| WO | WO 94/01550 A1 | 1/1994 |
| WO | WO 94/08053 A1 | 4/1994 |
| WO | WO 98/11211 A2 | 3/1998 |
| WO | WO 98/29397 A1 | 7/1998 |
| WO | WO 98/49288 A1 | 11/1998 |
| WO | WO 99/56755 A1 | 11/1999 |
| WO | WO 00/06588 A1 | 2/2000 |
| WO | WO 00/14217 A2 | 3/2000 |
| WO | WO 00/15645 A1 | 3/2000 |
| WO | WO 00/67023 A1 | 11/2000 |
| WO | WO 01/12804 A2 | 2/2001 |
| WO | WO 01/22972 A2 | 4/2001 |
| WO | WO 01/55370 A3 | 8/2001 |
| WO | WO 01/83503 A2 | 11/2001 |
| WO | WO 01/85751 A1 | 11/2001 |
| WO | WO 02/32450 A2 | 4/2002 |
| WO | WO 02/053141 A2 | 7/2002 |
| WO | WO 02/069369 A2 * | 9/2002 |
| WO | WO 03/015711 A2 | 2/2003 |
| WO | WO 03/057822 A3 | 7/2003 |
| WO | WO 03/085110 A2 | 10/2003 |
| WO | WO 2004/007743 A2 | 1/2004 |
| WO | WO 2004/016805 A2 | 2/2004 |
| WO | WO 2004/026888 A2 | 4/2004 |
| WO | WO 2004/039829 A2 | 5/2004 |
| WO | WO 2004/058159 A2 | 7/2004 |
| WO | WO 2004/094671 A2 | 11/2004 |
| WO | WO 2008/030455 A2 | 3/2008 |
| WO | WO 2008/033432 A2 | 3/2008 |
| WO | WO 2008/039538 A2 | 4/2008 |
| WO | WO 2008/068638 A2 | 6/2008 |
| WO | WO 2008/139262 A2 | 11/2008 |

OTHER PUBLICATIONS

Garegg et al., Nucleoside H-phosphonates. III. Chemical synthesis of oligodeoxyribonucleotides by the hydrogenphosphonate approach. Tetrahedron Letts. 1986; 27(34):4051-4.
Garegg et al., Nucleoside H-phosphonates. IV. Automated solid phase synthesis of oligoribonucleotides by the hydrogenphosphonate approach. Tetrahedron Lett. 1986; 27(34):4055-8.
Hudson et al., Nucleic acid dendrimers: Novel biopolymer structures. J Am Chem Soc. 1993;115:2119-24.
Iho et al., Oligodeoxynucleotides containing palindrome sequences with internal 5'-CpG-3' act directly on human NK and activated T cells to induce IFN-gamma production in vitro. J Immunol. Oct. 1, 1999;163(7):3642-52.
Jäaschke et al., Automated incorporation of polyethylane glycol into synthetic oligonucleotides. Tetrahedron Lett. 1993;34(2):301-4.
Kandimalla et al., Effect of chemical modifications of cytosine and guanine in a CpG-motif of oligonucleotides: structure-immunostimulatory activity relationships. Bioorg Med Chem. Mar. 2001;9(3):807-13.
Kandimalla et al., Towards optimal design of second-generation immunomodulatory oligonucleotides. Curr Opin Mol Ther. Apr. 2002;4(2):122-9.
Kataoka et al., Antitumor activity of synthetic oligonucleotides with sequences from cDNA encoding proteins of *Mycobacterium bovis* BCG. Jpn J Cancer Res. Mar. 1992;83(3):244-7.
Kataoka et al., Immunotherapeutic potential in guinea-pig tumor model of deoxyribonucleic acid from *Mycobacterium bovis* BCG complexed with poly-L-lysine and carboxymethylcellulose. Jpn J Med Sci Biol. Oct. 1990;43(5):171-82.
Klinman et al., Immune recognition of foreign DNA: a cure for bioterrorism? Immunity. Aug. 1999;11(2):123-9.
Klinman et al., Immunotherapeutic uses of CpG oligodeoxynucleotides. Nat Rev Immunol. Apr. 2004;4(4):249-58.
Krieg et al., CpG motifs in bacterial DNA trigger direct B-cell activation. Nature. Apr. 6, 1995;374(6522):546-9.
Krieg, Immune effects and mechanisms of action of CpG motifs. Vaccine. Nov. 8, 2001;19(6):618-22.
Krieg, Now I know my CpGs. Trends Microbiol. Jun. 2001;9(6):249-52.
Kuramoto et al., Oligonucleotide sequences required for natural killer cell activation. Jpn J Cancer Res. Nov. 1992;83(11):1128-31.
Reitz et al., Small-molecule immunostimulants. Synthesis and activity of 7,8-disubstituted guanosines and structurally related compounds. J Med Chem. Oct. 14, 1994;37(21):3561-78.
Shchepinov et al., Oligonucleotide dendrimers: stable nano-structures. Nucleic Acids Res. Aug. 1, 1999;27(15):3035-41.
Tokunaga et al., Synthetic oligonucleotides with particular base sequences from the cDNA encoding proteins of *Mycobacterium bovis* BCG induce interferons and activate natural killer cells. Microbiol Immunol. 1992;36(1):55-66.
Uhlmann et al., Antisense oligonucleotides: a new therapeutic principle. Chem Rev. Jun. 1990;90(4):544-84.
Uhlmann et al., Recent advances in the development of immunostimulatory oligonucleotides. Curr Opin Drug Discov Devel. Mar. 2003;6(2):204-17.
Vollmer et al., Characterization of three CpG oligodeoxynucleotide classes with distinct immunostimulatory activities. Eur J Immunol. Jan. 2004;34(1):251-62.
Yamamoto et al., [Commemorative lecture of receiving Imamura Memorial Prize. II. Mode of action of oligonucleotide fraction extracted from *Mycobacterium bovis* BCG] Kekkaku. Sep. 1994;69(9):571-4.
Yamamoto et al., Lipofection of synthetic oligodeoxyribonucleotide having a palindromic sequence of AACGTT to murine splenocytes enhances interferon production and natural killer activity. Microbiol Immunol. 1994;38(10):831-6.
Yamamoto et al., Unique palindromic sequences in synthetic oligonucleotides are required to induce IFN [correction of INF] and augment IFN-mediated [correction of INF] natural killer activity. J Immunol. Jun. 15, 1992;148(12):4072-6.
Zhao et al., Effect of different chemically modified oligodeoxynucleotides on immune stimulation. Biochem Pharmacol. Jan. 26, 1996;51(2):173-82.
Press Release, Jan. 2007, "Coley Pharmaceutical Group Updates Hepatitis C Drug Development Strategy".
Press Release, Jun. 2007, "Coley Pharmaceutical Group Announces Pfizer's Discontinuation of Clinical Trials for PF-3512676 Combined with Cytotoxic Chemotherapy in Advanced Non Small Cell Lung Cancer".
Ahluwalia et al., Immunostimulatiory progiles from two classes of CpG ODN administered subcutaneously to healthy subjects. ICI FOCIS 2004.
Goldberg et al., Beyond danger: unmethylated CpG dinucleotides and the immunopathogenesis of disease. Immunol Lett. Jul. 3, 2000;73(1):13-8.

Gray et al., CpG-B ODNs potently induce low levels of IFN-alphabeta and induce IFN-alphabeta-dependent MHC-I cross-presentation in DCs as effectively as CpG-A and CpG-C ODNs. J Leukoc Biol. Apr. 2007;81(4):1075-85. Epub Jan. 16, 2007.

Krieg, Now I know my CpGs.Trends Microbiol. Jun. 2001;9(6):249-52.

Kyprianou, Doxazosin and terazosin suppress prostate growth by inducing apoptosis: clinical significance. J Urol. Apr. 2003;169(4):1520-5. Abstract Only.

Lee et al., Effects of a hexameric deoxyriboguanosine run conjugation into CpG oligodeoxynucleotides on their immunostimulatory potentials. J Immunol. Oct. 1, 2000;165(7):3631-9.

Mutwiri et al., Biological activity of immunostimulatory CpG DNA motifs in domestic animals. Vet Immunol Immunopathol. Jan. 30, 2003;91(2):89-103.

Norman et al., Liposome-mediated, nonviral gene transfer induces a systemic inflammatory response which can exacerbate pre-existing inflammation. Gene Ther. 2000;7:1425-30.

Rudginsky et al., Antitumor activity of cationic lipid complexed with immunostimulatory DNA. Mol Ther. Oct. 2001;4(4):347-55.

Scheule, The role of CpG motifs in immunostimulation and gene therapy. Adv Drug Deliv Rev. Nov. 15, 2000;44(2-3):119-34.

Storey et al., Anti-sense phosphorothioate oligonucleotides have both specific and non-specific effects on cells containing human papillomavirus type 16. Nucleic Acids Res. Aug. 11, 1991;19(15):4109-14.

Susten et al., Inhibition of dihydrofolate reductase, methotrexate transport, and growth of methotrexate-sensitive and -resistant L1210 leukemia cells in vitro by 5-substituted 2,4-diaminoquinazolines. Biochem Pharmacol. Jun. 15, 1985;34(12):2163-7. Abstract Only.

Vollmer et al., Impact of modifications of heterocyclic bases in CpG dinucleotides on their immune-modulatory activity. J Leukoc Biol. Sep. 2004;76(3):585-93. Epub Jun. 24, 2004.

Whitmore et al., LPD lipopolyplex initiates a potent cytokine response and inhibits tumor growth. Gene Ther. 1999;6:1867-75.

Whitmore et al., Systemic administration of LPD prepared with CpG oligonucleotides inhibits the growth of established pulmonary metastases by stimulating innate and acquired antitumor immune responses. Canc Immun Immunother. 2001;50:503-14.

Yamada et al., Effect of suppressive DNA on CpG-induced immune activation. J Immunol. Nov. 15, 2002;169(10):5590-4.

Yu et al., Potent CpG oligonucleotides containing phosphodiester linkages: in vitro and in vivo immunostimulatory properties. Biochem Biophys Res Commun. Sep. 13, 2002;297(1):83-90.

Zhang et al., Antisense oligonucleotide inhibition of hepatitis C virus (HCV) gene expression in livers of mice infected with an HCV-vaccinia virus recombinant. Antimicrob Agents Chemother. Feb. 1999;43(2):347-53.

Bhagat et al., CpG penta- and hexadeoxyribonucleotides as potent immunomodulatory agents. Biochem Biophys Res Commun. Jan. 24, 2003;300(4):853-61.

Lyer et al., Modified oligonucleotides—synthesis, properties and applications. Curr Opin Mol Ther. Jun. 1999;1(3):344-58. Review.

Marshall et al., Identification of a novel CpG DNA class and motif that optimally stimulate B cell and plasmacytoid dendritic cell functions.J Leukoc Biol. Jun. 2003;73(6):781-92.

Vollmer, J., TLR9 in health and disease. Int Rev Immunol. May-Aug. 2006;25(3-4):155-81. Review.

Wilson et al., Immune mechanisms and therapeutic potential of CpG oligodeoxynucleotides. Int Rev Immunol. May-Aug. 2006;25(3-4):183-213. Review.

Yu et al., 'Immunomers'—novel 3'-3'-linked CpG oligodeoxyribonucleotides as potent immunomodulatory agents. Nucleic Acids Res. Oct. 15, 2002;30(20):4460-9.

Agrawal, Importance of nucleotide sequence and chemical modifications of antisense oligonucleotides. Biochim Biophys Acta. Dec. 10, 1999;1489(1):53-68. Review.

Fathi et al., Oligonucleotides with novel, cationic backbone substituents: aminoethylphosphonates. Nucleic Acids Res. Dec. 11, 1999;22(24):5416-24.

Hanecak et al., Antisense oligonucleotide inhibition of hepatitis C virus gene expression in transformed hepatocytes. J Virol. Aug. 1996;70(8):5203-12.

Krieg et al., Identification of an oligodeoxynucleotide sequence motif that specifically inhibits phosphorylation by protein tyrosine kinases. Antisense Nucleic Acid Drug Dev. Apr. 1997;7(2):115-23.

Marshall et al., Superior activity of the type C class of ISS in vitro and in vivo across multiple species. DNA Cell Biol. Feb. 2005;24(2):63-72.

Samani et al., Best minimally modified antisense oligonucleotides according to cell nuclease activity. Antisense Nucleic Acid Drug Dev. Jun. 2001;11(3):129-36.

Uhlmann et al., Use of minimally modified antisense oligonucleotides for specific inhibition of gene expression. Methods Enzymol. 2000;313:268-84.

Uhlmann, Oligonucleotide technologies: synthesis, production, regulations and applications. Nov. 29-30, 2000, Hamburg, Germany. Expert Opin Biol Ther. Mar. 2001;1(2):319-28.

Vollmer et al., Identification of a new class of CpG oligonucleotides capable of inducing both B cell proliferation and high IFN-alpha secretion from PBMC of HCV chronic carriers. Antiv Ther. 2002;7:L115.

Wahlestedt et al., Potent and nontoxic antisense oligonucleotides containing locked nucleic acids. Proc Natl Acad Sci U S A. May 9, 2000;97(10):5633-8.

Yu et al., Immunostimulatory activity of CpG oligonucleotides containing non-ionic methylphosphonate linkages. Bioorg Med Chem. Nov. 2001;9(11):2803-8.

Fearon et al., A minimal human immunostimulatory CpG motif that potently induces IFN-Y and IFN-A production. Euro J of Immunology. 2003;33(8):2114-2122.

* cited by examiner

FIG. 7A
FIG. 7B
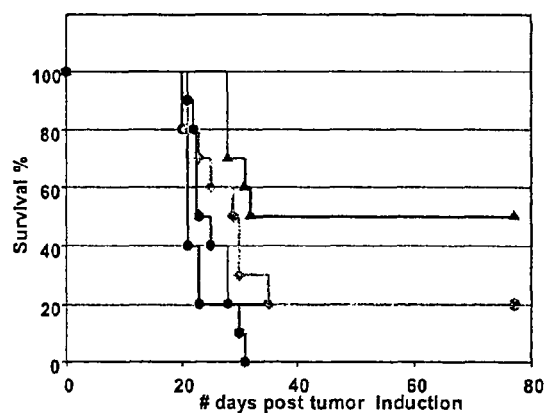
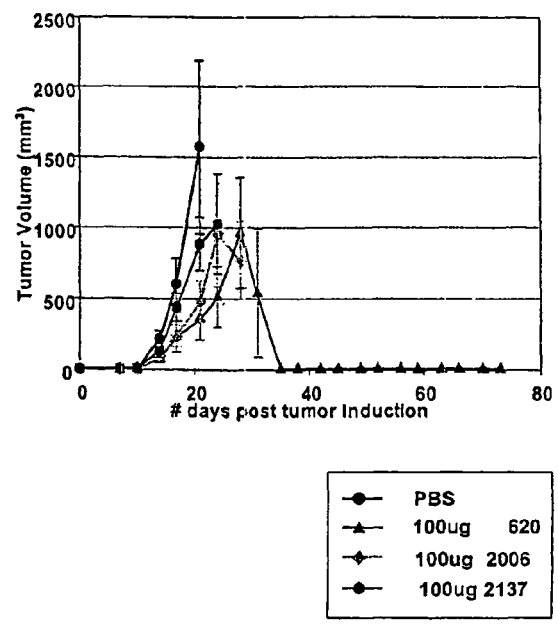

C-CLASS OLIGONUCLEOTIDE ANALOGS WITH ENHANCED IMMUNOSTIMULATORY POTENCY

RELATED APPLICATION

This application claims benefit under 35 U.S.C. 119 of U.S. Application Ser. No. 60/516,193, filed Oct. 30, 2003, the entire content of which is incorporated herein by reference.

FIELD OF THE INVENTION

The present invention relates generally to immunostimulatory nucleic acids, compositions thereof and methods of using the immunostimulatory nucleic acids.

BACKGROUND OF THE INVENTION

Bacterial DNA has immune stimulatory effects to activate B cells and natural killer cells, but vertebrate DNA does not. Tokunaga T et al. (1988) *Jpn J Cancer Res* 79:682-6; Tokunaga T et al. (1984) *JNCI* 72:955-62; Messina J P et al. (1991) *J Immunol* 147:1759-64; and reviewed in Krieg, 1998, In: Applied Oligonucleotide Technology, C. A. Stein and A. M. Krieg, (Eds.), John Wiley and Sons, Inc., New York, N.Y., pp. 431-448) and Krieg A M (2002) *Annu Rev Immunol* 20:709-60. It is now understood that these immune stimulatory effects of bacterial DNA are a result of the presence of unmethylated CpG dinucleotides in particular base contexts (CpG motifs), which are common in bacterial DNA, but methylated and underrepresented in vertebrate DNA. Krieg A M et al. (1995) *Nature* 374:546-9; Krieg A M (1999) *Biochim Biophys Acta* 1489:107-16.

The immune stimulatory effects of bacterial DNA can be mimicked with synthetic oligodeoxynucleotides (ODN) containing these CpG motifs. Such CpG ODN have highly stimulatory effects on human and murine leukocytes, inducing B-cell proliferation; cytokine and immunoglobulin secretion; natural killer (NK) cell lytic activity and interferon gamma (IFN-γ) secretion; and activation of dendritic cells (DCs) and other antigen-presenting cells to express costimulatory molecules and secrete cytokines, especially the Th1-like cytokines that are important in promoting the development of Th1-like T-cell responses. These immune stimulatory effects of native phosphodiester backbone CpG ODN are highly CpG-specific in that the effects are dramatically reduced if the CpG motif is methylated, changed to a GpC, or otherwise eliminated or altered. Krieg A M et al. (1995) *Nature* 374:546-9; Hartmann G et al. (1999) *Proc Natl. Acad Sci USA* 96:9305-10.

In early studies, it was thought that the immune stimulatory CpG motif followed the formula purine-purine-CpG-pyrimidine-pyrimidine. Krieg A M et al. (1995) *Nature* 374:546-9; Pisetsky D S (1996) *J Immunol* 156:421-3; Hacker H et al. (1998) *EMBO J* 17:6230-40; Lipford G B et al. (1998) *Trends Microbiol* 6:496-500. However, it is now clear that mouse lymphocytes respond quite well to phosphodiester CpG motifs that do not follow this "formula" (Yi A K et al. (1998) *J Immunol* 160:5898-906), and the same is true of human B cells and dendritic cells (Hartmann G et al. (1999) *Proc Natl Acad Sci USA* 96:9305-10; Liang H et al. (1996) *J Clin Invest* 98:1119-29).

SUMMARY OF THE INVENTION

The present invention relates in part to immunostimulatory CpG-containing oligonucleotides and oligonucleotide analogs having a secondary structure with an inverted repeat at or near the 3' end of the molecule. The secondary structure involves formation of duplex or higher-order structures under certain conditions. As an important feature of the oligonucleotides and oligonucleotide analogs of the invention, the inverted repeat is not a strict Watson-Crick palindrome but rather can be interrupted by intervening sequence or nucleotide analogs. As another feature of the oligonucleotides and oligonucleotide analogs of the invention, the backbone can be modified to include strategically placed nuclease-resistant and nuclease-sensitive internucleotide linkages, thereby both favoring activity and reducing potential toxicity. In addition, these oligonucleotides and oligonucleotide analogs are found to exert both A-class and B-class immunostimulatory activity and are therefore classified as novel C-class immunostimulatory nucleic acid molecules.

The invention is based, in part, on the discovery by the present inventors that CpG-containing immunostimulatory oligonucleotides and oligonucleotide analogs containing an imperfect palindrome at or near the 3' end of the molecule have certain advantages both in terms of their preparation and their biological activity. Specifically, the C-class oligonucleotides and oligonucleotide analogs of the instant invention are characteristically monomeric in solution. It is believed that these same nucleic acid molecules can form intramolecular duplex structures in vitro, rendering them stable against nuclease digestion. It is also believed that these same nucleic acid molecules can form intermolecular duplex and possibly even higher order structures within the environment of the intraendosomal compartment, where they are believed to exert their biological activity.

In one aspect the invention provides a composition including an immunostimulatory nucleic acid molecule of Formula I

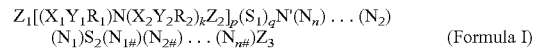

$$Z_1[(X_1Y_1R_1)N(X_2Y_2R_2)_kZ_2]_p(S_1)_qN'(N_n)\ldots(N_2)$$
$$(N_1)S_2(N_{1\#})(N_{2\#})\ldots(N_{n\#})Z_3 \quad \text{(Formula I)}$$

wherein each of $Z_1$, $Z_2$, and $Z_3$ is independently any sequence 0 to 12 nucleotides long which optionally includes a non-nucleotidic linker or abasic dSpacer; each of $X_1$ and $X_2$ is independently a nucleotide containing thymine, uracil, adenine, or a 5-substituted uracil; each of $Y_1$ and $Y_2$ is independently a cytosine (C) or a modified cytosine; each of $R_1$ and $R_2$ is independently a guanine (G) or a modified guanine; each of N and N' is independently any sequence 0 to 12 nucleotides long which optionally includes a non-nucleotidic linker or abasic dSpacer; $S_1$ is a non-nucleotidic linker, an abasic linker (dSpacers), triethylene glycol units or hexaethylene glycol units, which optionally provides for 2'5'-, 5'5'-, 3'3'-, 2'2'-, or 2'3'-internucleoside linkages; $S_2$ is any non-palindromic sequence 1 to 10 nucleotides long or a non-nucleotidic linker, an abasic linker (dSpacers), triethylene glycol units or hexaethylene glycol units; each of $N_1$, $N_2$, ... $N_n$, and $N_{1\#}$, $N_{2\#}$, ... $N_{n\#}$ is any nucleotide or modified nucleotide wherein $N_1$ base-pairs with $N_{1\#}$, $N_2$ base-pairs with $N_{2\#}$, ... and $N_n$ base-pairs with $N_{n\#}$; k is an integer from 0 to 5; n is an integer from 2 to 16; p is an integer from 1 to 6; and q is an integer from 0 to 10, and wherein when $(N_n)\ldots(N_2)(N_1) S_2 (N_{1\#})(N_{2\#})\ldots(N_{n\#})$ is 10 to 42 nucleotides long, $S_2$ is 4 to 10 nucleotides long, $S_2$ comprises a non-nucleotidic linker, an abasic linker (dSpacers), triethylene glycol units or hexaethylene glycol units, and/or $(N_n)\ldots(N_2)(N_1) S_2 (N_{1\#})(N_{2\#})\ldots(N_{n\#})$ has a GC content that is less than ⅔.

In one embodiment each of $N_1$, $N_2$, ... $N_n$, and $N_{1\#}$, $N_{2\#}$, ... $N_{n\#}$ is chosen from C, G, or modifications thereof, wherein C base-pairs with G.

In one embodiment each of $N_1, N_2, \ldots N_n$, and $N_{1\#}, N_{2\#}, \ldots N_{n\#}$ is chosen from T, A, or modifications thereof, and T base-pairs with A.

In these and other embodiments each of C, G, A, and T can refer to deoxynucleotides with corresponding bases cytosine, guanine, adenine, and thymine.

In one embodiment each of $N_1, N_2, \ldots N_n$, and $N_{1\#}, N_{2\#}, \ldots N_{n\#}$ is chosen from C, T, A, G, or modifications thereof, and C base-pairs with G, T base-pairs with G, A base-pairs with T, and A base-pairs with G.

In one embodiment each of $N_1, N_2, \ldots N_n$, and $N_{1\#}, N_{2\#}, \ldots N_{n\#}$ is chosen from unmodified or modified nucleotides which form Watson-Crick base pairs, i.e., each base pair $N_1$-$N_{1\#}$, $N_2$-$N_{2\#}$, $\ldots N_n$-$N_{n\#}$ is a Watson-Crick base pair.

In one embodiment at least one of each of $N_1, N_2, \ldots N_n$, and $N_{1\#}, N_{2\#}, \ldots N_{n\#}$ is chosen from unmodified or modified nucleotides which form non-Watson-Crick base pairs, i.e., at least one base pair $N_1$-$N_{1\#}$, $N_2$-$N_{2\#}$, $\ldots N_n$-$N_{n\#}$ is a non-Watson-Crick base pair.

In one embodiment the immunostimulatory nucleic acid molecule includes a partially stabilized backbone with at least one phosphodiester bond.

In one embodiment the immunostimulatory nucleic acid molecule includes a backbone with at least one stabilized internucleotide linkage.

In one embodiment internucleotide linkages of the oligonucleotide are all phosphorothioate linkages.

In one embodiment the immunostimulatory nucleic acid molecule includes a partially stabilized backbone with a phosphodiester bond joining at least one of $Y_1R_1$ or $Y_2R_2$.

In one embodiment $Y_1$ is C.

In one embodiment $R_1$ is G.

In one embodiment $Y_1$ is C and $R_1$ is G.

In one embodiment $X_1$ or $X_2$ is T.

In one embodiment $X_1$ is T, $X_2$ is T, $Y_1$ is C, $R_1$ is G, and k is 1.

In one embodiment $X_1$ is T, $X_2$ is T, $Y_1$ is C, $R_1$ is G, k is 1, p is 1, N and N' and $Z_3$ each contain zero nucleotides, and $Z_2$ is TTTT or d(UUUU), where d(UUUU) represents dUdUdUdU, i.e., $(deoxyU)_4$.

In one embodiment $S_2$ is a non-nucleotidic linker.

In one embodiment $S_2$ contains at least one abasic dSpacer residue.

In one embodiment the oligonucleotide includes at least one branched non-nucleoside linkage.

In one embodiment the immunostimulatory nucleic acid molecule includes at least one doubler unit, at least one trebler unit, or at least one doubler unit and at least one trebler unit.

In one embodiment $S_1$ is a doubler unit or a trebler unit.

In one embodiment the oligonucleotide includes at least one 2'5'-, 5'5'-, 3'3'-, 2'2'-, or 2'3'-internucleoside linkage.

In one embodiment the immunostimulatory nucleic acid molecule of Formula I is not an antisense nucleic acid.

In one aspect the invention provides an immunostimulatory nucleic acid molecule of Formula II

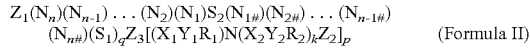

(Formula II)

wherein each of $Z_1$, $Z_2$, and $Z_3$ is independently any sequence 0 to 12 nucleotides long which optionally includes a non-nucleotidic linker or abasic dSpacer; each of $X_1$ and $X_2$ is independently a nucleotide containing thymine, uracil, adenine, or a 5-substituted uracil; each of $Y_1$ and $Y_2$ is independently a cytosine (C) or a modified cytosine; each of $R_1$ and $R_2$ is independently a guanine (G) or a modified guanine; N is any sequence 0 to 12 nucleotides long which optionally includes a non-nucleotidic linker or abasic dSpacer; $S_1$ is a non-nucleotidic linker, an abasic linker (dSpacers), triethylene glycol units or hexaethylene glycol units, which optionally provides for 2'5'-, 5'5'-, 3'3'-, 2'2'-, or 2'3'-internucleoside linkages; $S_2$ is any non-palindromic sequence 1 to 10 nucleotides long or a non-nucleotidic linker, an abasic linker (dSpacers), triethylene glycol units or hexaethylene glycol units; each of $N_1, N_2, \ldots N_{n-1}, N_n$, and $N_{1\#}, N_{2\#}, \ldots N_{n-1\#}, N_{n\#}$ is any nucleotide or modified nucleotide wherein $N_1$ base-pairs with $N_{1\#}$, $N_2$ base-pairs with $N_{2\#}$, $\ldots N_{n-1}$ base-pairs with $N_{n-1\#}$, and $N_n$ base-pairs with $N_{n\#}$; k is an integer from 0 to 5; n is an integer from 2 to 16; p is an integer from 1 to 6; and q is an integer from 0 to 10, and wherein when $(N_n) \ldots (N_2)(N_1) S_2 (N_{1\#})(N_{2\#}) \ldots (N_{n\#})$ is 10 to 42 nucleotides long, $S_2$ is 4 to 10 nucleotides long, $S_2$ comprises a non-nucleotidic linker, an abasic linker (dSpacers), triethylene glycol units or hexaethylene glycol units, and/or $(N_n) \ldots (N_2)(N_1) S_2 (N_{1\#})(N_{2\#}) \ldots (N_{n\#})$ has a GC content that is less than ⅔.

In one embodiment $Z_1 (N_n)(N_{n-1})$ is TYR, where Y is a cytosine or a modified cytosine and R is a guanine or a modified guanine.

In one embodiment each of $N_1, N_2, \ldots N_{n-1}, N_n$, and $N_{1\#}, N_{2\#}, \ldots N_{n-1\#}, N_{n\#}$ is chosen from C, G, or modifications thereof, wherein C base-pairs with G.

In one embodiment each of $N_1, N_2, \ldots N_{n-1}, N_n$, and $N_{1\#}, N_{2\#}, \ldots N_{n-1\#}, N_{n\#}$ is chosen from T, A, or modifications thereof, and T base-pairs with A.

In these and other embodiments each of C, G, A, and T can refer to deoxynucleotides with corresponding bases cytosine, guanine, adenine, and thymine.

In one embodiment each of $N_1, N_2, \ldots N_{n-1}, N_n$, and $N_{1\#}, N_{2\#}, \ldots N_{n-1\#}, N_{n\#}$ is chosen from C, T, A, G, or modifications thereof, and C base-pairs with G, T base-pairs with G, A base-pairs with T, and A base-pairs with G.

In one embodiment each of $N_1, N_2, \ldots N_{n-1}, N_n$, and $N_{1\#}, N_{2\#}, \ldots N_{n-1\#}, N_{n\#}$ is chosen from unmodified or modified nucleotides which form Watson-Crick base pairs, i.e., each base pair $N_1$-$N_{1\#}$, $N_2$-$N_{2\#}$, $\ldots N_n$-$N_{n\#}$ is a Watson-Crick base pair.

In one embodiment at least one of each of $N_1, N_2, \ldots N_{n-1}, N_n$, and $N_{1\#}, N_{2\#}, \ldots N_{n-1\#}, N_{n\#}$ is chosen from unmodified or modified nucleotides which form non-Watson-Crick base pairs, i.e., at least one base pair $N_1$-$N_{1\#}$, $N_2$-$N_{2\#}$, $\ldots N_n$-$N_{n\#}$ is a non-Watson-Crick base pair.

In one embodiment the immunostimulatory nucleic acid molecule includes a partially stabilized backbone with at least one phosphodiester bond.

In one embodiment the immunostimulatory nucleic acid molecule includes a backbone with at least one stabilized internucleotide linkage.

In one embodiment internucleotide linkages of the oligonucleotide are all phosphorothioate linkages.

In one embodiment the immunostimulatory nucleic acid molecule includes a partially stabilized backbone with a phosphodiester bond joining at least one of $Y_1R_1$ or $Y_2R_2$.

In one embodiment $Y_1$ is C.

In one embodiment $R_1$ is G.

In one embodiment $Y_1$ is C and $R_1$ is G.

In one embodiment $X_1$ or $X_2$ is T.

In one embodiment $X_1$ is T, $X_2$ is T, $Y_1$ is C, $R_1$ is G, and k is 1.

In one embodiment $X_1$ is T, $X_2$ is T, $Y_1$ is C, $R_1$ is G, k is 1, p is 1, N and N' and $Z_3$ each contain zero nucleotides, and $Z_2$ is TTTT or d(UUUU), where d(UUUU) represents $(deoxyU)_4$.

In one embodiment $S_2$ is a non-nucleotidic linker.

In one embodiment $S_2$ contains at least one abasic dSpacer residue.

In one embodiment the oligonucleotide includes at least one branched non-nucleoside linkage.

In one embodiment the immunostimulatory nucleic acid molecule includes at least one doubler unit, at least one trebler unit, or at least one doubler unit and at least one trebler unit.

In one embodiment $S_1$ is a doubler unit or a trebler unit.

In one embodiment the oligonucleotide includes at least one 2'5'-, 5'5'-, 3'3'-, 2'2'-, or 2'3'-internucleoside linkage.

In one embodiment the immunostimulatory nucleic acid molecule of Formula I is not an antisense nucleic acid.

In one aspect the invention provides an immunostimulatory nucleic acid molecule of Formula III $$(Z')_m Z_3 (S_3) \quad \text{(Formula III)}$$

wherein Z' is $Z_1 [(X_1 Y_1 R_1) N (X_2 Y_2 R_2)_k Z_2]_p (S_1)_q$ N' $(N_n) \ldots (N_3)(N_2)(N_1) S_2 (N_{1\#})(N_{2\#})(N_{3\#}) \ldots (N_{n\#})$; each of $Z_1$, $Z_2$, and $Z_3$ is independently any sequence 0 to 12 nucleotides long which optionally includes a non-nucleotidic linker or abasic dSpacer; each of $X_1$ and $X_2$ is independently a nucleotide containing thymine, uracil, adenine, or a 5-substituted uracil; each of $Y_1$ and $Y_2$ is independently a cytosine or a modified cytosine; each of $R_1$ and $R_2$ is independently a guanine or a modified guanine; each of N and N' is independently any sequence 0 to 12 nucleotides long which optionally includes a non-nucleotidic linker or abasic dSpacer; $S_1$ is a non-nucleotidic linker, an abasic linker (dSpacers), triethylene glycol units or hexaethylene glycol units, which optionally provides for 2'5'-, 5'5'-, 3'3'-, 2'2'-, or 2'3'-internucleoside linkages; $S_2$ is any non-palindromic sequence 1 to 10 nucleotides long or a non-nucleotidic linker, an abasic linker (dSpacers), triethylene glycol units or hexaethylene glycol units; $S_3$ is a direct or indirect 2'5'-, 5'5'-, 3'3'-, 2'2'-, or 2'3'-internucleoside linkage, or a non-nucleotidic linker, said non-nucleotidic linker including abasic linkers (dSpacers), triethylene glycol units, or hexaethylene glycol units facilitating a 2'5'-, 5'5'-, 3'3'-, 2'2'-, or 2'3'-linkage of m sequence parts; each of $N_1, N_2, \ldots N_n$, and $N_{1\#}, N_{2\#}, \ldots N_{n\#}$ is any nucleotide or modified nucleotide wherein $N_1$ base-pairs with $N_{1\#}$, $N_2$ base-pairs with $N_{2\#}$, $N_3$ base-pairs with $N_{3\#}$, ... and $N_n$ base-pairs with $N_{n\#}$; k is an integer from 0 to 5; m is an integer from 2 to 10; n is an integer from 2 to 16; p is an integer from 1 to 6; and q is an integer from 0 to 10.

In certain embodiments $Z_1 [(X_1 Y_1 R_1) N (X_2 Y_2 R_2)_k Z_2]_p (S_1)_q$ is a non-palindromic sequence.

In certain embodiments $Z_1 [(X_1 Y_1 R_1) N (X_2 Y_2 R_2)_k Z_2]_p (S_1)_q$ is TCGTCGTTTT (SEQ ID NO:40), TCGTCGTTLL, TCGA, TCGAC, TCGACGTC, or TCGACGTCG, wherein L is dSpacer.

In certain embodiments $Z_1 [(X_1 Y_1 R_1) N (X_2 Y_2 R_2)_k Z_2]_p (S_1)_q$ is a palindromic sequence.

In certain embodiments $Z_1 [(X_1 Y_1 R_1) N (X_2 Y_2 R_2)_k Z_2]_p (S_1)_q$ is TCGACGTCGA (SEQ ID NO:19) or TCGTCGACGA (SEQ ID NO:34).

In certain embodiments $Z_1 [(X_1 Y_1 R_1) N (X_2 Y_2 R_2)_k Z_2]_p (S_1)_q$ is TCGCGACGTT (SEQ ID NO:26) or TCGCGTCGTT (SEQ ID NO:69).

In one embodiment $(N_n) \ldots (N_2)(N_1) S_2 (N_{1\#})(N_{2\#}) \ldots (N_{n\#}) Z_3$ includes a sequence AGCGAAGCT, CAATATTTATTG (SEQ ID NO:1), CCGTTTTGTGG (SEQ ID NO:2), CGGCGCCGTGCCG (SEQ ID NO:19), CGGCGCCGTGCCG (SEQ ID NO:34), CGGCGLLCGCCG (SEQ ID NO:5), CGGCGLLLTGCCG (SEQ ID NO:6), CGGCGLLCCGCCG (SEQ ID NO:7), CGGCGTCGCCGCCG (SEQ ID NO:8), CGTCGACGGGACGGG (SEQ ID NO:10), CGTCGACGTGACGGG (SEQ ID NO:11), GAGAGTTGGGCTCTC (SEQ ID NO:12), GTCGAGGAGGT (SEQ ID NO:14), TAATALLTATTA (SEQ ID NO: 15), TAATATC-CATTA (SEQ ID NO: 16), or TAATATTTATTA (SEQ ID NO: 17), wherein L is dSpacer.

In one embodiment $(N_n) \ldots (N_2)(N_1) S_2 (N_{1\#})(N_{2\#}) \ldots (N_{n\#})$ includes a sequence GGCGCGCTGCCG (SEQ ID NO:13).

In one embodiment the immunostimulatory nucleic acid molecule includes a sequence

| | |
|---|---|
| TCGACGTCGACCGTTTTGTGG, | (SEQ ID NO:20) |
| TCGACGTCGACGGGACGGG, | (SEQ ID NO:21) |
| TCGACGTCGACGTGACGGG, | (SEQ ID NO:22) |
| TCGACGTCGAGAGTTGGGCTCTC, | (SEQ ID NO:23) |
| TCGACGTCGAGCGAAGCT, or | (SEQ ID NO:24) |
| TCGACGTCGAGGAGGT. | (SEQ ID NO:25) |

In one embodiment the immunostimulatory nucleic acid molecule includes a sequence

| | |
|---|---|
| TCGTCGTTLLACGGCGCCGTGCCG, | (SEQ ID NO:37) |
| TCGTCGTTLLACGGCGLLLTGCCG, | (SEQ ID NO:38) |
| TCGTCGTTLLCGGCGCGGCGCCG, | (SEQ ID NO:39) |
| TCGTCGTTTTACGGCGCCGTTGCCG, | (SEQ ID NO:44) |
| TCGTCGTTTTACGGCGLLLTGCCG, | (SEQ ID NO:45) |
| TCGTCGTTTTACGGCGTTTTGCCG, | (SEQ ID NO:49) |
| TCGTCGTTTTCAATATTTATTG, | (SEQ ID NO:50) |
| TCGTCGTTTTCGGCGLLCGCCG, | (SEQ ID NO:52) |
| TCGTCGTTTTCGGCGGLLCCGCCG, | (SEQ ID NO:54) |
| TCGTCGTTTTCGGCGTCGCCGCCG, | (SEQ ID NO:55) |
| TCGTCGTTTTTAATALLTATTA, | (SEQ ID NO:57) |
| TCGTCGTTTTTAATATCCATTA, or | (SEQ ID NO:58) |
| TCGTCGTTTTTAATATTTTATTA, | (SEQ ID NO:59) | wherein L is dSpacer.

In one embodiment the immunostimulatory nucleic acid molecule includes a sequence TCGCGTCGTTCG-GCGCGCTGCCG (SEQ ID NO:30).

In one embodiment the immunostimulatory nucleic acid molecule includes a sequence TCGCGACGTTCG-GCGCGCTGCCG (SEQ ID NO:27).

In one embodiment the immunostimulatory nucleic acid molecule includes a sequence chosen from

| | |
|---|---|
| | (SEQ ID NO:43) |
| T*C*G*T*C*G*T*T*T*T*A*C_G*G*C_G*C*C_G*T*G*C*C*G, | |
| | (SEQ ID NO:43) |
| T*C*G*T*C_G*T*T*T*T*A*C_G*G*C*G*C*C_G*T*G*C*C*G, | |
| | (SEQ ID NO:42) |
| T*C*G*T*C*G*T*T*T*T*A*C*G*A*C*G*C*C*G*T*G*C*C*G, | |
| | (SEQ ID NO:36) |
| T*C*G*T*C*G*C*T*T*T*G*C*G*A*C*G*C*C*G*T*G*C*C*G, | |

-continued

T*C*G*T*C*G*C*C*C*G*G*C*G*A*C*G*C*C*G*T*G*C*C*G, (SEQ ID NO:35)

T*C*G*T*C*G*T*T*T*A*C*G*G*C*G*C*C*G*T*T*G*C*C*G, (SEQ ID NO:44)

T*C*G*T*C*G*T*L*L*A*C*G*G*C*G*C*C*G*T*G*C*C*G, (SEQ ID NO:37)

T*C*G*T*C*G*T*T*T*T*A*C*G*G*C*G*L*L*L*T*G*C*C*G, (SEQ ID NO:45)

T*C*G*T*C*G*T*T*L*L*A*C*G*G*C*G*L*L*L*T*G*C*C*G, (SEQ ID NO:38)

T*C*G*T*C*G*T*T*T*T*C*G*G*C*G*G*L*L*C*C*G*C*C*G, (SEQ ID NO:54)

T*C*G*T*C*G*T*T*T*T*C*G*G*C*G*T*C*G*C*C*G*C*C*G, (SEQ ID NO:55)

T*C*G*T*C*G*T*T*L*L*C*G*G*C*G*C*G*G*C*G*C*C*G, (SEQ ID NO:39)

T*C*G*T*C*G*T*T*T*T*C*G*G*C*G*L*L*C*G*C*C*G, (SEQ ID NO:52)

T*C*G*T*C*G*T*T*T*T*T*A*A*T*A*T*T*T*A*T*T*A, (SEQ ID NO:59)

T*C*G*T*C_G*T*T*T*T*T*A*A*T*A*T*T*T*A*T*T*A, (SEQ ID NO:59)

T*C*G*T*C_G*T*T*T*T*C*A*A*T*A*T*T*T*A*T*T*G, (SEQ ID NO:50)

T*C*G*T*C_G*T*T*T*T*T*A*A*T*A*T*C*C*A*T*T*A, (SEQ ID NO:58)

T*C*G*T*C*G*T*T*T*T*T*A*A*T*A*L*L*T*A*T*T*A, (SEQ ID NO:57)

T*C*G*T*C_G*T*T*T*T*A*C*G*G*C*G*L*L*L*T*G*C*C*G, (SEQ ID NO:45)

T*C*G*T*C_G*T*T*L*L*A*C*G*G*C*G*L*L*L*T*G*C*C*G, and (SEQ ID NO:38)

T*C*G*T*C_G*T*T*T*T*C*G*G*C*G*G*L*L*C*C*G*C*C*G, (SEQ ID NO:54)

wherein L is dSpacer, * is phosphorothioate, and _ is phosphodiester.

In one embodiment the immunostimulatory nucleic acid molecule includes a sequence chosen from

T*C*G*A*C*G*T*C*G_A_C*G*G*G*A*C*G*G*G, (SEQ ID NO:21)

T*C*G*A*C*G*T*C*G_A_C*G*T*G*A*C*G*G*G, (SEQ ID NO:22)

T*C*G*A*C*G*T*C*G*A*C*G*G*G*A*C*G*G*G, (SEQ ID NO:21)

T*C*G*A*C*G*T*C*G*A*G*G*A*G*G*T, (SEQ ID NO:25)

T*C*G*A*C*G*T*C*G*A*G*C*G*A*A*G*C*T, (SEQ ID NO:24)

T*C*G*A*C*G*T*C*G*A*C*C*G*T*T*T*G*T*G*G, and (SEQ ID NO:20)

T*C*G*A*C*G*T*C*G*A*G*A*G*T*T*G*G*C*T*C*T*C, (SEQ ID NO:23)

wherein * is phosphorothioate and _ is phosphodiester.

In one embodiment the immunostimulatory nucleic acid molecule includes a sequence chosen from

T*C*G*A*C*G*T*C*G*A*C*G*T*G*A*C*G*T*G, (SEQ ID NO:62)

T*C*G*A*C*G*T*C*G*A*C*G*T*G*A*C*G, (SEQ ID NO:61)

T*C_G*T*C_G*A*C_G*T*T*C_G*G*C*G*C*C_G*T*G*C*C*G, (SEQ ID NO:65)

T*C*G*T*C_G*T*A*C_G*G*C*G*C*C_G*T*G*C*C*G, (SEQ ID NO:66)

T*C*G*T*C_G*T*T*A*C_G*G*C*G*C*C_G*T*G*C*C*G, (SEQ ID NO:67)

T*C*G*A*C*G*T*C*G*A*C*G*T*G*A*C*G*T*T, (SEQ ID NO:63)

T*C*G*T*C_G*A*C_G*A*T*C_G*G*C*G*C*C_G*T*G*C*C*G, (SEQ ID NO:64)

T*C*G*T*C*G*A*C*G*A_T_C*G*G*C*G*C*C*G*T*G*C*C*G, (SEQ ID NO:64)

T*C*G*A*C_G*T*C*G*A*C_G*T*G*A*C*G*T*T, (SEQ ID NO:63)

T*C*G*A*C_G*T*C*G*A*C*G*T_G*A*C*G*T*T, and (SEQ ID NO:63)

T*C*G*T*C_G*T*T*T*A*C_G*G*C*G*C*C_G*T*G*C*C*G*T, (SEQ ID NO:68)

wherein * is phosphorothioate and _ is phosphodiester.

In one embodiment the immunostimulatory nucleic acid molecule includes a sequence chosen from

T*C*G*C_G*T*C*G*T*T*C_G*G*C*G*C_G*C*T*G*C*C*G, (SEQ ID NO:30)

T*C*G_C*G*T*C*G*T*T*C_G*G*C*G*C_G*C*T*G*C*C*G, and (SEQ ID NO:30)

T*C*G*C*G_T*C*G*T*T*C_G*G*C*G*C_G*C*T*G*C*C*G, (SEQ ID NO:30)

wherein * is phosphorothioate and _ is phosphodiester.

In one embodiment the immunostimulatory nucleic acid molecule includes a sequence T*C*G*C_G*A*C*G*T*T*C_G*G*C*G*C_G*C*T*G*C*C*G (SEQ ID NO:27), wherein * is phosphorothioate and _ is phosphodiester.

In one embodiment the immunostimulatory nucleic acid molecule includes a sequence chosen from T*C_G*T*C*G*T*T*T*T*A*C*G*G*C*G*T*C*G*T*G*C*C*G (SEQ ID NO:48), T*C_G*T*C*G*T*T*T*T*A*C*G*G*C*G*T*C*G*C*G*C*C*G (SEQ ID NO:47), and T*C_G*T*C*G*T*T*T*T*A*C*G*G*C*G*T*C*G*C*C*G (SEQ ID NO:46), wherein * is phosphorothioate and_ is phosphodiester.

In one embodiment the immunostimulatory nucleic acid molecule includes a sequence T*C_G*T*C*G*T*T*T*T*A* C*G*G*C*G*T*C*G*T*G*C*C*G (SEQ ID NO:48), wherein * is phosphorothioate and _ is phosphodiester.

In one embodiment the immunostimulatory nucleic acid molecule includes a sequence T*C_G*G*C*G*C*C_G*T*G*C*C*G*T*C*G*T*C_G*T*T*T (SEQ ID NO:33), wherein * is phosphorothioate and _is phosphodiester.

In one embodiment at least one nucleotide in the oligonucleotide is a substituted or modified purine or pyrimidine.

In one embodiment the substituted pyrimidine is a C5- or C6-substituted pyrimidine.

In one embodiment the substituted purine is a C8- or C7-substituted purine.

In one embodiment the substituted or modified purine or pyrimidine is selected from the group consisting of 5-substituted cytosines, 6-substituted cytosines, N4-substituted cytosines, 5-aza-cytosine, 2-mercapto-cytosine, isocytosine, pseudo-isocytosine, cytosine analogs with condensed ring systems, and uracil derivatives, thymine derivatives, 7-deaza-guanine, 7-deaza-7-substituted guanine, 7-deaza-8-substituted guanine, 7-deaza-8-aza guanine, hypoxanthine, N2-substituted guanines, 5-amino-3-methyl-3H,6H-thiazolo[4,5-d]pyrimidine-2,7-dione, 2,6-diaminopurine, 2-aminopurine, purine, indole, substituted adenines, 8-substituted guanine, and 6-thioguanine.

In one embodiment the substituted or modified purine or pyrimidine is selected from the group consisting of 5-methyl-cytosine, 5-fluoro-cytosine, 5-chloro-cytosine, 5-bromo-cytosine, 5-iodo-cytosine, 5-hydroxy-cytosine, 6-hydroxy-cytosine, 5-hydroxymethyl-cytosine, 5-difluoromethyl-cytosine, and unsubstituted or substituted 5-alkynyl-cytosine, N4-ethyl-cytosine, N,N'-propylene cytosine, phenoxazine, 5-fluoro-uracil, 5-bromo-uracil, 5-bromovinyl-uracil, 4-thio-uracil, 5-hydroxy-uracil, 5-propynyl-uracil, 2-thiothymine, 4-thiothymine, 6-substituted thymines, 7-deaza-7-(C2-C6) alkynylguanine, N2-methyl-guanine, N6-methyl-adenine, 8-oxo-adenine, 8-hydroxyguanine, and 8-bromoguanine.

In one embodiment the substituted or modified purine or pyrimidine is selected from the group consisting of a universal base, an aromatic ring system, an aromatic ring system, and a hydrogen atom (dSpacer).

In one embodiment the substituted or modified purine or pyrimidine is selected from the group consisting of 4-methyl-indole, 5-nitro-indole, 3-nitropyrrole, P-base, and K-base, benzimidazole, dichloro-benzimidazole, 1-methyl- 1 H-[1,2,4]triazole-3-carboxylic acid amide, fluorobenzene, and difluorobenzene.

In one embodiment any of N, S, X, or Z is substituted by a residue selected from the group consisting of C6-C30 alkyl chain, bile acids, cholic acid, taurocholic acid, deoxycholate, cholesterol, oleyl litocholic acid, oleoyl cholenic acid, glycolipids, phospholipids, sphingolipids, isoprenoids, steroids, vitamins, vitamin E, saturated fatty acids, unsaturated fatty acids, fatty acid esters, triglycerides, pyrenes, porphyrins, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes, cyanine dye Cy3, cyanine dye Cy576, Hoechst 33258 dye, psoralen, and ibuprofen.

In one aspect the invention provides an immunostimulatory nucleic acid molecule including (a) a 5' end beginning with an immunostimulatory motif chosen from (TCG)$_n$N and RDCGY$_1$Y$_2$N, wherein T is thymine, C is unmethylated cytosine, G is guanine, R is a purine, D is not C, each of Y$_1$ and Y$_2$ independently is a pyrimidine, n is an integer between 1 and 4, inclusive, and N is any sequence 0-12 bases long; (b) a 3' end terminating in an inverted repeat capable of forming a hairpin or stem-loop structure, said structure including a GC-rich stem 2 to 6 consecutive base pairs long and at least one unmatched or mismatched base; and (c) a partially stabilized backbone including at least one phosphodiester 5'-CpG-3' linkage. Either or both of C and G in the CpG dinucleotide may be modified.

In one embodiment the GC-rich stem is 2 consecutive base pairs long.

In one embodiment the GC-rich stem is 3 consecutive base pairs long.

In one embodiment the GC-rich stem is 4 consecutive base pairs long.

In one embodiment the GC-rich stem is 5 consecutive base pairs long.

In one embodiment the GC-rich stem is 6 consecutive base pairs long.

In one embodiment the GC-rich stem includes at least 2 G-C base pairs.

In one embodiment the GC-rich stem includes at least 3 G-C base pairs.

In certain embodiments the at least one unmatched or mismatched base is T.

In one embodiment the partially stabilized backbone including at least one phosphodiester 5'-CpG-3' linkage further includes a plurality of phosphorothioate internucleotide linkages.

In one embodiment the 5' end has a sequence provided as TCGTCGTTTTA (SEQ ID NO:41).

In one embodiment the 3' end terminating in an inverted repeat has a base sequence provided as CGGCGCCGTGCCG (SEQ ID NO:19).

In one embodiment the 3' end terminating in an inverted repeat has a base sequence provided as CGGCGTCGTGCCG (SEQ ID NO:9).

In one aspect the invention provides an immunostimulatory nucleic acid having a base sequence provided as TCGTCGTTTTACGGCGCCGTGCCG (SEQ ID NO:43).

In one aspect the invention provides an immunostimulatory nucleic acid having a base sequence provided as TCGTCGTTTTACGGCGTCGTGCCG (SEQ ID NO:48).

In one aspect the invention provides an immunostimulatory nucleic acid having a base sequence provided as T*C_G*T*C*G*T*T*T*T*A*C*G*G*C*G*C*C*G* T*G*C*C*G (SEQ ID NO:43), wherein * represents phosphorothioate internucleotide linkage and _represents phosphodiester internucleotide linkage.

In one aspect the invention provides an immunostimulatory nucleic acid having a base sequence provided as T*C*G*T*C*G*T*T*T*T*A*C_G*G*C_G*C*C_G*T* G*C*C*G (SEQ ID NO:43), wherein * represents phosphorothioate internucleotide linkage and _represents phosphodiester internucleotide linkage.

In one aspect the invention provides an immunostimulatory nucleic acid having a base sequence provided as T*C*G*T*C*G*T*T*T*T*A*C_G*G*C*G*C*C_G*T* G*C*C*G (SEQ ID NO:43), wherein * represents phosphorothioate internucleotide linkage and _represents phosphodiester internucleotide linkage.

In one aspect the invention provides an immunostimulatory nucleic acid having a base sequence provided as T*C*G*T*C_G*T*T*T*T*A*C_G*G*C*G*C*C_G*T* G*C*C*G (SEQ ID NO:43), wherein * represents phosphorothioate internucleotide linkage and _represents phosphodiester internucleotide linkage.

In one aspect the invention provides a vaccine including an immunostimulatory nucleic acid molecule of the invention and an antigen.

In one aspect the invention provides a pharmaceutical composition including an immunostimulatory nucleic acid molecule of the invention and a pharmaceutically acceptable carrier.

In one aspect the invention provides a method for inducing type I interferon (IFN) expression. The method according to this aspect of the invention involves contacting a cell capable of expressing type I IFN with an immunostimulatory nucleic acid of the invention, in an effective amount to induce expression of type I IFN.

In one embodiment the type I IFN is an interferon alpha (IFN-α).

In one embodiment the type I IFN is an interferon beta (IFN-β).

In one aspect the invention provides a method for inducing gamma interferon (IFN-γ) expression. The method according to this aspect of the invention involves contacting a cell capable of expressing IFN-γ with an immunostimulatory nucleic acid of the invention, in an effective amount to induce expression of IFN-γ.

In one aspect the invention provides a method for activating a natural killer (NK) cell. The method according to this aspect of the invention involves contacting an NK cell with an immunostimulatory nucleic acid of the invention, in an effective amount to activate the NK cell.

In one aspect the invention provides a method for treating an infection. The method according to this aspect of the invention involves administering to a subject having or at risk of developing an infection an immunostimulatory nucleic acid of the invention, in an effective amount to treat or prevent the infection.

In one embodiment the subject has or is at risk of developing an infection chosen from a viral, bacterial, fungal or parasitic infection.

In one embodiment the subject has or is at risk of developing a viral infection with a virus chosen from hepatitis B virus (HBV), hepatitis C virus (HCV), cytomegalovirus (CMV), Epstein-Barr virus (EBV), papillomavirus, human immunodeficiency virus (HIV), or herpes simplex virus (HSV).

In one embodiment the subject has or is at risk of developing a bacterial infection with a species of bacterium chosen from *Leishmania, Listeria*, or *Anthrax*.

In one aspect the invention provides a method for treating an allergic condition. The method according to this aspect of the invention involves administering to a subject having or at risk of developing an allergic condition an immunostimulatory nucleic acid of the invention, in an effective amount to treat or prevent the allergic condition.

In one embodiment the allergic condition is allergic asthma.

In one aspect the invention provides a method for treating cancer. The method according to this aspect of the invention involves administering to a subject having or at risk of developing a cancer an immunostimulatory nucleic acid of the invention, in an effective amount to treat or prevent the cancer.

In one embodiment the cancer is chosen from basal cell carcinoma, biliary tract cancer, bladder cancer, bone cancer, brain and central nervous system cancer, breast cancer, cervical cancer, choriocarcinoma, colon and rectum cancer, connective tissue cancer, cancer of the digestive system, endometrial cancer, esophageal cancer, eye cancer, cancer of the head and neck, gastric cancer, intra-epithelial neoplasm, kidney cancer, larynx cancer, leukemia, liver cancer, lung cancer, lymphoma including Hodgkin's and non-Hodgkin's lymphoma, melanoma, myeloma, neuroblastoma, oral cavity cancer, ovarian cancer, pancreatic cancer, prostate cancer, retinoblastoma, rhabdomyosarcoma, rectal cancer, renal cancer, cancer of the respiratory system, sarcoma, skin cancer, stomach cancer, testicular cancer, thyroid cancer, uterine cancer, cancer of the urinary system, or other carcinomas and sarcomas.

In one embodiment the cancer is a cancer sensitive to treatment with interferon alpha (IFN-α).

In one embodiment the cancer sensitive to treatment with IFN-α is chosen from hairy cell leukemia, chronic myelogenous leukemia, cutaneous T-cell leukemia, multiple myeloma, follicular lymphoma, malignant melanoma, squamous cell carcinoma, AIDS-related Kaposi's sarcoma, renal cell carcinoma, prostate carcinoma, cervical dysplasia, or colon carcinoma.

In one aspect the invention provides use of an immunostimulatory nucleic acid of the invention for manufacture of a medicament for use in treatment of an infection.

In one aspect the invention provides use of an immunostimulatory nucleic acid of the invention for manufacture of a medicament for use in treatment of an allergic condition.

In one aspect the invention provides use of an immunostimulatory nucleic acid of the invention for manufacture of a medicament for use in treatment of allergic asthma.

In one aspect the invention provides use of an immunostimulatory nucleic acid of the invention for manufacture of a medicament for use in treatment of a cancer.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

The present invention may be more easily and completely understood when taken in conjunction with the accompanying figures. The figures are provided for illustrative purposes only and are not required for understanding or practicing the invention.

FIG. 7A is a graph depicting survival according to different ODN treatments in a euroblastoma tumor model.

FIG. 7B is a graph depicting tumor volume according to different ODN treatments in neuroblastoma tumor model.

TABLE OF SELECTED SEQUENCES

Figure 1:
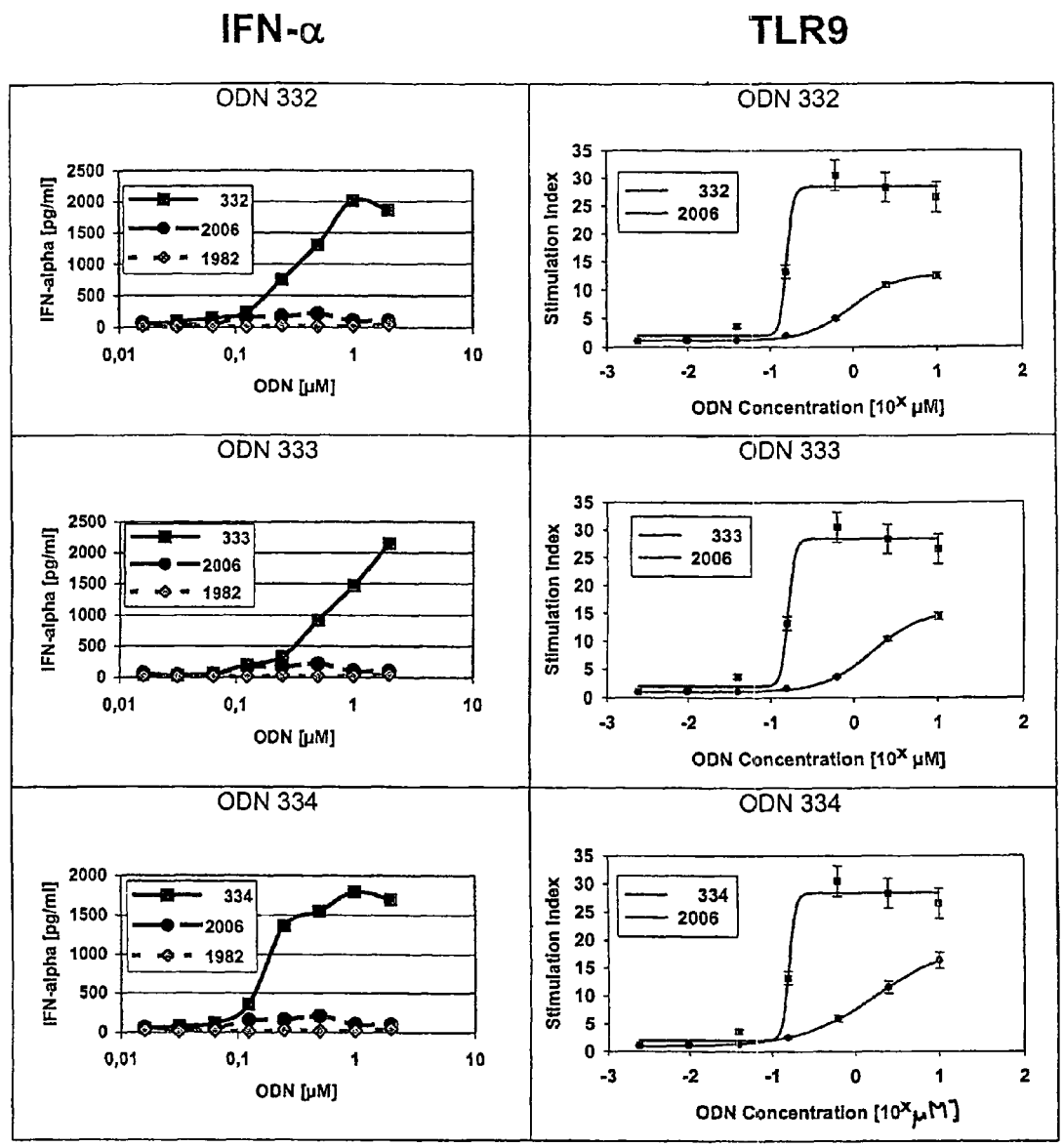
FIG. 1 is a series of graphs depicting induction of IFN-α and TLR9 signaling by ODN 332, 333, and 334.

| ODN | Sequence | SEQ ID NO: |
|---|---|---|
| 126 | T*C_G*T*C*G*T*T*T*T*A*C*G*G*C*G*T*C*G*C*G*C*C*G | 47 |
| 128 | T*C_G*T*C*G*T*T*T*T*A*C*G*G*C*G*T*C*G*T*G*C*C*G | 48 |
| 129 | T*C_G*T*C*G*T*T*T*T*A*C*G*G*C*G*C*C*G*T*G*C*C*G | 43 |
| 130 | T*C_G*T*C*G*T*T*T*T*A*C*G*G*C*G*T*C*G*C*G | 46 |
| 286 | T*C*G*A*C*G*T*C*G_A_C*G*T*G*A*C*G*G | 22 |
| 291 | T*C*G*A*C*G*T*C*G*A*C*G*G*G*A*C*G*G | 21 |
| 298 | T*C*G*T*C*G*T*T*T*T*A*C*G*A*C*G*C*C*G*T*G*C*C*G | 42 |
| 299 | T*C*G*T*C*G*C*T*T*T*G*C*G*A*C*G*C*C*G*T*G*C*C*G | 36 |
| 300 | T*C*G*T*C*G*C*C*C*G*G*C*G*A*C*G*C*C*G*T*G*C*C*G | 35 |
| 301 | T*C*G*T*C*G*T*T*T*T*A*C*G*G*C*G*C*C*G*T*T*G*C*C*G | 44 |
| 306 | T*C*G*T*C*G*T*T*L*L*A*C*G*G*C*G*C*C*G*T*G*C*C*G | 37 |
| 307 | T*C*G*T*C*G*T*T*T*T*A*C*G*G*C*G*L*L*L*T*G*C*C*G | 45 |
| 308 | T*C*G*T*C*G*T*T*L*L*A*C*G*G*C*G*L*L*L*T*G*C*C*G | 38 |
| 310 | T*C*G*T*C*G*T*T*T*T*C*G*G*C*G*G*L*L*C*C*G*C*C*G | 54 |
| 312 | T*C*G*T*C*G*T*T*T*T*C*G*G*C*G*T*C*G*C*C*G*C*C*G | 55 |
| 313 | T*C*G*T*C*G*T*T*L*L*C*G*G*C*G*C*G*G*C*G*C*C*G | 39 |
| 314 | T*C*G*T*C*G*T*T*T*T*C*G*G*C*G*L*L*C*G*C*C*G | 52 |
| 331 | T*C*G*C_G*A*C*G*T*T*C_G*G*C*G*C_G*C*T*G*C*C*G | 27 |
| 332 | T*C*G*C_G*T*C*G*T*T*C_G*G*C*G*C_G*C*T*G*C*C*G | 30 |
| 333 | T*C*G*C_G*A*C*G*T*T*C_G*G*C*G*C_G*T*C*G*C*C*G | 28 |
| 334 | T*C*G*C_G*A*C*G*T*T*C_G*G*C*G*G*C_T*C*G*C*C*G | 29 |
| 335 | T*C*G_C*G*T*C*G*T*T*C_G*G*C*G*C_G*C*T*G*C*C*G | 30 |
| 336 | T*C*G*C*G_T*C*G*T*T*C_G*G*C*G*C_G*C*T*G*C*C*G | 30 |
| 337 | T*C*G*C*G_A*C*G*T*T*C_G*G*C*G*C_G*T*C*G*C*C*G | 28 |
| 338 | T*C*G*C*G_A*C*G*T*T*C_G*G*C*G*G*C_T*C*G*C*C*G | 29 |
| 339 | T*C*G_C*G*A*C*G*T*T*C_G*G*C*G*C_G*T*C*G*C*C*G | 28 |
| 340 | T*C*G_C*G*A*C*G*T*T*C_G*G*C*G*G*C_T*C*G*C*C*G | 29 |
| 341 | T*C*G*C_G*T*C*G*T*T*C_G*G*C*G*C_G*T*C*G*C*C*G | 31 |
| 342 | T*C*G*C_G*T*C*G*T*T*C_G*G*C*G*G*C_T*C*G*C*C*G | 32 |
| 343 | T*C*G*C*G_T*C*G*T*T*C_G*G*C*G*C_G*T*C*G*C*C*G | 31 |
| 344 | T*C*G*C*G_T*C*G*T*T*C_G*G*C*G*G*C_T*C*G*C*C*G | 32 |
| 380 | T*C*G*A*C*G*T*C*G*A*G*G*A*G*G*G*T | 25 |
| 382 | T*C*G*A*C*G*T*C*G*A*G*C*G*A*A*G*C*T | 24 |
| 383 | T*C*G*A*C*G*T*C*G*A*C*C*G*T*T*T*T*G*T*G*G | 20 |
| 384 | T*C*G*A*C*G*T*C*G*A*G*A*G*T*T*G*G*C*T*C*T*C | 23 |
| 608 | T*C*G*T*C_G*T*T*T*T*C_G*G*C_G*C*G*C_G*C*C*G | 51 |
| 611 | T*C*G*T*C*G*T*T*T*T*A*C_G*G*C_G*C*C_G*T*G*C*C*G | 43 |
| 614 | T*C*G*T*C*G*T*T*T*T*A*C_G*G*C*G*C*C_G*T*G*C*C*G | 43 |

TABLE OF SELECTED SEQUENCES-continued

| ODN | Sequence | SEQ ID NO: |
|---|---|---|
| 618 | T*C*G*T*C_G*T*T*T*T*C_G*G*C*G*G*C*C_G*C*C*G | 53 |
| 620 | T*C*G*T*C_G*T*T*T*T*A*C_G*G*C*G*C*C_G*T*G*C*C*G | 43 |
| 644 | T*C*G*T*C*G*T*T*T*T*T*A*A*T*A*T*T*T*A*T*T*A | 59 |
| 645 | T*C*G*T*C_G*T*T*T*T*T*A*A*T*A*T*T*T*A*T*T*A | 59 |
| 646 | T*C*G*T*C_G*T*T*T*T*C*A*A*T*A*T*T*T*A*T*T*G | 50 |
| 647 | T*C*G*T*C_G*T*T*T*T*T*A*A*T*A*T*C*C*A*T*T*A | 58 |
| 648 | T*C*G*T*C*G*T*T*T*T*T*A*A*T*A*L*L*T*A*T*T*A | 57 |
| 649 | T*C*G*T*C_G*T*T*T*T*A*C*G*G*C*G*L*L*T*G*C*C*G | 45 |
| 650 | T*C*G*T*C_G*T*T*L*L*A*C*G*G*C*G*L*L*T*G*C*C*G | 38 |
| 651 | T*C*G*T*C_G*T*T*T*T*C*G*G*C*G*G*L*L*C*C*G*C*C*G | 54 |
| 830 | T*C*G*A*C*G*T*C*G_A_C*G*G*G*A*C*G*G*G | 21 |

DETAILED DESCRIPTION OF THE INVENTION

The invention in one aspect involves the finding that specific sub-classes of CpG immunostimulatory oligonucleotides having defined secondary structure are highly effective in mediating immune stimulatory effects. These CpG nucleic acids are useful therapeutically and prohylactically for stimulating the immune system to treat cancer, infectious diseases, allergy, asthma and other disorders and to help protect against opportunistic infections following cancer chemotherapy. The strong yet balanced cellular and humoral immune responses that result from CpG stimulation reflect the body's own natural defense system against invading pathogens and cancerous cells.

The sequences of the invention share some structural similarities with a class of CpG oligonucleotides referred to as C-class or combination motif CpG oligonucleotides. See published PCT international patent application WO 03/015711. Similar to the previously described C-class oligonucleotides, the C-class CpG oligonucleotides of the instant invention have defined 5' and 3' motifs as parts of the molecule. These previously described C-class oligonucleotides have both a traditional "stimulatory" CpG sequence, generally positioned at or near the 5' end or 3' end of the molecule, and a "GC-rich palindrome" motif, generally positioned at or near the other end of the molecule. These combination motif nucleic acids have immune stimulating effects that fall somewhere between those effects associated with traditional "B-class" CpG ODN, which are strong inducers of B cell activation and dendritic cell activation, and those effects associated with a more recently described class of immune stimulatory nucleic acids ("A-class" CpG ODN) which are strong inducers of IFN-α and NK cell activation but relatively poor inducers of B-cell and DC activation.

The new C-class CpG oligonucleotides of the instant invention are also structurally distinct from the previously described C-class CpG oligonucleotides. In comparison to the previously described C-class CpG oligonucleotides, the immunostimulatory nucleic acid molecules of the instant invention feature greatly relaxed requirements with respect to the GC-rich palindrome at one end of the molecule. For example, the previously described C-class oligonucleotides include in one embodiment a strict or perfect palindrome at least 10 nucleotides in length and having a GC content of at least ⅔. In some embodiments the palindrome of the previously described C-class oligonucleotides can include at most a minimal number of consecutive mismatched nucleotides.

In contrast to the previously described C-class oligonucleotides, the C-class oligonucleotide analogs of the instant invention feature palindromic motifs that can have, in various embodiments, fewer than 10 nucleotides; a GC content between zero and less than ⅔; various nucleotide analogs and substitutes including those lacking any nucleobase (dSpacer); extended intervening sequence involving four or more consecutive nucleotides or nucleotide substitutes that do not form Watson-Crick base pairs; and any combination thereof. Furthermore, in some embodiments 3' parts of two or more molecules can be linked together via their 3' ends. It has been discovered that this new sub-class of oligonucleotides which do not have a perfect palindrome are still capable, like the previously described combination motif CpG oligonucleotides, of inducing high levels of IFN production, including type I IFN (e.g., IFN-α, IFN-β) and IFN-γ.

A "palindrome" and, equivalently, "palindromic sequence" as used herein refers to a nucleic acid sequence which is its own perfect reverse complement (i.e., a sequence such as ABCDEE'D'C'B'A' in which A and A', B and B', C and C', D and D', and E and E' are bases capable of forming the usual Watson-Crick base pairs, i.e., G-C, A-T, and A-U. As used herein, a "palindrome" in a strict sense excludes intervening sequence or intervening non-nucleotide structure that does not participate in forming the usual Watson-Crick base pairs.

An "inverted repeat" as used herein refers to an imperfect palindrome, i.e., a nucleic acid sequence in which are present both nucleotides capable of forming the usual Watson-Crick base pairs and nucleotides, nucleotide analogs, or other structures that do not participate in forming the usual Watson-Crick base pairs (e.g., a sequence such as ABCDE-S-E'D'C'B'A' in which A and A', B and B', C and C', D and D', and E and E' are bases capable of forming the usual Watson-Crick base pairs, and S is a non-palindromic sequence or a non-nucleotidic linker or an abasic linker (dSpacer)). In certain embodiments the nucleotides, nucleotide analogs, or other structures that do not participate in forming the usual Watson-Crick base pairs interrupt an otherwise perfect palindrome. In certain embodiments the nucleotides that do not participate in forming the usual Watson-Crick base pairs can form non-Watson-Crick base pairs with another nucleotide, e.g., G-T. A non-Watson-Crick base pair as used herein is any base pair other than a Watson-Crick base pair, including but not limited to a Hoogsteen base pair and a so-called wobble base pair. In certain embodiments the nucleotides that do not participate in forming the usual Watson-Crick base pairs are unmatched and have no nucleotide base or nucleotide base analog with which to form a Watson-Crick or non-Watson-Crick base pair, e.g., G opposite to dSpacer. In certain embodiments the nucleotides that do not participate in forming base pairs can form non-standard base pairs with another nucleotide, e.g., diaminopyridine can form a base pair with xanthosine.

In one embodiment the 5' end of the nucleic acid begins with an immunostimulatory motif chosen from $(TCG)_nN$ and $RDCGY_1Y_2N$. T is thymine, C is unmethylated cytosine, G is guanine, R is a purine, D is not C, each of $Y_1$ and $Y_2$ independently is a pyrimidine, n is an integer between 1 and 4, inclusive, and N is any sequence 0-12 bases long.

The 3' end of the nucleic acid terminates in an inverted repeat capable of forming a hairpin or stem-loop structure. The term "terminates" refers to a structure at or near the 3'end. Thus, the end of the imperfect palindrome may be positioned at the actual 3' end of the molecule or alternatively the 3' end may include 1 or more additional nucleotides that are not part of the inverted repeat structure. Preferably the 3' end of the molecule includes 3 or fewer nucleotides that do not form part of the inverted repeat structure.

In one embodiment an "inverted repeat capable of forming a hairpin or stem-loop structure" as used herein refers to a sequence of nucleotides that forms a GC-rich stem or hairpin that is 2 to 10 consecutive base pairs long, and includes at least one unmatched or mismatched base. In individual embodiments the GC-rich stem is 2, 3, 4, 5, 6, 7, 8, 9, or 10 consecutive base pairs long. In some embodiments the GC-rich stem includes at least 2, 3, or 4 G-C base pairs.

In one embodiment an "inverted repeat capable of forming a hairpin or stem-loop structure" as used hererin refers to a sequence of nucleotides that forms an AT-rich stem or hairpin that is 2 to 10 consecutive base pairs long, and includes at least one unmatched or mismatched base. In individual embodiments the AT-rich stem is 2, 3, 4, 5, 6, 7, 8, 9, or 10 consecutive base pairs long. In some embodiments the AT-rich stem includes at least 2, 3, or 4 A-T base pairs.

In some instances the at least one unmatched or mismatched base bridges the ends of the stem or hairpin. This may allow the formation of the secondary structure by providing a flexible point in the molecule for the stems to base pair and form a hairpin. Alternatively the unmatched or mismatched base(s) may be within the stem. Preferably if the mismatched base is within the stem, then the stem is at least 3 base pairs long. The unmatched or mismatched bases(s) may be any nucleotide. In some embodiments the unmatched or mismatched base is a T. Unmatched nucleotides at the end of double-strands are also known as overhanging nucleotides or dangling ends which can significantly stabilize duplex formation or hairpin formation. Freier SM et al. (1983) Effects of 3' dangling end stacking on the stability of GGCC and CCGG double helixes. *Biochemistry* 22:6198-206.

The nucleic acid also includes a partially stabilized backbone including at least one phosphodiester 5'-CpG-3' linkage.

In some instances the double-stranded part of the molecule may also contain unnatural (non-standard) base pairs (e.g., diaminopyridine paired with xanthosine). Lutz M J et al. (1998) Recognition of a non-standard base pair by thermostable DNA polymerases. *Bioorg Med Chem Lett* 8:1149-52.

The formulas define subsets of the class of CpG oligonucleotides which demonstrated excellent immune stimulating properties. In the formulas 5' refers to the free 5' end of the oligonucleotide and 3' refers to the free 3' end of the oligonucleotide.

The oligonucleotides may have one or more accessible 5' or 3' ends. In some embodiments a 3' end can be linked to another 3' end. Since the importance of the 5' and 3'motifs has been discovered and described herein, it is also possible to create modified oligonucleotides having two such 5' or 3' ends. This may be achieved, for example, by attaching two oligonucleotides through a 3'-3' linkage to generate an oligonucleotide having two accessible 5' ends. The 3'3'- or 5'5'-linkage may be a phosphodiester, phosphorothioate, or any other modified internucleoside bridge. Methods for accomplishing such linkages are known in the art. For instance, such linkages have been described in Seliger H et al. (1991) Oligonucleotide analogs with terminal 3'-3'- and 5'-5'-internucleotidic linkages as antisense inhibitors of viral gene expression, *Nucleosides & Nucleotides* 10:469-77 and Jiang Z et al. (1999) Pseudo-cyclic oligonucleotides: in vitro and in vivo properties, *Bioorg Med Chem* 7:2727-35.

Additionally, 3'-3'-linked or 5'-5'-linked ODNs where the linkage between the 3'- or 5'-terminal nucleosides is not a phosphodiester, phosphorothioate or other modified bridge, can be prepared using an additional spacer, such as tri- or tetra-ethyleneglycol phosphate moiety (Durand M et al. (1992) Triple-helix formation by an oligonucleotide containing one (dA)12 and two (dT)12 sequences bridged by two hexaethylene glycol chains, *Biochemistry* 31:9197-204; U.S. Pat. Nos. 5,658,738; and 5,668,265). Alternatively, the non-nucleotidic linker may be derived from ethanediol, propanediol, or from an abasic deoxyribose (dSpacer) unit (Fontanel M L et al. (1994) Sterical recognition by T4 polynucleotide kinase of non-nucleosidic moieties 5'-attached to oligonucleotides, *Nucleic Acids Res* 22:2022-7) using standard phosphoramidite chemistry. The non-nucleotidic linkers can be incorporated once or multiple times, or combined with each other allowing for any desirable distance between the 3' ends of the two ODNs to be linked.

A "non-nucleotidic linker" as used herein refers to any linker element that is not a nucleotide or polymer thereof (i.e., a polynucleotide), wherein a nucleotide includes a purine or pyrimidine nucleobase and a sugar phosphate. A non-nucleotidic linker thus includes an abasic nucleotide (dSpacer), i.e., a nucleotide-like sugar phosphate unit in which the nucleobase is replaced by a hydrogen atom. A non-nucleotidic linker can be a polyethyleneglycol, including but not limited to a triethyleneglcol and a hexaethyleneglycol.

In some embodiments the oligonucleotide has one of the following structures:

TCGTCGTTTTA, (SEQ ID NO:41)

CGGCGCCGTGCCG, (SEQ ID NO:19)

CGGCGTCGTGCCG, (SEQ ID NO:9)

TCGTCGTTTTACGGCGCCGTGCCG, (SEQ ID NO:43)

TCGTCGTTTTACGGCGTCGTGCCG, (SEQ ID NO:48)

-continued (SEQ ID NO:43)
T*C_G*T*C*G*T*T*T*A*C*G*G*C*G*C*C*G*T*G*C*C*G, (SEQ ID NO:43)
T*C*G*T*C*G*T*T*T*A*C_G*G*C_G*C*C_G*T*G*C*C*G, (SEQ ID NO:43)
T*C*G*T*C*G*T*T*T*A*C_G*G*C*G*C*C_G*T*G*C*C*G,
and (SEQ ID NO:43)
T*C*G*T*C_G*T*T*T*A*C_G*G*C*G*C*C_G*T*G*C*C*G.

The symbol * refers to the presence of a stabilized intemucleotide linkage and _ refers to the presence of a phosphodiester linkage.

The immunostimulatory oligonucleotides generally have a length in the range of between 6 and 100 nucleotides. In some embodiments the length is in the range of 6-40, 13-100, 13-40, 13-30, 15-50, or 15-30 nucleotides or any integer range therebetween.

The terms "nucleic acid" and "oligonucleotide" are used interchangeably to mean multiple nucleotides (i.e., molecules including a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G)). As used herein, the terms "nucleic acid" and "oligonucleotide" refer to oligoribonucleotides as well as oligodeoxyribonucleotides. The terms "nucleic acid" and "oligonucleotide" shall also include polynucleosides (i.e., a polynucleotide minus the phosphate) and any other organic base containing polymer. Nucleic acid molecules can be obtained from existing nucleic acid sources (e.g., genomic or cDNA), but are preferably synthetic (e.g., produced by nucleic acid synthesis).

The terms "nucleic acid" and "oligonucleotide" as used herein shall encompass nucleic acid molecules and oligonucleotides of the invention, as well as oligonucleotide analogs of the invention. The terms "oligodeoxynucleotide" and, equivalaently, "ODN" as used herein shall encompass unmodified oligodeoxynucleotides of the invention as well as oligodeoxynucleotide analogs of the invention.

The terms "nucleic acid" and "oligonucleotide" also encompass nucleic acids or oligonucleotides with substitutions or modifications, such as in the bases and/or sugars. For example, they include nucleic acids having backbone sugars that are covalently attached to low molecular weight organic groups other than a hydroxyl group at the 2' position and other than a phosphate group or hydroxy group at the 5' position. Thus modified nucleic acids may include a 2'-O-alkylated ribose group. In addition, modified nucleic acids may include sugars such as arabinose or 2'-fluoroarabinose instead of ribose. Thus the nucleic acids may be heterogeneous in backbone composition thereby containing any possible combination of polymer units linked together such as peptide-nucleic acids (which have a peptide-like backbone with nucleic acid bases). Other examples are described in more detail below.

The immunostimulatory oligonucleotides of the instant invention can encompass various chemical modifications and substitutions, in comparison to natural RNA and DNA, involving a phosphodiester intemucleoside bridge, a β-D-ribose unit and/or a natural nucleoside base (adenine, guanine, cytosine, thymine, uracil). Examples of chemical modifications are known to the skilled person and are described, for example, in Uhlmann E et al. (1990) Chem Rev 90:543; "Protocols for Oligonucleotides and Analogs" Synthesis and Properties & Synthesis and Analytical Techniques, S. Agrawal, Ed, Humana Press, Totowa, USA 1993; Crooke S T et al. (1996) Annu Rev Pharmacol Toxicol 36:107-29; and Hunziker J et al. (1995) Mod Synth Methods 7:331-417. An oligonucleotide according to the invention may have one or more modifications, wherein each modification is located at a particular phosphodiester intemucleoside bridge and/or at a particular β-D-ribose unit and/or at a particular natural nucleoside base position in comparison to an oligonucleotide of the same sequence which is composed of natural DNA or RNA.

For example, the oligonucleotides may include one or more modifications and wherein each modification is independently selected from:
a) the replacement of a phosphodiester intemucleoside bridge located at the 3' and/or the 5' end of a nucleoside by a modified intemucleoside bridge,
b) the replacement of phosphodiester bridge located at the 3' and/or the 5' end of a nucleoside by a dephospho bridge,
c) the replacement of a sugar phosphate unit from the sugar phosphate backbone by another unit,
d) the replacement of a β-D-ribose unit by a modified sugar unit, and
e) the replacement of a natural nucleoside base by a modified nucleoside base.

More detailed examples for the chemical modification of an oligonucleotide are as follows.

The oligonucleotides may include modified intemucleotide linkages, such as those described in a or b above. These modified linkages may be partially resistant to degradation (e.g., are stabilized). A "stabilized oligonucleotide molecule" shall mean an oligonucleotide that is relatively resistant to in vivo degradation (e.g., via an exo- or endo-nuclease) resulting form such modifications. Oligonucleotides having phosphorothioate linkages, in some embodiments, may provide maximal activity and protect the oligonucleotide from degradation by intracellular exo- and endo-nucleases.

A phosphodiester intemucleoside bridge located at the 3' and/or the 5' end of a nucleoside can be replaced by a modified intemucleoside bridge, wherein the modified intemucleoside bridge is for example selected from phosphorothioate, phosphorodithioate, $NR^1R^2$-phosphoramidate, boranophosphate, α-hydroxybenzyl phosphonate, phosphate-$(C_1$-$C_{21})$-O-alkyl ester, phosphate-[$(C_6$-$C_{12})$aryl-$(C_1$-$C_{21})$-O-alkyl]ester, $(C_1$-$C_8)$alkylphosphonate and/or $(C_6$-$C_{12})$arylphosphonate bridges, $(C_7$-$C_{12})$-α-hydroxymethyl-aryl (e.g., disclosed in WO 95/01363), wherein $(C_6$-$C_{12})$aryl, $(C_6$-$C_{20})$aryl and $(C_6$-$C_{14})$aryl are optionally substituted by halogen, alkyl, alkoxy, nitro, cyano, and where $R^1$ and $R^2$ are, independently of each other, hydrogen, $(C_1$-$C_{18})$-alkyl, $(C_6$-$C_{20})$-aryl, $(C_6$-$C_{14})$-aryl-$(C_1$-$C_8)$-alkyl, preferably hydrogen, $(C_1$-$C_8)$-alkyl, preferably $(C_1$-$C_4)$-alkyl and/or methoxyethyl, or $R^1$ and $R^2$ form, together with the nitrogen atom carrying them, a 5-6-membered heterocyclic ring which can additionally contain a further heteroatom from the group O, S and N.

The replacement of a phosphodiester bridge located at the 3' and/or the 5' end of a nucleoside by a dephospho bridge (dephospho bridges are described, for example, in Uhlmann E and Peyman A in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethyl-hydrazo, dimethylenesulfone and/or silyl groups.

A sugar phosphate unit (i.e., a β-D-ribose and phosphodiester intemucleoside bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak EP et al. (1989) *Nucleic Acids Res* 17:6129-41), that is, e.g., the replacement by a morpholino-derivative unit; or to build up a polyamide nucleic acid ("PNA"; as described for example, in Nielsen PE et al. (1994) *Bioconjug Chem* 5:3-7), that is, e.g., the replacement by a PNA backbone unit, e.g., by 2-aminoethylglycine. The oligonucleotide may have other carbohydrate backbone modifications and replacements, such as peptide nucleic acids with phosphate groups (PHONA), locked nucleic acids (LNA), and oligonucleotides having backbone sections with alkyl linkers or amino linkers. The alkyl linker may be branched or unbranched, substituted or unsubstituted, and chirally pure or a racemic mixture.

A β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, 2'-F-arabinose, 2'-O-($C_1$-$C_6$)alkyl-ribose, preferably 2'-O-($C_1$-$C_6$) alkyl-ribose is 2'-O-methylribose, 2'-O-($C_2$-$C_6$)alkenyl-ribose, 2'-[O-($C_1$-$C_6$)alkyl-O-($C_1$-$C_6$)alkyl]-ribose, 2'-$NH_2$-2'-deoxyribose, β-D-xylo-furanose, α-arabinofuranose, 2,4-dideoxy-β-D-erythro-hexo-pyranose, and carbocyclic (described, for example, in Froehler (1992) *J Am Chem Soc* 114:8320) and/or open-chain sugar analogs (described, for example, in Vandendriessche et al. (1993) *Tetrahedron* 49:7223) and/or bicyclosugar analogs (described, for example, in Tarkov M et al. (1993) *Helv Chim Acta* 76:481).

In some embodiments the sugar is 2'-O-methylribose, particularly for one or both nucleotides linked by a phosphodiester or phosphodiester-like internucleoside linkage.

Nucleic acids also include substituted purines and pyrimidines such as C-5 propyne pyrimidine and 7-deaza-7-substituted purine modified bases. Wagner R W et al. (1996) *Nat Biotechnol* 14:840-4. Purines and pyrimidines include but are not limited to adenine, cytosine, guanine, thymine, and uracil, and other naturally and non-naturally occurring nucleobases, substituted and unsubstituted aromatic moieties.

A modified base is any base which is chemically distinct from the naturally occurring bases typically found in DNA and RNA such as T, C, G, A, and U, but which share basic chemical structures with these naturally occurring bases. The modified nucleoside base may be, for example, selected from hypoxanthine, uracil, dihydrouracil, pseudouracil, 2-thiouracil, 4-thiouracil, 5-aminouracil, 5-($C_1$-$C_6$)-alkyluracil, 5-($C_2$-$C_6$)-alkenyluracil, 5-($C_2$-$C_6$) -5-(hydroxymethyl) uracil, 5-chlorouracil, 5-fluorouracil, 5-bromouracil, 5-hydroxycytosine, 5-($C_1$-$C_6$)-alkylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 2,4-diamino-purine, 8-azapurine, a substituted 7-deazapurine, preferably 7-deaza-7-substituted and/or 7-deaza-8-substituted purine, 5-hydroxymethylcytosine, N4-alkylcytosine, e.g., N4-ethylcytosine, 5-hydroxydeoxycytidine, 5-hydroxymethyldeoxycytidine, N4-alkyldeoxycytidine, e.g., N4-ethyldeoxycytidine, 6-thiodeoxyguanosine, and deoxyribonucleosides of nitropyrrole, C5-propynylpyrimidine, and diaminopurine e.g., 2,6-diaminopurine, inosine, 5-methylcytosine, 2-aminopurine, 2-amino-6-chloropurine, hypoxanthine or other modifications of a natural nucleoside bases. This list is meant to be exemplary and is not to be interpreted to be limiting.

In particular formulas described herein modified bases may be incorporated. For instance a cytosine may be replaced with a modified cytosine. A modified cytosine as used herein is a naturally occurring or non-naturally occurring pyrimidine base analog of cytosine which can replace this base without impairing the immunostimulatory activity of the oligonucleotide. Modified cytosines include but are not limited to 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines (e.g., 6-hydroxy-cytosine), N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil). Some of the preferred cytosines include 5-methyl-cytosine, 5-fluoro-cytosine, 5-hydroxy-cytosine, 5-hydroxymethyl-cytosine, and N4-ethyl-cytosine. In another embodiment of the invention, the cytosine base is substituted by a universal base (e.g., 3-nitropyrrole, P-base), an aromatic ring system (e.g., fluorobenzene or difluorobenzene) or a hydrogen atom (dSpacer).

A guanine may be replaced with a modified guanine base. A modified guanine as used herein is a naturally occurring or non-naturally occurring purine base analog of guanine which can replace this base without impairing the immunostimulatory activity of the oligonucleotide. Modified guanines include but are not limited to 7-deazaguanine, 7-deaza-7-substituted guanine (such as 7-deaza-7-(C2-C6)alkynylguanine), 7-deaza-8-substituted guanine, hypoxanthine, N2-substituted guanines (e.g., N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g., N6-methyl-adenine, 8-oxo-adenine), 8-substituted guanine (e.g., 8-hydroxyguanine and 8-bromoguanine), and 6-thioguanine. In another embodiment of the invention, the guanine base is substituted by a universal base (e.g., 4-methyl-indole, 5-nitro-indole, and K-base), an aromatic ring system (e.g., benzimidazole or dichloro-benzimidazole, 1-methyl-1 H-[1,2,4]triazole-3-carboxylic acid amide) or a hydrogen atom (dSpacer).

In one embodiment both the C and the G of a CG dinucleotide are unmodified cytosine and guanine-bases, respectively. In one embodiment the C of a CG dinucleotide is unmethylated.

For use in the instant invention, the oligonucleotides of the invention can be synthesized de novo using any of a number of procedures well known in the art, for example, the β-cyanoethyl phosphoramidite method (Beaucage S L et al. (1981) *Tetrahedron Lett* 22:1859); or the nucleoside H-phosphonate method (Garegg et al. (1986) *Tetrahedron Lett* 27:4051-4; Froehler BC et al. (1986) *Nucleic Acids Res* 14:5399-407; Garegg et al. (1986) *Tetrahedron Lett* 27:4055-8; Gaffney et al. (1988) *Tetrahedron Lett* 29:2619-22). These chemistries can be performed by a variety of automated nucleic acid synthesizers available in the market. These oligonucleotides are referred to as synthetic oligonucleotides. An isolated oligonucleotide generally refers to an oligonucleotide which is separated from components which it is normally associated with in nature. As an example, an isolated oligonucleotide may be one which is separated from a cell, from a nucleus, from mitochondria or from chromatin.

Modified backbones such as phosphorothioates may be synthesized using automated techniques employing either phosphoramidate or H-phosphonate chemistries. Aryl-and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (e.g., Uhlmann E et al. (1990) *Chem Rev* 90:544; Goodchild J (1990) *Bioconjugate Chem* 1:165).

The immunostimulatory oligonucleotides may also contain one or more unusual linkages between the nucleotide or nucleotide-analog moieties. The usual internucleoside linkage is the 3'5'-linkage. All other linkages are considered as unusual internucleoside linkages, such as 2'5'-, 5'5'-, 3'3'-, 2'2'-, and 2'3'-linkages. Thereby, the nomenclature 2' to 5'is chosen according to the carbon atom of ribose. However, if unnatural sugar moieties are employed, such as ring-expanded sugar analogs (e.g., hexanose, cylohexene, or pyranose) or bi- or tricyclic sugar analogs, then this nomenclature changes according to the nomenclature of the monomer. In 3'-deoxy-β-D-ribopyranose analogs (also called p-DNA), the mononucleotides are e.g. connected via a 4'2'-linkage.

If the nucleotide contains one 3'3'-linkage, then this oligonucleotide analog will usually have two unlinked 5'-ends. Similarly, if the nucleotide contains one 5'5'-linkage, then this oligonucleotide analog will usually have two unlinked 3'-ends. The accessibility of unlinked ends of nucleotides may be better accessible by their receptors. Both types of unusual linkages (3'3'- and 5'5'-) were described by Ortigao J F et al. (1992) *Antisense Res Dev* 2:129-46, whereby oligonucleotides having a 3'3'-linkage were reported to show enhanced stability towards cleavage by nucleases.

Different types of linkages can also be combined in one molecule which may lead to branching of the oligomer. If one part of the oligonucleotide is connected at the 3'-end via a 3'3'-linkage to a second oligonucleotide part and at the 2'-end via a 2'3'-linkage to a third part of the molecule, this results e.g. in a branched oligonucleotide with three 5'-ends (3'3'-, 2'3'-branched).

In principle, linkages between different parts of an oligonucleotide or between different oligonucleotides, respectively, can occur via all parts of the molecule, as long as this does not negatively interfere with the recognition by its receptor. According to the nature of the nucleic acid, the linkage can involve the sugar moiety (Su), the heterocyclic nucleobase (Ba) or the phosphate backbone (Ph). Thus, linkages of the type Su-Su, Su-Ph, Su-Ba, Ba-Ba, Ba-Su, Ba-Ph, Ph-Ph, Ph-Su, and Ph-Ba are possible. If the oligonucleotides are further modified by certain non-nucleotidic substituents, the linkage can also occur via the modified parts of the oligonucleotides. These modifications include also modified nucleic acids, e.g., PNA, LNA, or morpholino oligonucleotide analogs.

The linkages are preferably composed of C, H, N, O, S, B, P, and halogen, containing 3 to 300 atoms. An example with 3 atoms is an acetal linkage (ODN1-3'-O—CH$_2$—O-3'-ODN2; Froehler and Matteucci) connecting e.g. the 3'-hydroxy group of one nucleotide to the 3'-hydroxy group of a second oligonucleotide. An example with about 300 atoms is PEG-40 (tetraconta polyethyleneglycol). Preferred linkages are phosphodiester, phosphorothioate, methylphosphonate, phosphoramidate, boranophosphonate, amide, ether, thioether, acetal, thioacetal, urea, thiourea, sulfonamide, Schiff base, and disulfide linkages. Another possibility is the use of the Solulink BioConjugation System (TriLink BioTechnologies, San Diego, Calif.).

If the oligonucleotide is composed of two or more sequence parts, these parts can be identical or different. Thus, in an oligonucleotide with a 3'3'-linkage, the sequences can be identical, e.g., 5'-ODN1-3'3'-ODN1-5', or different, e.g., 5'-ODN1-3'3'-ODN2-5'. Furthermore, the chemical modification of the various oligonucleotide parts as well as the linker connecting them may be different. Since the uptake of short oligonucleotides appears to be less efficient than that of long oligonucleotides, linking of two or more short sequences results in improved immune stimulation. The length of the short oligonucleotides is preferably 2-20 nucleotides, more preferably 3-16 nucleotides, but most preferably 5-10 nucleotides. Preferred are linked oligonucleotides which have two or more unlinked 5'-ends.

The oligonucleotide partial sequences may also be linked by non-nucleotidic linkers, in particular abasic linkers (dSpacers), triethylene glycol units or hexaethylene glycol units. Other linkers include alkylamino linkers, such as C3, C6, C12 amino linkers, and also alkylthiol linkers, such as C3 or C6 thiol linkers. The oligonucleotides can also be linked by aromatic residues which may be further substituted by alkyl or substituted alkyl groups.

The oligonucleotides may also contain a doubler or trebler unit (Glen Research, Sterling, Va.), in particular those oligonucleotides with a 3'3'-linkage. A doubler unit in one embodiment can be based on 1,3-bis-[5-(4,4'-dimethoxytrityloxy) pentylamido]propyl-2-[(2-cyanoethyl)-(N,N-diisopropyl)]-phosphoramidite. A trebler unit in one embodiment can be based on incorporation of Tris-2,2,2-[3-(4,4'-dimethoxytrityloxy)propyloxymethyl]ethyl-[(2-cyanoethyl)-(N,N-diisopropyl)]-phosphoramidite. Branching of the oligonucleotides by multiple doubler, trebler, or other multiplier units leads to dendrimers which are a further embodiment of this invention. The oligonucleotides may also contain linker units resulting from peptide-modifying reagents or oligonucleotide-modifying reagents (Glen Research, Sterling, Va.). Furthermore, linkers may contain one or more natural or unnatural amino acid residues which are connected by peptide (amide) linkages.

Another possibility for linking oligonucleotides is via crosslinking of the heterocyclic bases (Verma S et al (1998) *Annu Rev Biochem* 67:99-134; page 124). Yet another possibility is a linkage between the sugar moiety of one sequence part with the heterocyclic base of another sequence part (Iyer et al. (1999) *Curr Opin Mol Therapeutics* 1:344-58; page 352).

The different oligonucleotides containing unusual linkages are synthesized by established methods and can be linked together on-line during solid-phase synthesis. Alternatively, they may be linked together following synthesis of the individual partial sequences.

CpG phosphorothioate oligonucleotides with strong stimulatory activity in the mouse system tend to show lower activity on human and other non-rodent immune cells. DNA containing these $(TCG)_nN$ or $RDCGY_1Y_2N$ motifs strongly stimulated human peripheral blood cells to produce IFN-α.

It has been discovered according to the invention that the subsets of CpG immunostimulatory oligonucleotides have dramatic immune stimulatory effects on human cells such as PBMC, suggesting that these CpG immunostimulatory oligonucleotides are effective therapeutic agents for human vaccination, cancer immunotherapy, asthma immunotherapy, general enhancement of immune function, enhancement of hematopoietic recovery following radiation or chemotherapy, and other immune modulatory applications.

As used herein, the terms treat, treated, or treating, when used with respect to a disorder such as an infectious disease, cancer, allergy, or asthma, refers to a prophylactic treatment which increases the resistance of a subject to development of the disease (e.g., to infection with a pathogen) or, in other words, decreases the likelihood that the subject will develop the disease (e.g., become infected with the pathogen), as well as to a treatment after the subject has developed the disease in order to fight the disease (e.g., reduce or eliminate the infection) or to prevent the disease from becoming worse.

Thus the CpG immunostimulatory oligonucleotides are useful in some aspects of the invention as a vaccine for the treatment of a subject having or at risk of developing allergy or asthma, an infection with an infectious organism, or a cancer in which a specific cancer antigen has been identified. The CpG immunostimulatory oligonucleotides thus can be administered to a subject in conjunction with an antigen or allergen for treatment of infection, allergy, asthma, or cancer. Alternatively and in addition, the CpG immunostimulatory oligonucleotides can also be given alone without the antigen or allergen for protection against infection, allergy or cancer or may be administered with other therapeutic agents. The CpG immunostimulatory oligonucleotides also may be administered with other therapeutic agents. Repeated doses may allow longer term protection.

A subject at risk as used herein is a subject who has any identifiable risk of exposure to an infection-causing pathogen or allergen or a risk of developing cancer. For instance, a subject at risk of developing infection may be a subject who is planning to travel to an area where a particular type of infectious agent is found, or it may be a subject who through lifestyle or medical procedures is exposed to bodily fluids which may contain infectious organisms or directly to the organism, or it may be any subject living in an area where an infectious organism or an allergen has been identified. Subjects at risk of developing infection also include general populations to which a medical agency recommends vaccination with a particular infectious organism antigen. If the antigen is an allergen and the subject develops allergic responses to that particular antigen and the subject may be exposed to the antigen, e.g., during pollen season, then that subject is at risk of developing an allergic response. A subject at risk of developing an allergy or asthma includes those subjects that have been identified as having an allergy or asthma but that do not have active disease during the CpG immunostimulatory oligonucleotide treatment. A subject at risk of developing an allergy or asthma also includes subjects that are considered to be at risk of developing these diseases because of genetic or environmental factors.

A subject at risk of developing a cancer is one who has a high probability of developing cancer. These subjects include, for instance, subjects having a genetic abnormality, the presence of which has been demonstrated to have a correlative relation to a higher likelihood of developing a cancer, subjects exposed to cancer-associated agents such as tobacco, asbestos, or other chemical toxins, and subjects who have previously been treated for cancer and are in apparent remission. When a subject at risk of developing a cancer is treated with a CpG immunostimulatory oligonucleotide and optionally an antigen specific for the type of cancer to which the subject is at risk of developing, the subject may be able to kill the cancer cells as they develop. If a tumor begins to form in the subject, the subject will develop an innate immune response or a specific immune response against the tumor antigen.

In addition to the use of the CpG immunostimulatory oligonucleotides for prophylactic treatment, the invention also encompasses the use of the CpG immunostimulatory oligonucleotides for the treatment of a subject having an infection, an allergy, asthma, or a cancer.

A subject having an infection is a subject that has been exposed to an infectious pathogen and has acute or chronic detectable levels of the pathogen in the body. The CpG immunostimulatory oligonucleotides can be used with or without an antigen or other therapeutic to mount an innate or an antigen specific systemic or mucosal immune response that is capable of reducing the level of or eradicating the infectious pathogen. An infectious disease, as used herein, is a disease arising from the presence of a foreign microorganism in the body. It is particularly important to develop effective vaccine strategies and treatments to protect the body's mucosal surfaces, which are the primary site of pathogenic entry.

A subject having an allergy is a subject that is capable of developing an allergic reaction in response to an allergen. An allergy refers to acquired hypersensitivity to a substance (allergen). Allergic conditions include but are not limited to eczema, allergic rhinitis or coryza, hay fever, conjunctivitis, bronchial asthma, allergic asthma, urticaria (hives), food allergies, and other atopic conditions.

Allergies are generally caused by IgE antibody generation against harmless allergens. The cytokines that are induced by systemic or mucosal administration of CpG immunostimulatory oligonucleotides are predominantly of a class called Th1 (examples are IL-12, IP-10, IFN-$\alpha$ and IFN-$\gamma$) and these induce both humoral and cellular immune responses. The other major type of immune response, which is associated with the production of IL-4 and IL-5 cytokines, is termed a Th2 immune response. In general, it appears that allergic diseases are mediated by Th2 type immune responses. Based on the ability of the CpG immunostimulatory oligonucleotides described herein to shift the immune response in a subject from a predominant Th2 (which is associated with production of IgE antibodies and allergy) to a balanced Th2/Th1 response (which is protective against allergic reactions), an effective dose for inducing an immune response of a CpG immunostimulatory oligonucleotide can be administered to a subject to treat asthma and allergy.

Thus, the CpG immunostimulatory oligonucleotides have significant therapeutic utility in the treatment of allergic conditions and asthma. Th2 cytokines, especially IL-4 and IL-5, are elevated in the airways of asthmatic subjects. These cytokines promote important aspects of the asthmatic inflammatory response, including IgE isotype switching, eosinophil chemotaxis and activation, and mast cell growth. Th1 cytokines, especially IFN-$\gamma$ and IL-12, can suppress the formation of Th2 clones and production of Th2 cytokines. Asthma refers to a disorder of the respiratory system characterized by inflammation, narrowing of the airways and increased reactivity of the airways to inhaled agents. Asthma is frequently, although not exclusively associated with atopic or allergic symptoms. Thus, asthma includes allergic asthma and non-allergic asthma.

A subject having a cancer is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g., small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

A subject shall mean a human or vertebrate animal including but not limited to a dog, cat, horse, cow, pig, sheep, goat, turkey, chicken, primate, e.g., monkey, and fish (aquaculture species), e.g., salmon. Thus, the compounds may be used to treat cancer and tumors, infections, and allergy/asthma in human and non-human subjects. Cancer is one of the leading causes of death in companion animals (e.g., cats and dogs).

In the instances when the CpG oligonucleotide is administered with an antigen, the subject may be exposed to the antigen. As used herein, the term "exposed to" refers to either the active step of contacting the subject with an antigen or the passive exposure of the subject to the antigen in vivo. Methods for the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the CpG immunostimulatory oligonucleotide are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface.

The methods in which a subject is passively exposed to an antigen can be particularly dependent on timing of administration of the CpG immunostimulatory oligonucleotide. For instance, in a subject at risk of developing a cancer or an infectious disease or an allergic or asthmatic response, the subject may be administered the CpG immunostimulatory oligonucleotide on a regular basis when that risk is greatest, e.g., during allergy season or after exposure to a cancer causing agent. Additionally the CpG immunostimulatory oligonucleotide may be administered to travelers before they travel to foreign lands where they are at risk of exposure to infectious agents. Likewise the CpG immunostimulatory oligonucleotide may be administered to soldiers or civilians at risk of exposure to biowarfare to induce a systemic or mucosal immune response to the antigen when and if the subject is exposed to it.

An antigen as used herein is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and muticellular organisms such as parasites and allergens. The term antigen broadly includes any type of molecule which is recognized by a host immune system as being foreign. Antigens include but are not limited to cancer antigens, microbial antigens, and allergens.

A cancer antigen as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen P A et al. (1994) *Cancer Res* 54:1055-8, by partially purifying the antigens, by recombinant technology, or by de novo synthesis of known antigens. Cancer antigens include but are not limited to antigens that are recombinantly expressed, an immunogenic portion thereof, or a whole tumor or cancer cell. Such antigens can be isolated or prepared recombinantly or by any other means known in the art.

As used herein, the terms "cancer antigen" and "tumor antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

A microbial antigen as used herein is an antigen of a microorganism and includes but is not limited to viruses, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Examples of viruses that have been found in humans include but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arena viridae (hemorrhagic fever viruses); Reoviridae (e.g., reoviruses, orbiviurses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), Hepatitis C; Norwalk and related viruses, and astroviruses).

Both gram negative and gram positive bacteria serve as antigens in vertebrate animals. Such gram positive bacteria include, but are not limited to, *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to, *Helicobacter pyloris, Borrelia burgdorferi, Legionella pneumophilia, Mycobacteria* sps (e.g., *M. tuberculosis, M. avium, M. intracellulare, M. kansasii, M. gordonae*), *Staphylococcus* aureus, Neisseria gonorrhoeae, Neisseria meningitidis, Listeria monocytogenes, Streptococcus pyogenes (Group A Streptococcus), Streptococcus agalactiae (Group B Streptococcus), Streptococcus (viridans group), Streptococcus faecalis, Streptococcus bovis, Streptococcus (anaerobic sps.), Streptococcus pneumoniae, pathogenic Campylobacter sp., Enterococcus sp., Haemophilus influenzae, Bacillus anthracis, Corynebacterium diphtheriae, Corynebacterium sp., Erysipelothrix rhusiopathiae, Clostridium perfringens, Clostridium tetani, Enterobacter aerogenes, Klebsiella pneumoniae, Pasturella multocida, Bacteroides sp., Fusobacterium nucleatum, Streptobacillus moniliformis, Treponema pallidum, Treponema pertenue, Leptospira, Rickettsia, and Actinomyces israelii.

Examples of fungi include Cryptococcus neoformans, Histoplasma capsulatum, Coccidioides immitis, Blastomyces dermatitidis, Chlamydia trachomatis, Candida albicans.

Other infectious organisms (i.e., protists) include Plasmodium spp. such as Plasmodium falciparum, Plasmodium malariae, Plasmodium ovale, and Plasmodium vivax and Toxoplasma gondii. Blood-borne and/or tissues parasites include Plasmodium spp., Babesia microti, Babesia divergens, Leishmania tropica, Leishmania spp., Leishmania braziliensis, Leishmania donovani, Trypanosoma gambiense and Trypanosoma rhodesiense (African sleeping sickness), Trypanosoma cruzi (Chagas' disease), and Toxoplasma gondii.

Other medically relevant microorganisms have been described extensively in the literature, e.g., see C. G. A Thomas, Medical Microbiology, Bailliere Tindall, Great Britain 1983, the entire contents of which is hereby incorporated by reference.

An allergen refers to a substance (antigen) that can induce an allergic or asthmatic response in a susceptible subject. The list of allergens is enormous and can include pollens, insect venoms, animal dander, dust, fungal spores and drugs (e.g., penicillin). Examples of natural, animal and plant allergens include but are not limited to proteins specific to the following genuses: Canine (Canis familiaris); Dermatophagoides (e.g., Dermatophagoides farinae); Felis (Felis domesticus); Ambrosia (Ambrosia artemiisfolia; Lolium (e.g., Lolium perenne or Lolium multiflorum); Cryptomeria (Cryptomeria japonica); Alternaria (Alternaria alternata); Alder; Alnus (Alnus gultinoasa); Betula (Betula verrucosa); Quercus (Quercus alba); Olea (Olea europa); Artemisia (Artemisia vulgaris); Plantago (e.g., Plantago lanceolata); Parietaria (e.g., Parietaria officinalis or Parietaria judaica); Blattella (e.g., Blattella germanica); Apis (e.g., Apis multiflorum); Cupressus (e.g., Cupressus sempervirens, Cupressus arizonica and Cupressus macrocarpa); Juniperus (e.g., Juniperus sabinoides, Juniperus virginiana, Juniperus communis and Juniperus ashei); Thuya (e.g., Thuya orientalis); Chamaecyparis (e.g., Chamaecyparis obtusa); Periplaneta (e.g., Periplaneta americana); Agropyron (e.g., Agropyron repens); Secale (e.g., Secale cereale); Triticum (e.g., Triticum aestivum); Dactylis (e.g., Dactylis glomerata); Festuca (e.g., Festuca elatior); Poa (e.g., Poa pratensis or Poa compressa); Avena (e.g., Avena sativa); Holcus (e.g., Holcus lanatus); Anthoxanthum (e.g., Anthoxanthum odoratum); Arrhenatherum (e.g., Arrhenatherum elatius); Agrostis (e.g., Agrostis alba); Phleum (e.g., Phleum pratense); Phalaris (e.g., Phalaris arundinacea); Paspalum (e.g., Paspalum notatum); Sorghum (e.g., Sorghum halepensis); and Bromus (e.g., Bromus inermis).

The antigen may be substantially purified. The term substantially purified as used herein refers to an antigen, i.e., a polypeptide which is substantially free of other proteins, lipids, carbohydrates or other materials with which it is naturally associated. One skilled in the art can purify polypeptide antigens using standard techniques for protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the polypeptide antigen may also be determined by amino-terminal amino acid sequence analysis. Other types of antigens such as polysaccharides, small molecule, mimics, etc., are included within the invention and may optionally be substantially pure.

The oligonucleotides of the invention may be administered to a subject with an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses. Anti-fungal agents are used to treat superficial fungal infections as well as opportunistic and primary systemic fungal infections. Anti-parasitic agents kill or inhibit parasites.

Examples of anti-parasitic agents, also referred to as parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflomithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide some of which are used alone or in combination with others.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g., amantadine), synthesis or translation of viral mRNA (e.g., interferon), replication of viral RNA or DNA (e.g., nucleoside analogs), maturation of new virus proteins (e.g., protease inhibitors), and budding and release of the virus.

Nucleotide analogs are synthetic compounds which are similar to nucleotides, but which have an incomplete or abnormal deoxyribose or ribose group. Once the nucleotide analogs are in the cell, they are phosphorylated, producing the triphosphate form which competes with normal nucleotides for incorporation into the viral DNA or RNA. Once the triphosphate form of the nucleotide analog is incorporated into the growing nucleic acid chain, it causes irreversible association with the viral polymerase and thus chain termination. Nucleotide analogs include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines which are secreted by virus-infected cells as well as immune cells. The interferons function by binding to specific receptors on cells adjacent to the infected cells, causing the change in the cell which protects it from infection by the virus. $\alpha$ and $\beta$-interferon also induce the expression of Class I and Class II MHC molecules on the surface of infected cells, resulting in increased antigen presentation for host immune cell recognition. $\alpha$ and $\beta$-interferons are available as recombinant forms and have been used for the treatment of chronic hepatitis B and C infection. At the dosages which are effective for anti-viral therapy, interferons have severe side effects such as fever, malaise and weight loss.

Anti-viral agents useful in the invention include but are not limited to immunoglobulins, amantadine, interferons, nucleoside analogs, and protease inhibitors. Specific examples of anti-virals include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, imidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g., chitinase) or immunosuppression (501 cream).

CpG immunostimulatory oligonucleotides can be combined with other therapeutic agents such as adjuvants to enhance immune responses. The CpG immunostimulatory oligonucleotide and other therapeutic agent may be administered simultaneously or sequentially. When the other therapeutic agents are administered simultaneously they can be administered in the same or separate formulations, but are administered at the same time. The other therapeutic agents are administered sequentially with one another and with CpG immunostimulatory oligonucleotide, when the administration of the other therapeutic agents and the CpG immunostimulatory oligonucleotide is temporally separated. More specifically, the CpG immunostimulatory oligonucleotide can be administered before or after administration of (or exposure to) at least one other therapeutic agent. The separation in time between the administration of these compounds may be a matter of minutes or it may be longer. Other therapeutic agents include but are not limited to adjuvants, cytokines, antibodies, antigens, etc.

The compositions of the invention may also be administered with non-nucleic acid adjuvants. A non-nucleic acid adjuvant is any molecule or compound except for the CpG immunostimulatory oligonucleotides described herein which can stimulate the humoral and/or cellular immune response. Non-nucleic acid adjuvants include, for instance, adjuvants that create a depot effect, immune stimulating adjuvants, and adjuvants that create a depot effect and stimulate the immune system.

The CpG immunostimulatory oligonucleotides are also useful as mucosal adjuvants. It has previously been discovered that both systemic and mucosal immunity are induced by mucosal delivery of CpG nucleic acids. Thus, the oligonucleotides may be administered in combination with other mucosal adjuvants.

Immune responses can also be induced or augmented by the co-administration or co-linear expression of cytokines (Bueler & Mulligan, 1996; Chow et al., 1997; Geissler et al., 1997; Iwasaki et al., 1997; Kim et al., 1997) or co-stimulatory molecules such as B7 (Iwasaki et al., 1997; Tsuji et al., 1997) with the CpG immunostimulatory oligonucleotides. The term cytokine is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to interleukin-1 (IL-1), IL-2, IL-3, IL-4, IL-5, IL-6, IL-7, IL-10, IL-12, IL-15, IL-18, granulocyte-macrophage colony stimulating factor (GM-CSF), granulocyte colony stimulating factor (G-CSF), IFN-$\gamma$, IFN-$\alpha$, IFN-$\beta$, tumor necrosis factor (TNF), TGF-$\beta$, Flt-3 ligand, and CD40 ligand. In addition to cytokines the CpG oligonucleotides may be used in combination with antibodies against certain cytokines, such as anti-IL-10 and anti-TGF-β, as well as cyclooxygenase inhibitors, i.e., COX-1 and COX-2 inhibitors.

The oligonucleotides are also useful for redirecting an immune response from a Th2 immune response to a Th1 immune response. This results in the production of a relatively balanced Th1/Th2 environment. Redirection of an immune response from a Th2 to a Th1 immune response can be assessed by measuring the levels of cytokines produced in response to the nucleic acid (e.g., by inducing monocytic cells and other cells to produce Th1 cytokines, including IFN-α). The redirection or rebalance of the immune response from a Th2 to a Th1 response is particularly useful for the treatment of asthma. For instance, an effective amount for treating asthma can be that amount useful for redirecting a Th2 type of immune response that is associated with asthma to a Th1 type of response or a balanced Th1/Th2 environment. Th2 cytokines, especially IL-4 and IL-5 are elevated in the airways of asthmatic subjects. The CpG immunostimulatory oligonucleotides described herein cause an increase in Th1 cytokines which helps to rebalance the immune system, preventing or reducing the adverse effects associated with a predominately Th2 immune response.

Redirection of an immune response from a Th2 to a Th1 immune response can also be assessed by measuring the levels of specific isotypes of immunoglobulin. For example, in mice IgG2a is associated with a Th1 immune response, and IgG1 and IgE are associated with a Th2 immune response.

The CpG immunostimulatory oligonucleotides have the unique capability to promote cell survival, differentiation, activation and maturation of dendritic cells, and are useful for in vitro, in vivo, and ex vivo methods involving dendritic cells.

CpG immunostimulatory oligonucleotides also increase natural killer cell lytic activity and antibody-dependent cellular cytotoxicity (ADCC). ADCC can be performed using a CpG immunostimulatory oligonucleotide in combination with an antibody specific for a cellular target, such as a cancer cell. When the CpG immunostimulatory oligonucleotide is administered to a subject in conjunction with the antibody, the subject's immune system is induced to kill the tumor cell. The antibodies useful in the ADCC procedure include antibodies which interact with a cell in the body. Many such antibodies specific for cellular targets have been described in the art and many are commercially available.

The CpG immunostimulatory oligonucleotides may also be administered in conjunction with an anti-cancer therapy. Anti-cancer therapies include cancer medicaments, radiation and surgical procedures. As used herein, a "cancer medicament" refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

Additionally, the methods of the invention are intended to embrace the use of more than one cancer medicament along with the CpG immunostimulatory oligonucleotides. As an example, where appropriate, the CpG immunostimulatory oligonucleotides may be administered with both a chemotherapeutic agent and an immunotherapeutic agent. Alternatively, the cancer medicament may embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

The chemotherapeutic agent may be selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS famesyl transferase inhibitor, famesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, PlantinoUcisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analog), Lomustine (CCNU), Mechlorethamine HCl (nitrogen mustard), Mercaptopurine, Mesna, Mitotane (o.p-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26), and Vindesine sulfate, but it is not so limited.

The immunotherapeutic agent may be selected from the group consisting of Rituxan, Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab, and ImmuRAIT-CEA, but it is not so limited.

The cancer vaccine may be selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vaccine, TA-HPV, TA-CIN, DISC-virus and ImmuCyst/TheraCys, but it is not so limited.

The use of CpG immunostimulatory oligonucleotides in conjunction with immunotherapeutic agents such as monoclonal antibodies is able to increase long-term survival through a number of mechanisms including significant enhancement of ADCC (as discussed above), activation of NK cells and an increase in IFN-α levels. The nucleic acids when used in combination with monoclonal antibodies serve to reduce the dose of the antibody required to achieve a biological result.

The invention also includes methods for inducing antigen non-specific innate immune activation and broad spectrum resistance to infectious challenge using the CpG immunostimulatory oligonucleotides. The term innate immune activation as used herein refers to the activation of immune cells other than memory B cells and for instance can include the activation of monocytes, neutrophils, macrophages, dendritic cells, NK cells, and/or other immune cells that can respond in an antigen-independent fashion. A broad spectrum resistance to infectious challenge is induced because the immune cells are in active form and are primed to respond to any invading compound or microorganism. The cells do not have to be specifically primed against a particular antigen. This is particularly useful in biowarfare, and the other circumstances described above such as travelers.

The CpG immunostimulatory oligonucleotides may be directly administered to the subject or may be administered in conjunction with a nucleic acid delivery complex. A nucleic acid delivery complex shall mean a nucleic acid molecule associated with (e.g., ionically or covalently bound to; or encapsulated within) a targeting means (e.g., a molecule that results in higher affinity binding to target cell. Examples of nucleic acid delivery complexes include nucleic acids associated with a sterol (e.g., cholesterol), a lipid (e.g., a cationic lipid, virosome or liposome), or a target cell specific binding agent (e.g., a ligand recognized by target cell specific receptor). Preferred complexes may be sufficiently stable in vivo to prevent significant uncoupling prior to internalization by the target cell. However, the complex can be cleavable under appropriate conditions within the cell so that the oligonucleotide is released in a functional form.

The CpG immunostimulatory oligonucleotide and/or the antigen and/or other therapeutics may be administered alone (e.g., in saline or buffer) or using any delivery vehicles known in the art. For instance the following delivery vehicles have been described: Cochleates (Gould-Fogerite et al., 1994, 1996); Emulsomes (Vancott et al., 1998, Lowell et al., 1997); ISCOMs (Mowat et al., 1993, Carlsson et al., 1991, Hu et., 1998, Morein et al., 1999); Liposomes (Childers et al., 1999, Michalek et al., 1989, 1992, de Haan 1995a, 1995b);

Live bacterial vectors (e.g., *Salmonella, Escherichia coli*, bacillus Calmette-Guérin, *Shigella, Lactobacillus*) (Hone et al., 1996, Pouwels et al., 1998, Chatfield et al., 1993, Stover et al., 1991, Nugent et al., 1998); Live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); Microspheres (Gupta et al., 1998, Jones et al., 1996, Maloy et al., 1994, Moore et al., 1995, O'Hagan et al., 1994, Eldridge et al., 1989); Nucleic acid vaccines (Fynan et al., 1993, Kuklin et al., 1997, Sasaki et al., 1998, Okada et al., 1997, Ishii et al., 1997); Polymers (e.g., carboxymethylcellulose, chitosan) (Hamajima et al., 1998, Jabbal-Gill et al., 1998); Polymer rings (Wyatt et al., 1998); Proteosomes (Vancott et al., 1998, Lowell et al., 1988, 1996, 1997); Sodium Fluoride (Hashi et al., 1998); Transgenic plants (Tacket et al., 1998, Mason et al., 1998, Haq et al., 1995); Virosomes (Gluck et al., 1992, Mengiardi et al., 1995, Cryz et al., 1998); Virus-like particles (Jiang et al., 1999, Leibl et al., 1998). Other delivery vehicles are known in the art.

The term "effective amount" refers generally to the amount necessary or sufficient to realize a desired biologic effect. For example, an effective amount of a CpG immunostimulatory oligonucleotide administered with an antigen for inducing mucosal immunity is that amount necessary to cause the development of IgA in response to an antigen upon exposure to the antigen, whereas that amount required for inducing systemic immunity is that amount necessary to cause the development of IgG in response to an antigen upon exposure to the antigen. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular CpG immunostimulatory oligonucleotide being administered the size of the subject, or the severity of the disease or condition. One of ordinary skill in the art can empirically determine the effective amount of a particular CpG immunostimulatory oligonucleotide and/or antigen and/or other therapeutic agent without necessitating undue experimentation.

Subject doses of the compounds described herein for mucosal or local delivery typically range from about 10 µg to 10 g per administration, which depending on the application could be given daily, weekly, or monthly and any other amount of time therebetween or as otherwise required. More typically mucosal or local doses range from about 1 mg to 500 mg per administration, and most typically from about 1 mg to 100 mg, with 2-4 administrations being spaced days or weeks apart. More typically, immune stimulant doses range from 10 µg to 100 mg per administration, and most typically 100 µg to 10 mg, with daily or weekly administrations. Subject doses of the compounds described herein for parenteral delivery for the purpose of inducing an antigen-specific immune response, wherein the compounds are delivered with an antigen but not another therapeutic agent are typically 5 to 10,000 times higher than the effective mucosal dose for vaccine adjuvant or immune stimulant applications, and more typically 10 to 1,000 times higher, and most typically 20 to 100 times higher. Doses of the compounds described herein for parenteral delivery for the purpose of inducing an innate immune response or for increasing ADCC or for inducing an antigen specific immune response when the CpG immunostimulatory oligonucleotides are administered in combination with other therapeutic agents or in specialized delivery vehicles typically range from about 100 µg to 10 g per administration, which depending on the application could be given daily, weekly, or monthly and any other amount of time therebetween or as otherwise required. More typically parenteral doses for these purposes range from about 1 mg to 5 g per administration, and most typically from about 1 mg to 1 g, with 2-4 administrations being spaced days or weeks apart. In some embodiments, however, parenteral doses for these purposes may be used in a range of 5 to 10,000 times higher than the typical doses described above.

For any compound described herein the therapeutically effective amount can be initially determined from animal models. A therapeutically effective dose can also be determined from human data for other CpG oligonucleotides which have been tested in humans (human clinical trials are ongoing) and for compounds which are known to exhibit similar pharmacological activities, such as other adjuvants, e.g., LT and other antigens for vaccination purposes. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the CpG immunostimulatory oligonucleotide and/or other therapeutics can be administered to a subject by any mode that delivers the compound to the desired surface, e.g., local, mucosal, systemic. Administering the pharmaceutical composition of the present invention may be accomplished by any means known to the skilled artisan. Preferred routes of administration include but are not limited to oral, parenteral, intravenous, intramuscular, subcutaneous, intralesional, intratumoral, intranasal, sublingual, intratracheal, inhalation, ocular, vaginal, and rectal.

For oral administration, the compounds (i.e., CpG immunostimulatory oligonucleotides, antigens and/or other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

The compounds may be administered by inhalation to pulmonary tract, especially the bronchi and more particularly into the alveoli of the deep lung, using standard inhalation devices. The compounds may be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. An inhalation apparatus may be used to deliver the compounds to a subject. An inhalation apparatus, as used herein, is any device for administering an aerosol, such as dry powdered form of the compounds. This type of equipment is well known in the art and has been described in detail, such as that description found in Remington: The Science and Practice of Pharmacy, 19$^{th}$ Edition, 1995, Mac Publishing Company, Easton, Pa., pages 1676-1692. Many U.S. patents also describe inhalation devices, such as U.S. Pat. No. 6,116,237.

"Powder" as used herein refers to a composition that consists of finely dispersed solid particles. Preferably the compounds are relatively free flowing and capable of being dispersed in an inhalation device and subsequently inhaled by a subject so that the compounds reach the lungs to permit penetration into the alveoli. A "dry powder" refers to a powder composition that has a moisture content such that the particles are readily dispersible in an inhalation device to form an aerosol. The moisture content is generally below about 10% by weight (% w) water, and in some embodiments is below about 5% w and preferably less than about 3% w. The powder may be formulated with polymers or optionally may be formulated with other materials such as liposomes, albumin and/or other carriers.

Aerosol dosage and delivery systems may be selected for a particular therapeutic application by one of skill in the art, such as described, for example in Gonda, I. "Aerosols for delivery of therapeutic and diagnostic agents to the respiratory tract," in Critical Reviews in Therapeutic Drug Carrier Systems, 6:273-313 (1990), and in Moren, "Aerosol dosage forms and formulations," in Aerosols in Medicine. Principles, Diagnosis and Therapy, Moren, et al., Eds., Elsevier, Amsterdam, 1985.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as. cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may include suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R (1990) *Science* 249:1527-33, which is incorporated herein by reference.

The CpG immunostimulatory oligonucleotides and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a CpG immunostimulatory oligonucleotide and optionally antigens and/or other therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The present invention is further illustrated by the following Examples, which in no way should be construed as further limiting.

EXAMPLES

Example 1

C-Class ODN Analogs Induce IFN-α Secretion and Human TLR9 Activity In Vitro

In this series of experiments, C-class ODN analogs of the invention were tested in vitro for their ability to stimulate human peripheral blood mononuclear cells (PBMC) to secreted IFN-α and to stimulate HEK293 cells, stably transfected with human TLR9 and NF-κB reporter construct, to demonstrate TLR9 signaling.

ODN were purchased from Biospring (Frankfurt, Germany), and were controlled for identity and purity by Coley Pharmaceutical GmbH (Langenfeld, Germany). ODNs were diluted in phosphate-buffered saline (Sigma, Germany), and stored at −20° C. All dilutions were carried out using pyrogen-free reagents. Test ODN included the following:

```
128 T*C_G*T*C*G*T*T*T*T*A*C*G*G*C*G*T*C*G*T*G*C*C*G   (SEQ ID NO:48)

611 T*C*G*T*C*G*T*T*T*T*A*C_G*G*C_G*C*C_G*T*G*C*C*G   (SEQ ID NO:43)

614 T*C*G*T*C*G*T*T*T*T*A*C_G*G*C*G*C*C_G*T*G*C*C*G   (SEQ ID NO:43)

620 T*C*G*T*C_G*T*T*T*T*A*C_G*G*C*G*C*C_G*T*G*C*C*G   (SEQ ID NO:43)
```

```
331 T*C*G*C_G*A*C*G*T*T*C_G*G*C*G*C_G*C*T*G*C*C*G    (SEQ ID NO:27)

332 T*C*G*C_G*T*C*G*T*T*C_G*G*C*G*C_G*C*T*G*C*C*G    (SEQ ID NO:30)

333 T*C*G*C_G*A*C*G*T*T*C_G*G*C*G*C_G*T*C*G*C*C*G    (SEQ ID NO:28)

334 T*C*G*C_G*A*C*G*T*T*C_G*G*C*G*G*C_T*C*G*C*C*G    (SEQ ID NO:29)

335 T*C*G_C*G*T*C*G*T*T*C_G*G*C*G*C_G*C*T*G*C*C*G    (SEQ ID NO:30)

336 T*C*G*C*G_T*C*G*T*T*C_G*G*C*G*C_G*C*T*G*C*C*G    (SEQ ID NO:30)

337 T*C*G*C*G_A*C*G*T*T*C_G*G*C*G*C_G*T*C*G*C*C*G    (SEQ ID NO:28)

338 T*C*G*C*G_A*C*G*T*T*C_G*G*C*G*G*C_T*C*G*C*C*G    (SEQ ID NO:29)

339 T*C*G_C*G*A*C*G*T*T*C_G*G*C*G*C_G*T*C*G*C*C*G    (SEQ ID NO:28)

340 T*C*G_C*G*A*C*G*T*T*C_G*G*C*G*G*C_T*C*G*C*C*G    (SEQ ID NO:29)

341 T*C*G*C_G*T*C*G*T*T*C_G*G*C*G*C_G*T*C*G*C*C*G    (SEQ ID NO:31)

342 T*C*G*C_G*T*C*G*T*T*C_G*G*C*G*G*C_T*C*G*C*C*G    (SEQ ID NO:32)

343 T*C*G*C*G_T*C*G*T*T*C_G*G*C*G*C_G*T*C*G*C*C*G    (SEQ ID NO:31)

344 T*C*G*C*G_T*C*G*T*T*C_G*G*C*G*G*C_T*C*G*C*C*G    (SEQ ID NO:32)
``` wherein * represents phophorothioate linkage, and _ represents phosphodiester linkage. CpG ODN 2006 (TCGTCGTTTTGTCGTTTGTCGTT, SEQ ID NO:56) was used as a positive control for TLR9 signal activation. C-class CpG ODN 2429 (TCGTCGTTTTCGGCGGC-CGCCG, SEQ ID NO:53) was used as a positive control for IFN-α induction. Non-CpG ODN 1982 (TCCAGGACT-TCTCTCAGGTT, SEQ ID NO:18) was used as a negative control.

Peripheral blood buffy coat preparations from healthy male and female human donors were obtained from the Blood Bank of the University of Düsseldorf (Germany) and from these, PBMC were purified by centrifugation over Ficoll-Hypaque (Sigma). The purified PBMC were resuspended in RPMI 1640 culture medium (Bio Whittaker, Belgium) supplemented with 5% (v/v) heat-inactivated human AB serum (Bio Whittaker) or 10% (v/v) heat-inactivated FCS, 2 mM L-glutamine (Bio Whittaker), 100 U/ml penicillin and 100 μg/ml streptomycin (Invitrogen, Karlsruhe, Germany).

Fresh PBMC were seeded on 96-well round-bottom plates and incubated for 48 hours with ODN in the concentrations as indicated in a humidified incubator at 37° C. Culture supernatants were collected and if not used immediately, frozen at −20° C. until required.

Amounts of IFN-α in the supernatants were assessed using an enzyme-linked immunosorbent assay (ELISA) developed using commercially available antibodies (Alexis GmbH, Grünberg, Germany). ODN 128, 331-344, 611 and 620 were tested with PBMC from four different donors, and ODN 614 was tested with PBMC from three different donors.

Stably transfected HEK293 cells used for a human TLR9 reporter gene assay expressed the human TLR9 receptor and an NF-κB reporter gene construct. Cells were incubated with ODNs for 16 h at 37° C. in a humidified incubator. Each data point was done in triplicate. Cells were lysed and assayed for reporter gene activity. Stimulation indices were calculated in reference to reporter gene activity of medium without addition of ODN.

Results. Representative results are presented in FIG. 1 and FIG. 2. FIG. 1 shows that C-class ODN 332, 333, and 334 induced large amounts of IFN-α (ca. 2000-2500 pg/ml typical) when present at a concentration of 1 μM. The amount of IFN-a induced by these ODN significantly exceeded the amount of IFN-α induced by the same concentration of ODN 2006 or 1982. FIG. 1 also shows that C-class ODN 332, 333, and 334 induced significant amounts of TLR9 signaling activity (typically with a stimulation index of ca. 15) when present at a concentration of 10 μM. The amount of TLR9 signaling activity induced by these ODN was about half the TLR9 signaling activity induced by the same concentration of ODN 2006. Essentially the same results were observed for ODN 128 and 335-344.

Figure 2:
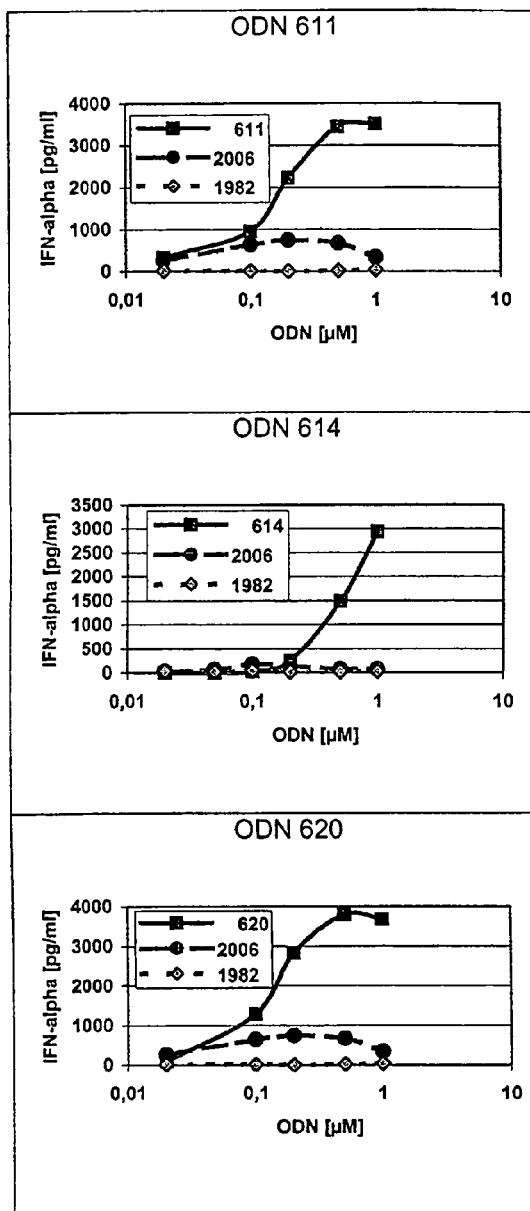
FIG. 2 is a series of graphs depicting induction of IFN-α and TLR9 signaling by ODN 611, 614, and 620.
Figure 2:
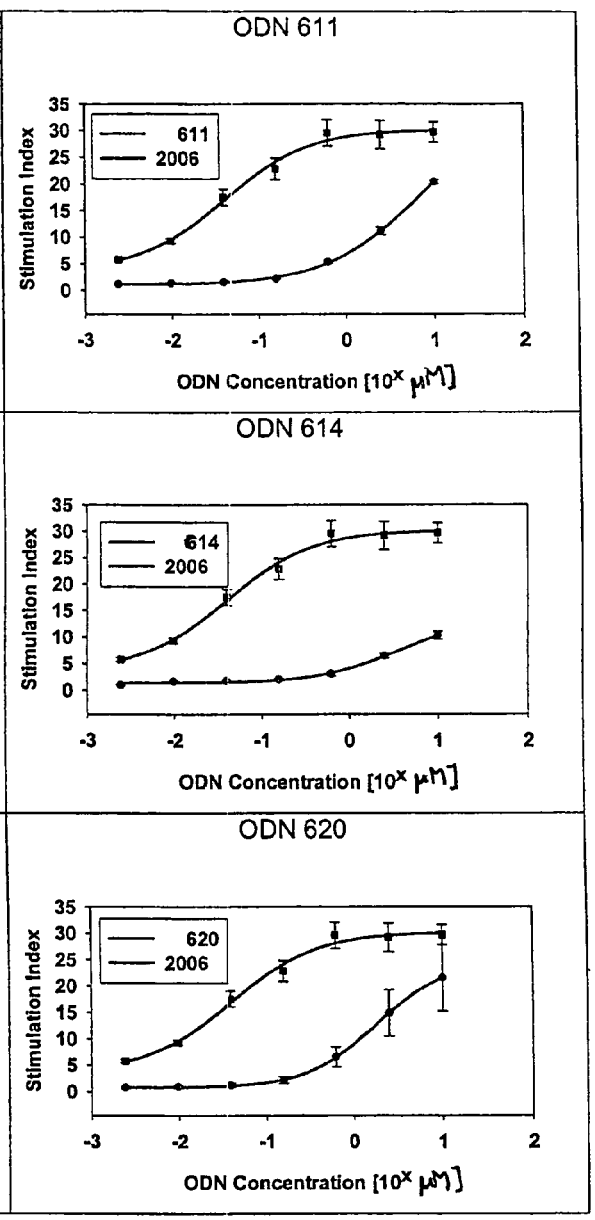

FIG. 2 shows that C-class ODN 611, 614, and 620 induced even greater amounts of IFN-α (ca. 3000-4000 pg/ml typical) when present at a concentration of 1 μM. The amount of IFN-α induced by these ODN significantly exceeded the amount of IFN-α induced by the same concentration of ODN 2006 or 1982. FIG. 2 also shows that C-class ODN 611, 614, and 620 induced significant amounts of TLR9 signaling activity (typically with a stimulation index of ca. 10-20) when present at a concentration of 10 μM. The amount of TLR9 signaling activity induced by these ODN was again about half the TLR9 signaling activity induced by the same concentration of ODN 2006.

Figure 3:
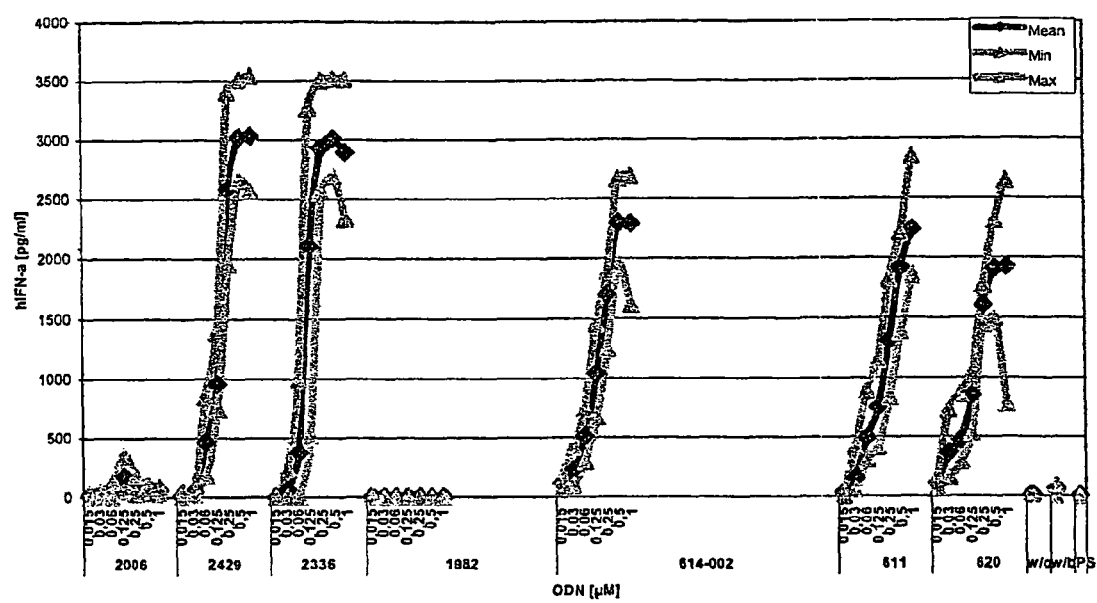
FIG. 3 is a graph depicting IFN-α production in peripheral blood mononuclear cells (PBMC) stimulated by a panel of oligonucleotides.

ODNs 611 (SEQ ID NO:43), 614 (SEQ ID NO:43), and 620 (SEQ ID NO:43) were also compared with ODN 2429 (one of the original palindrome-containing C-class oligonucleotides described). These new C-class ODN showed higher activity in the human TLR9 assay, while induction of IFN-α was similar to ODN 2429 (FIG. 3).

Taken together, the results of these experiments demonstrate that C-Class ODN analogs of the invention effectively induce IFN-α secretion and human TLR9 activity in vitro.

Example 2

Additional C-Class ODN Analogs Induce IFN-α Secretion In Vitro

In this series of experiments, additional C-class ODN analogs of the invention were tested in vitro for their ability to induce IFN-α secretion. The C-class ODN analogs in these experiments were characterized in part by the presence of AT-rich interrupted inverted repeats or by the presence of interrupted inverted repeats containing dSpacer residues in place of conventional nucleotide residues.

ODN were obtained as in Example 1. Test ODN included the following:

```
645 T*C*G*T*C_G*T*T*T*T*T*A*A*T*A*T*T*T*A*T*T*A        SEQ ID NO:59
646 T*C*G*T*C_G*T*T*T*T*C*A*A*T*A*T*T*T*A*T*T*G        SEQ ID NO:50
647 T*C*G*T*C_G*T*T*T*T*T*A*A*T*A*T*C*C*A*T*T*A        SEQ ID NO:58
649 T*C*G*T*C_G*T*T*T*T*A*C*G*G*C*G*L*L*L*T*G*C*C*G    SEQ ID NO:45
650 T*C*G*T*C_G*T*T*L*L*A*C*G*G*C*G*L*L*L*T*G*C*C*G    SEQ ID NO:38
651 T*C*G*T*C_G*T*T*T*T*C*G*G*C*G*G*L*L*C*C*G*C*C*G    SEQ ID NO:54
``` wherein * represents phosphorothioate internucleotide linkage, _ represents phosphodiester internucleotide linkage, and L represents dSpacer.

Human PBMC were obtained and treated in a manner analogous to Example 1.

Amounts of IFN-α in the supernatants were assessed using an enzyme-linked immunosorbent assay (ELISA) in a manner analogous to Example 1.

Results. C-class ODN 645, 646, and 647, characterized in part by the presence of AT-rich interrupted inverted repeats, induced moderate amounts of IFN-α (ca. 1200-1500 pg/ml typical) when present at a concentration of 1 µM. The amount of IFN-α induced by these ODN significantly exceeded the amount of IFN-α induced by the same concentration of ODN 2006 or 1982. C-class ODN 649, 650, and 651, characterized in part by the presence of interrupted inverted repeats containing dSpacer residues, induced large amounts of IFN-α (ca. 2000-2500 pg/ml typical) when present at a concentration of 1 µM. The amount of IFN-α induced by these ODN significantly exceeded the amount of IFN-α induced by the same concentration of ODN 2006 or 1982.

Taken together, the results of these experiments demonstrate that C-Class ODN analogs of the invention, characterized in part by the presence of AT-rich interrupted inverted repeats or by the presence of interrupted inverted repeats containing dSpacer residues in place of conventional nucleotide residues, effectively induce IFN-α secretion in vitro.

Example 3

Additional C-Class ODN Analogs Induce IFN-α Secretion and Human TLR9 Activity In Vitro In this series of experiments, C-class ODN analogs of the invention were tested in vitro for their ability to stimulate human PBMC to secreted IFN-α and to stimulate HEK293 cells, stably transfected with human TLR9 and NF-κB reporter construct, to demonstrate TLR9 signaling. The basic protocol is as described for Example 1, with the exception that the test ODN included the following:

```
664  T*C*G*A*C*G*T*C*G*A*C*G*T*G*A*C*G*T*G              (SEQ ID NO: 62)
376  T*C*G*A*C*G*T*C*G*A*C*G*T*G*A*C*G                  (SEQ ID NO: 61)
801  T*C_G*T*C_G*A*C_G*T*T*C_G*G*C*G*C*C_G*T*G*C*C*G    (SEQ ID NO: 65)
893  T*C*G*T*C_G*T*A*C_G*G*C*G*C*C_G*T*G*C*C*G          (SEQ ID NO: 66)
894  T*C*G*T*C_G*T*T*A*C_G*G*C*G*C*C_G*T*G*C*C*G        (SEQ ID NO: 67)
882  T*C*G*A*C*G*T*C*G*A*C*G*T*G*A*C*G*T*T              (SEQ ID NO: 63)
2290 T*C*G*T*C_G*A*C_G*A*T*C_G*G*C*G*C*C_G*T*G*C*C*G    (SEQ ID NO: 64)
2292 T*C*G*T*C*G*A*C*G*A_T_C*G*G*C*G*C*C*G*T*G*C*C*G    (SEQ ID NO: 64)
2337 T*C*G*A*C_G*T*C*G*A*C_G*T*G*A*C*G*T*T              (SEQ ID NO: 63)
2341 T*C*G*A*C_G*T*C*G*A*C*G*T_G*A*C*G*T*T              (SEQ ID NO: 63)
2357 T*C*G*T*C_G*T*T*T*A*C_G*G*C*G*C*C_G*T*G*C*C*G*T    (SEQ ID NO: 68)
``` wherein * represents phosphorothioate linkage and _ represents phophodiester linkage.

ODN in different conentrations were tested in the TLR9 reporter gene assay. The EC50 (concentration of ODN at which effect was 50 percent maximal effect) was calculated using SigmaPlot (SigmaPlot 2002 for Windows Version 8.0). The maximal stimulation index (max SI) was calculated as the quotient between the highest value of all concentrations tested for any ODN and the medium control. Results are shown in Table 1, wherein it can be seen that stimulation indices in the range of 10-30 were common.

TABLE 1

C-Class CpG ODN of the Invention Activate Human TLR9

| ODN | EC50 (nM) | max SI |
|---|---|---|
| 801 | 130 | 29 |
| 2341 | 2900 | 27 |
| 2357 | 1900 | 19 |
| 882 | 2700 | 15 |
| 893 | 3500 | 11 |
| 894 | 2800 | 11 |
| 2290 | 1200 | 11 |
| 2337 | 3900 | 11 |
| 664 | 1290 | 5 |
| 2292 | 2700 | 5 |
| 376 | 230 | 2 |

Large amounts of IFN-α were secreted by human PBMC upon 48 h incubation with these C-class CpG ODN. Typical amounts of IFN-α were in the range of 3000-4000 pg/ml following incubation with ODN at concentrations less than or equal to 1 µM. Response curves for IFN-α in these experiments were very similar to those shown in FIG. 2.

Example 4

C-Class ODN Analogs Induce Antigen-Specific Immune Response In Vivo

In this series of experiments, C-class ODN of the invention were tested in vivo in conjunction with vaccination of mice. C-class ODN of the invention were observed to boost titers of antigen-specific total IgG and IgG2a (Th1-like IgG in mice), as well as antigen-specific cytolytic T lymphocyte (CTL) responses, in a manner at least comparable to B-class CpG ODN 2006.

ODN were obtained as in Example 1.

Female BALB/c mice (6-8 weeks of age) were used for all experiments. Animals were purchased from Charles River Canada (Quebec, Canada) and housed in micro isolators at the animal care facility of the Ottawa Hospital Research Institute, Civic Site.

Naïve BALB/c mouse splenocytes were used for all in vitro assays. Animals were anesthetized with isofluorane and euthanized by cervical dislocation. Spleens were removed under aseptic conditions and placed in phosphate-buffered saline (PBS) +0.2% bovine serum albumin (Sigma Chemical Company). Spleens were then homogenized and splenocytes were re-suspended in RPMI 1640 tissue culture medium (Life Technologies, Grand Island, N.Y.) supplemented with 2% normal mouse serum (Cedarlane Laboratories, Ontario, Canada), penicillin-streptomycin solution (final concentration of 1000 U/ml and 1 mg/ml respectively; Sigma Chemical Company), and $5\times10^{-5}$ M β-mercaptoethanol (Sigma Chemical Company).

BALB/c mice (n=10/group) were immunized with 1 µg hepatitis B surface antigen (HBsAg) sub type ad (International Enzymes, CA) alone or in combination with 1-100 µg CpG ODN 2006, 608, 611, 618 or CpG ODN 620. Animals were bled and boosted at 4 weeks post-primary immunization. At 2 weeks post boost, 5 animals from each group were euthanized and spleens removed for CTL assays.

Antibodies (total IgG, IgG1 and IgG2a) specific to HBsAg (anti-HBs) were detected and quantified by endpoint dilution ELISA assay, which was performed in triplicate on samples from individual animals. End-point titers were defined as the highest plasma dilution that resulted in an absorbance value (OD 450) two times greater than that of non-immune plasma with a cut-off value of 0.05. These were reported as group mean titers (GMT)±SEM.

CTL assays were conducted according to standard manner. Briefly, spleens were removed at 4 weeks post immunization and homogenized into single-cell suspension in RPMI 1640 tissue culture medium (Life Technologies, Grand Island, N.Y.) supplemented with 10% fetal bovine serum (Life Technologies), penicillin-streptomycin solution (final concentration of 1000 U/ml and 1 mg/ml respectively; Sigma, Irvine, UK), and $5\times10^{-5}$ M β-mercaptoethanol (Sigma) (Complete RPMI 1640). HBsAg-specific lymphocytes in splenocyte suspensions ($3\times10^6$ cells/ml) were re-stimulated for 5 days by incubating with a murine cell line (p815-S) expressing HBsAg. Following re-stimulation, the potential of the lymphocytes to kill cells expressing HBsAg was determined by using $^{51}$Cr release assay. The results are presented as % specific lysis at different effector:target (E:T) ratios.

Figure 4:
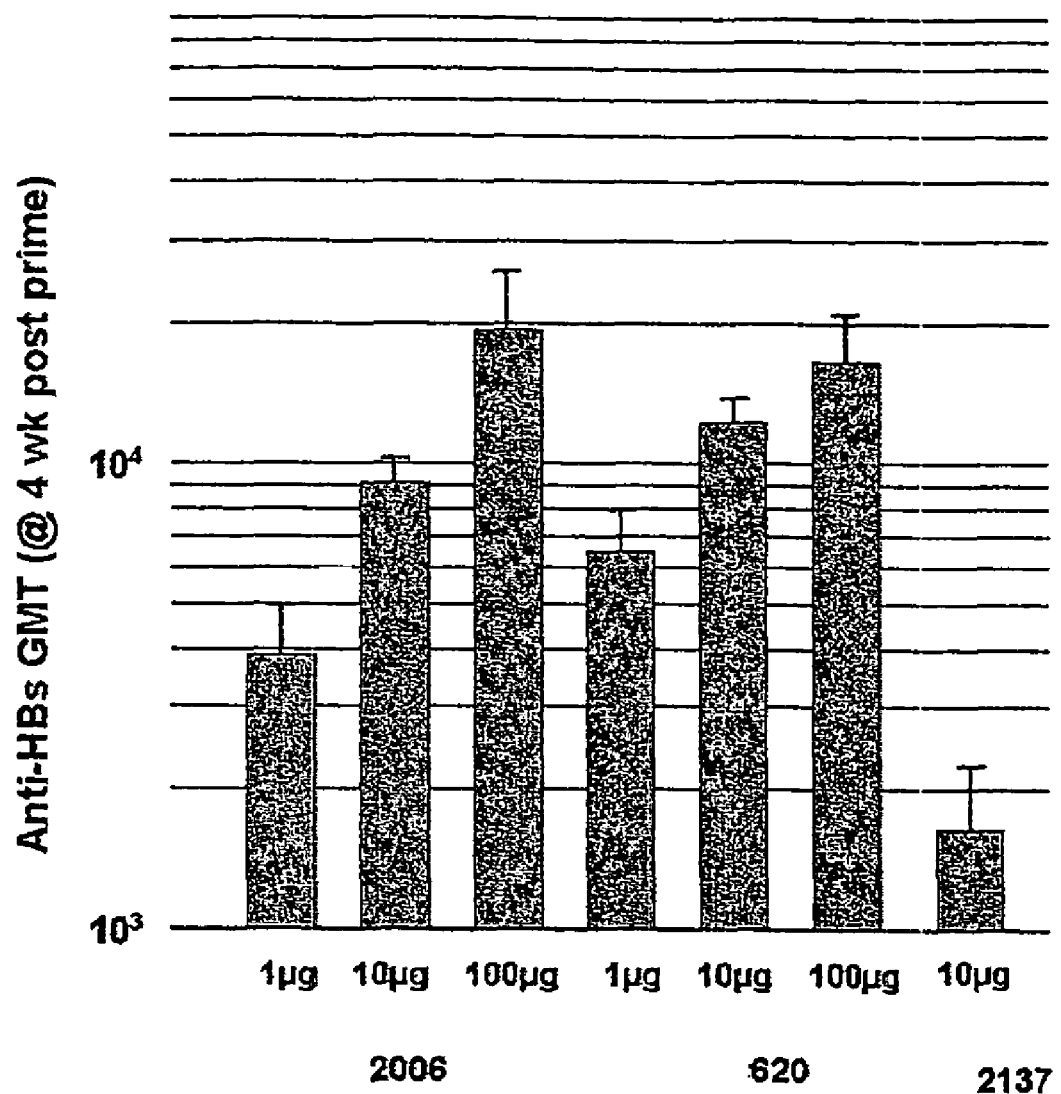
FIG. 4 is a graph depicting group mean titers (GMT) of antigen-specific total IgG following immunization with 1 μg hepatitis B surface antigen (HBsAg) with the indicated amount of ODN.
Figure 5:
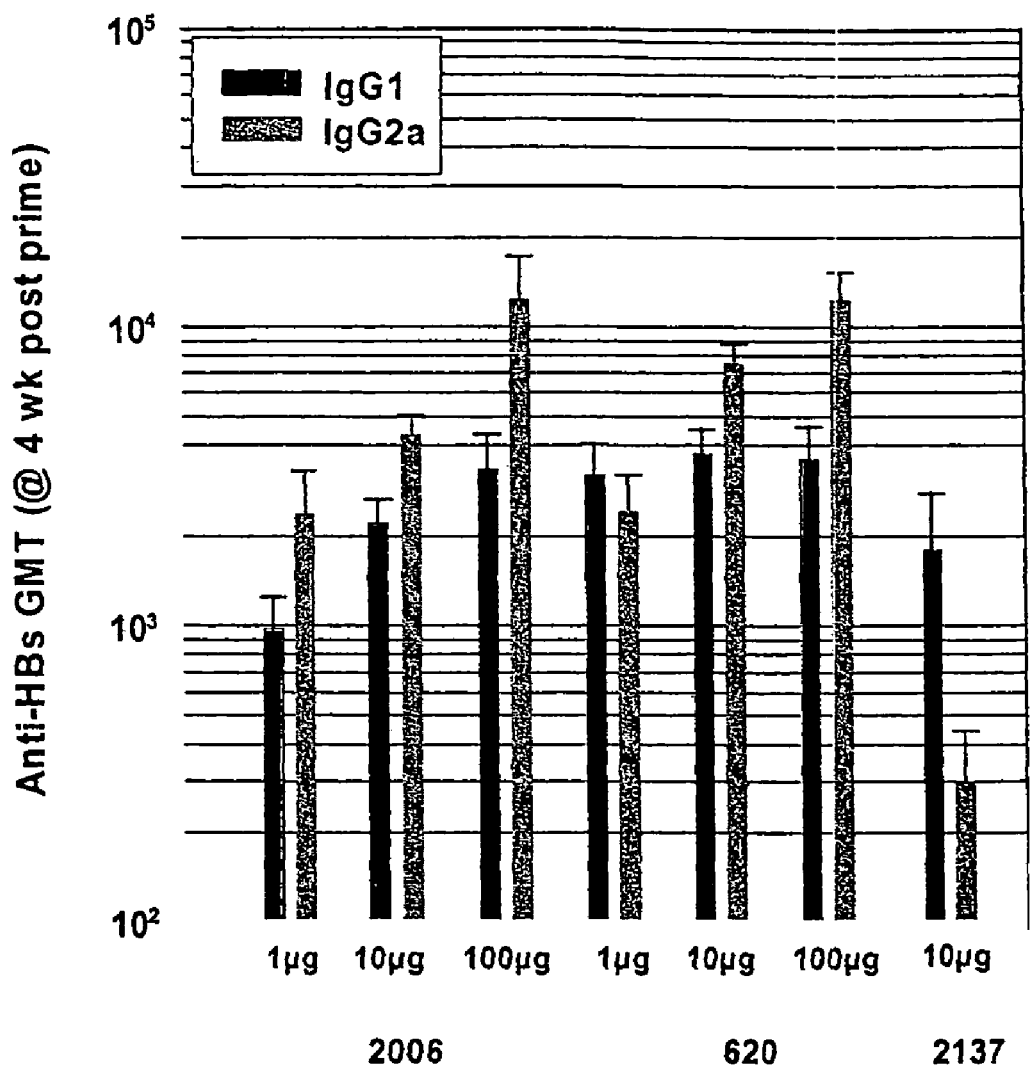
FIG. 5 is a a graph depicting GMT of antigen-specific individual IgG isotypes following immunization with 1 μg HBsAg with the indicated amount of ODN.
Figure 6:
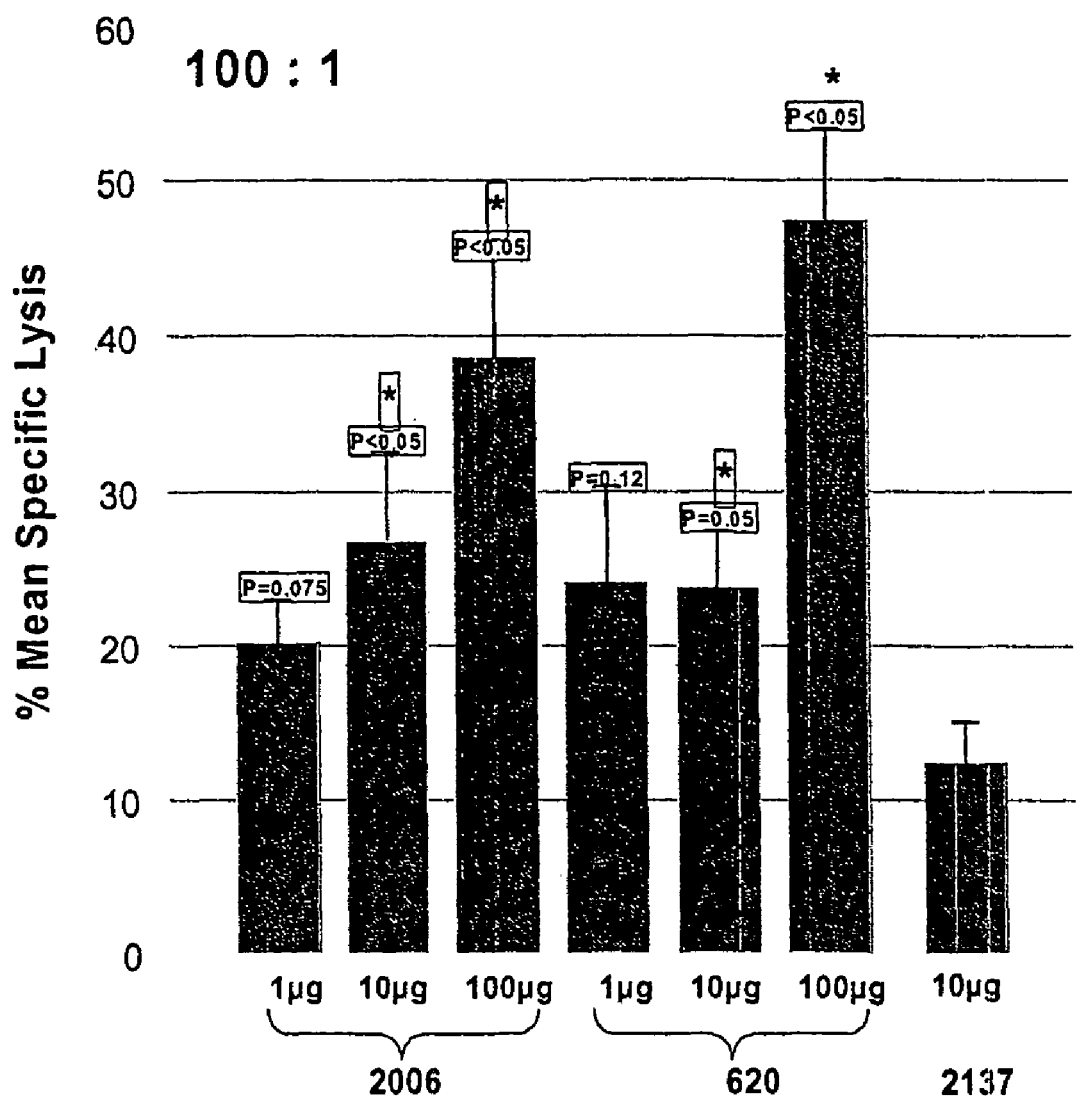
FIG. 6 is a graph depicting antigen-specific cytolytic T lymphocyte responses following immunization with 1 μg HBsAg with the indicated amount of ODN.

Results. Representative results are shown in FIG. 4-6. As shown in FIG. 4, total IgG titers for ODN 2006 and ODN 620 were dose-dependent and found to be ca. $5\times10^3$ and $6.5\times10^3$, respectively, at ODN dose of 1 µg. Total IgG titers for ODN 2006 and ODN 620 were found to be ca. $1\times10^4$ at ODN dose of 100 µg. As shown in FIG. 5, ODN 2006 and ODN 620 both significantly boosted IgG2a (Th1-like IgG in mice) compared to non-CpG control ODN 2137 (TGCTGCTTTTGT-GCTTTTGTGCTT; SEQ ID NO:60). Specifically, IgG2a titers for ODN 2006, 620, and 2137, each administered in doses of 10 µg, were ca. $3\times10^3$, $6\times10^3$, and $3\times10^2$, respectively. As shown in FIG. 6, CTL activity at an E:T ratio of 100:1 for ODN 2006 and 620 was significantly greater than control at administered doses of 10 and 100 µg. For example, percent specific lysis for ODN 2006, 260, and 2137, each administered in a dose of 10 µg, was ca. 26%, 24%, and 12%.

Taken together, the results of these experiments demonstrate that C-Class ODN analogs of the invention effectively induce antigen-specific immune responses in vivo.

Example 5

C-Class ODN Analogs Improve Survival and Reduce Tumor Volume In a Tumor Model In Vivo In this series of experiments, C-class ODN analogs of the invention were tested in vivo in a murine neuroblastoma model. C-class ODN analogs of the invention were found to improve dramatically both overall survival and tumor burden.

ODN were obtained as in Example 1.

BALB/c mice were obtained as in Example 4.

BALB/c mice were injected subcutaneously (s.c.) into the left flank on day 0 with $1\times10^6$ neuroblastoma (Neuro-2a) cells (e.g., ATCC CCL-131, American Type Culture Collection, Manassas, Va.). Mice were given s.c. injections of PBS, CpG 2006, CpG 620, or non-CpG control ODN 2137 daily from day 10-25. Percent survival and tumor volume were measured.

Results. Representative results are shown in FIG. 7. As shown in FIG. 7A, mice treated with 100 µg ODN 620 had a 50% survival rate at 80 days, as compared with corresponding survival rates of 0-20% for ODN 2006, ODN 2137, or PBS. Furthermore, as shown in FIG. 7B, mice treated with 100 µg ODN 620 had a tumor volume that peaked at about 1000 mm$^3$ on day 28 and declined to 0 mm$^3$ by 38 days. By comparison, mice treated with ODN 2137 or PBS had more rapid, monotonic tumor growth.

Taken together, the results of these experiments demonstrate that C-Class ODN analogs of the invention effectively improve survival and reduce tumor volume in a tumor model in vivo.

Example 6

Tissue Metabolism and Distribution of C-Class ODN Analogs

Adsorption/distribution studies with C-class ODN analogs of the invention showed favorable metabolism and clearance from organs such as the kidney and liver after subcutaneous treatment of mice.

Mice were divided into groups of 5 and each mouse was administered 250 µg of ODN in a single subcutaneous dose on day 0. At various time points, the organs (liver, kidneys and spleen) were been removed and the oligonucleotide and its metabolites were extracted for quantification of content.

Results. The ODNs of this invention (e.g., 611 and 620) showed less accumulation in organs as compared to the known fully phosphorothioate palindromic ODNs, such as 2429. For example, on day 3, kidney levels of ODN 611, 620, and 2429 were ca. 70±28, 30±18, and 90±10 mg/kg, respectively. Likewise on day 3, liver levels of ODN 611, 620, and 2429 were ca. 45±15, 28±12, and 150±15 mg/kg, respectively.

Taken as a whole, these results demonstrate that C-class ODN analogs of the invention have favorable metabolism and clearance from organs where ODN might otherwise accumulate.

Example 7

Physical Characteristics of C-Class ODN Analogs

In this set of experiments ODN 2429, 611, 620, 608 (T*C*G*T*C_G*T*T*T*T*C_G*G*C_G*C*G*C_G* C*C*G; SEQ ID NO:51), and 618 (T*C*G* T*C_G*T*T*T*T*C_G*G*C*G*G*C*C_G*C*C*G; SEQ ID NO:53) were characterized using size exclusion chromatography, capillary gel electrophoresis (CGE), UV thermal denaturation, and high pressure liquid chromatography (HPLC). When ODN 611 and ODN 620 were investigated by size exclusion chromatography (225 µM in PBS), only one peak was observed for each compound, i.e., each oligonucleotide eluted like a monomer. In contrast, when ODN 608 and 618 (each containing palindromic sequence) were investigated by size exclusion chromatography, two peaks were observed for each oligonucleotide, consistent with the presence of an intermolecular dimer in addition to the monomer. However, UV thermal denaturation studies indicated that ODN 611 and ODN 620 had a secondary structure in solution, consistent with an intramolecular hairpin structure. The hairpin structure is believed to result from the inverted repeat in the 611 and 620 sequences. Generally sharper peaks were observed in HPLC and CGE for these sequences as compared to ODN 2429 and ODN 608.

Taken as a whole, these results demonstrate that C-class ODN analogs of the invention tend to form intramolecular secondary structures and do not form intermolecular complexes in vitro at the concentration examined, whereas palindrome-containing C-class ODN tend to associate into complexes through intermolecular interactions. In vivo, however, it is likely that concentrations of ODN attained in the intraendosomal compartment are sufficiently high to favor duplex or even higher-order complexes of ODN, including duplex or even higher-order complexes of C-class ODN analogs of the invention.

EQUIVALENTS

The foregoing written specification is considered to be sufficient to enable one skilled in the art to practice the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents, and patent publications cited herein are incorporated in their entirety herein by reference.

We claim:

1. An immunostimulatory nucleic acid molecule of Formula I $$Z_1[(X_1Y_1R_1)\ N\ (X_2Y_2R_2)_k Z_2]_p\ (S_1)_q\ N'\ (N_n)\ldots(N_2)$$
$$(N_1)\ S_2\ (N_{1\#})(N_{2\#})\ldots(N_{n\#})\ Z_3 \quad \text{(Formula I)}$$

wherein each of $Z_1$, $Z_2$, and $Z_3$ is independently any sequence 0 to 12 nucleotides long and wherein $Z_3$ is fewer than 3 nucletides each of $X_1$ and $X_2$ is independently a nucleotide containing thymine, uracil, adenine, or a 5-substituted uracil;

each of $Y_1$ and $Y_2$ is independently a cytosine (C) or a modified cytosine;

each of $R_1$ and $R_2$ is independently a guanine (G) or a modified guanine;

each of N and N' is independently any sequence 0 to 12 nucleotides long which optionally comprises a non-nucleotidic linker or abasic dSpacer;

$S_1$ is a non-nucleotidic linker, an abasic linker (dSpacers), triethylene glycol units or hexaethylene glycol units, which optionally provides for 2'5'-, 5'5'-, 3'3'-, 2'2'-, or 2'3'-internucleoside linkages;

$S_2$ is any non-palindromic sequence 1 to 10 nucleotides long or a non-nucleotidic linker, an abasic linker (dSpacers), triethylene glycol units or hexaethylene glycol units;

each of $N_n, \ldots N_2, N_1$, and $N_{1\#}, N_{2\#}, \ldots N_{n\#}$ is any nucleotide or modified nucleotide wherein $N_1$ base-pairs with $N_{1\#}$, $N_2$ base-pairs with $N_{2\#}$, ... and $N_n$ base-pairs with $N_{n\#}$; such that $(N_n)\ldots(N_2)(N_1)\ S_2\ (N_{1\#})(N_{2\#})\ldots(N_{n\#})$ forms an inverted repeat capable of forming a hairpin stem-loop structure having a stem of at least 4 consecutive base pairs long, k is an integer from 0 to 5;

n is an integer from 2 to 16;

p is an integer from 1 to 6; and q is an integer from 0 to 10, and wherein when $(N_n)\ldots(N_2)(N_1)\ S_2\ (N_{1\#})(N_{2\#})\ldots(N_{n\#})$ is 10 to 42 nucleotides long, $S_2$ is 6 to 10 nucleotides long or is a non-nucleotidic linker, an abasic linker (dSpacers), triethylene glycol units or hexaethylene glycol units, and/or $(N_n)\ldots(N_2)(N_1)\ S_2\ (N_{1\#})(N_{2\#})\ldots(N_{n\#})$ has a GC content that is less than ⅔'.

2. The immunostimulatory nucleic acid molecule of claim 1, wherein each of $N_n, \ldots N_2, N_1$, and $N_{1\#}, N_{2\#}, \ldots N_{n\#}$ is chosen from C, G, or modifications thereof, and wherein C base-pairs with G.

3. The immunostimulatory nucleic acid molecule of claim 1, wherein each of $N_n, \ldots N_2, N_1$, and $N_{1\#}, N_{2\#}, \ldots N_{n\#}$ is chosen from T, A, or modifications thereof, and wherein T base-pairs with A.

4. The immunostimulatory nucleic acid molecule of claim 1, wherein each of $N_n, \ldots N_2, N_1$, and $N_{1\#}, N_{2\#}, \ldots N_{n\#}$ is chosen from C, T, A, G, or modifications thereof.

5. The immunostimulatory nucleic acid molecule of claim 1, wherein each of $N_n, \ldots N_2, N_1$, and $N_{1\#}, N_{2\#}, \ldots N_{n\#}$ is chosen from unmodified or modified nucleotides which form Watson-Crick base pairs.

6. The immunostimulatory nucleic acid molecule of claim 1, wherein at least one of each of $N_n, \ldots N_2, N_1$, and $N_{1\#}, N_{2\#}, \ldots N_{n\#}$ is chosen from unmodified or modified nucleotides which form non-Watson-Crick base pairs.

7. The immunostimulatory nucleic acid molecule of claim 1, wherein each of $Y_1R_1$ and $Y_2R_2$ have an internucleotide linkage that is a phosphodiester bond.

8. The immunostimulatory nucleic acid molecule of claim 7, wherein all other internucleotide linkages of the nucleic acid are stabilized internucleotide linkages.

9. The immunostimulatory nucleic acid molecule of claim 1, wherein internucleotide linkages of the oligonucleotide are all phosphorothioate linkages.

10. The immunostimulatory nucleic acid molecule of claim 1, wherein $Y_1$ is C.

11. The immunostimulatory nucleic acid molecule of claim 1, wherein $R_1$ is G.

12. The immunostimulatory nucleic acid molecule of claim 1, wherein $Y_1$ is C and $R_1$ is G.

13. The immunostimulatory nucleic acid molecule of claim 1 wherein $X_1$ or $X_2$ is T.

14. The immunostimulatory nucleic acid molecule of claim 1, wherein $X_1$ is T, $X_2$ is T, $Y_1$ is C, $R_1$ is G, and k is 1.

15. The immunostimulatory nucleic acid molecule of claim 1, wherein $X_1$ is T, $X_2$ is T, $Y_1$ is C, $R_1$ is G, k is 1, p is 1, N and N' and $Z_3$ each contain zero nucleotides, and $Z_2$ is TTTT or d(UUUU).

16. The immunostimulatory nucleic acid molecule of claim 1, wherein $S_2$ is a non-nucleotidic linker.

17. The immunostimulatory nucleic acid molecule of claim 1, wherein $S_2$ contains at least one abasic dSpacer residue.

18. The immunostimulatory nucleic acid molecule of claim 1, wherein $S_1$ is a doubler unit or a trebler unit.

19. The immunostimulatory nucleic acid molecule of claim 1, wherein the oligonucleotide comprises at least one 2'5'-, 5'5'-, 3'3'-, 2'2'-, or 2'3'-internucleoside linkage.

20. An immunostimulatory nucleic acid molecule of Formula III $$(Z')_m Z_3 \quad \text{(Formula III)}$$

wherein $Z'$ is $Z_1\ [(X_1Y_1R_1)\ N\ (X_2Y_2R_2)_k\ Z_2]_p\ (S_1)_q\ N'\ (N_n)\ldots(N_3)(N_2)(N_1)\ S_2\ (N_{1\#})(N_{2\#})(N_{3\#})\ldots(N_{n\#})$;

each of $Z_1$, $Z_2$, and $Z_3$ is independently any sequence 0 to 12 nucleotides long which optionally comprises a non-nucleotidic linker or abasic dSpacer;

each of $X_1$ and $X_2$ is independently a nucleotide containing thymine, uracil, adenine, or a 5-substituted uracil;

each of $Y_1$ and $Y_2$ is independently a cytosine or a modified cytosine;

each of $R_1$ and $R_2$ is independently a guanine or a modified guanine;

each of N and N' is independently any sequence 0 to 12 nucleotides long which optionally comprises a non-nucleotidic linker or abasic dSpacer;

$S_1$ is a non-nucleotidic linker, an abasic linker (dSpacers), triethylene glycol units or hexaethylene glycol units, which optionally provides for 2'5'-, 5'5'-, 3'3'-, 2'2'-, or 2'3'-internucleoside linkages;

$S_2$ is any non-palindromic sequence 1 to 10 nucleotides long or a non-nucleotidic linker, an abasic linker (dSpacers), triethylene glycol units or hexaethylene glycol units;

wherein the linkage of Z' to Z' is defined by $S_3$ and $S_3$ is a direct or indirect 2'5'-, 5'5'-, 3'3'-, 2'2'-, or 2'3'-internucleoside linkage, or a non-nucleotidic linker, said non-nucleotidic linker comprising abasic linkers (dSpacers), triethylene glycol units, or hexaethylene glycol units facilitating a 2'5'-, 5'5'-, 3'3'-, 2'2'-, or 2'3'-linkage of m sequence parts;

each of $N_n, \ldots N_3, N_2, N_1,$ and $N_{1\#}, N_{2\#}, N_{3\#} \ldots N_{n\#}$ is any nucleotide or modified nucleotide wherein $N_1$ base-pairs with $N_{1\#}$, $N_2$ base-pairs with $N_2\#$, $N_3$ base-pairs with $N_{3\#}, \ldots$ and $N_n$ base-pairs with $N_{n\#}$;

k is an integer from 0 to 5;
m is an integer from 2 to 10;
n is an integer from 2 to 16;
p is an integer from 1 to 6; and
q is an integer from 0 to 10.

21. An immunostimulatory nucleic acid molecule of claim 1, wherein $Z_1 [(X_1Y_1R_1) N (X_2Y_2R_2)_k Z_2]_p (S_1)_q$ is a non-palindromic sequence.

22. An immunostimulatory nucleic acid molecule of claim 1, wherein $Z_1 [(X_1Y_1R_1) N (X_2Y_2R_2)_k Z_2]_p (S_1)_q$ is TCGTCGTTTT (SEQ ID NO:40), TCGTCGTTLL, TCGA, TCGAC, TCGACGTC, or TCGACGTCG, wherein L is dSpacer.

23. An immunostimulatory nucleic acid molecule of claim 1, wherein $Z_1 [(X_1Y_1R_1) N (X_2Y_2R_2)_k Z_2]_p (S_1)_q$ is a palindromic sequence.

24. The immunostimulatory nucleic acid molecule of claim 1, wherein $Z_1 [(X_1Y_1R_1) N (X_2Y_2R_2)_k Z_2]_p (S_1)_q$ is TCGACGTCGA (SEQ ID NO:19) or TCGTCGACGA (SEQ ID NO:34).

25. The immunostimulatory nucleic acid molecule of claim 1, wherein $Z_1 [(X_1Y_1R_1) N (X_2Y_2R_2)_k Z_2]_p (S_1)_q$ is TCGCGACGTT (SEQ ID NO:26) or TCGCGTCGTT (SEQ ID NO:69).

26. The immunostimulatory nucleic acid molecule of claim 1, wherein $(N_n)\ldots(N_2)(N_1) S_2 (N_{1\#})(N_{2\#})\ldots(N_n) Z_3$ comprises a sequence

| | |
|---|---|
| AGCGAAGCT, | |
| CAATATTTATTG, | (SEQ ID NO: 1) |
| CCGTTTTGTGG, | (SEQ ID NO: 2) |
| CGGCGCCGTGCCG, | (SEQ ID NO: 19) |
| CGGCGCCGTTGCCG, | (SEQ ID NO: 34) |
| CGGCGLLCGCCG, | (SEQ ID NO: 5) |
| CGGCGLLLTGCCG, | (SEQ ID NO: 6) |
| CGGCGGLLCCGCCG, | (SEQ ID NO: 7) |
| CGGCGTCGCCGCCG, | (SEQ ID NO: 8) |

-continued

| | |
|---|---|
| CGTCGACGGGACGGG, | (SEQ ID NO: 10) |
| CGTCGACGTGACGGG, | (SEQ ID NO: 11) |
| GAGAGTTGGGCTCTC, | (SEQ ID NO: 12) |
| GTCGAGGAGGT, | (SEQ ID NO: 14) |
| TAATALLTATTA, | (SEQ ID NO: 15) |
| TAATATCCATTA, or | (SEQ ID NO: 16) |
| TAATATTTATTA, | (SEQ ID NO: 17) | wherein L is dSpacer.

27. The immunostimulatory nucleic acid molecule of claim 1, wherein $(N_n)\ldots(N_2)(N_1) S_2 (N_{1\#})(N_{2\#})\ldots(N_{n\#})$ comprises a sequence GGCGCGCTGCCG (SEQ ID NO:13).

28. The immunostimulatory nucleic acid molecule of claim 1, comprising a sequence

| | |
|---|---|
| TCGACGTCGACCGTTTTGTGG, | (SEQ ID NO: 20) |
| TCGACGTCGACGGGACGGG, | (SEQ ID NO: 21) |
| TCGACGTCGACGTGACGGG, | (SEQ ID NO: 22) |
| TCGACGTCGAGAGTTGGGCTCTC, | (SEQ ID NO: 23) |
| TCGACGTCGAGCGAAGCT, or | (SEQ ID NO: 24) |
| TCGACGTCGAGGAGGT | (SEQ ID NO: 25). |

29. An immunostimulatory nucleic acid molecule of Formula I $$Z_1[(X_1Y_1R_1) N (X_2Y_2R_2)_k Z_2]_p (S_1)_q N' (N_n) \ldots (N_2) (N_1) S_2 (N_{1\#})(N_{2\#}) \ldots (N_{n\#}) Z_3 \quad \text{(Formula I)}$$

wherein
each of $Z_1, Z_2,$ and $Z_3$ is independently any sequence 0 to 12 nucleotides long which optionally comprises a non-nucleotidic linker or abasic dSpacer;

each of $X_1$ and $X_2$ is independently a nucleotide containing thymine, uracil, adenine, or a 5-substituted uracil;

each of $Y_1$ and $Y_2$ is independently a cytosine (C) or a modified cytosine;

each of $R_1$ and $R_2$ is independently a guanine (G) or a modified guanine;

each of N and N' is independently any sequence 0 to 12 nucleotides long which optionally comprises a non-nucleotidic linker or abasic dSpacer;

$S_1$ is a non-nucleotidic linker, an abasic linker (dSpacers), triethylene glycol units or hexaethylene glycol units, which optionally provides for 2'5'-, 5'5'-, 3'3'-, 2'2'-, or 2'3'-internucleoside linkages;

$S_2$ is any non-palindromic sequence 1 to 10 nucleotides long or a non-nucleotidic linker, an abasic linker (dSpacers), triethylene glycol units or hexaethylene glycol units;

each of $N_n, N_2, \ldots N_1,$ and $N_{1\#}, N_{2\#}, \ldots N_{n\#}$ is any nucleotide or modified nucleotide wherein $N_1$ base-pairs with $N_{1\#}$, $N_2$ base-pairs with $N_{2\#}, \ldots$ and $N_n$ base-pairs with $N_{n\#}$;

k is an integer from 0 to 5;
n is an integer from 2 to 16;
p is an integer from 1 to 6; and
q is an integer from 0 to 10, and wherein when $(N_n) \ldots (N_2)(N_1) S_2 (N_{1\#})(N_{2\#}) \ldots (N_{n\#})$ is 10 to 42 nucleotides long, $S_2$ is 4 to 10 nucleotides long, or is a non-nucleotidic linker, an abasic linker (dSpacers), triethylene glycol units or hexaethylene glycol units, wherein the immunostimulatory nuclecic acid molecule comprises a sequence:

| | |
|---|---|
| TCGTCGTTLLACGGCGCCGTGCCG, | (SEQ ID NO: 37) |
| TCGTCGTTLLACGGCGLLLTGCCG, | (SEQ ID NO: 38) |
| TCGTCGTTLLCGGCGCGGCGCCG, | (SEQ ID NO: 39) |
| TCGTCGTTTTACGGCGCCGTTGCCG, | (SEQ ID NO: 44) |
| TCGTCGTTTTACGGCGLLLTGCCG, | (SEQ ID NO: 45) |
| TCGTCGTTTTACGGCGTTTTGCCG, | (SEQ ID NO: 49) |
| TCGTCGTTTTCAATATTTATTG, | (SEQ ID NO: 50) |
| TCGTCGTTTTCGGCGLLCGCCG, | (SEQ ID NO: 52) |
| TCGTCGTTTTCGGCGGLLCCGCCG, | (SEQ ID NO: 54) |
| TCGTCGTTTTCGGCGTCGCCGCCG, | (SEQ ID NO: 55) |
| TCGTCGTTTTTAATALLLTATTA, | (SEQ ID NO: 57) |
| TCGTCGTTTTTAATATCCATTA, or | (SEQ ID NO: 58) |
| TCGTCGTTTTTAATATTTATTA, | (SEQ ID NO: 59) | wherein L is dSpacer.

30. The immunostimulatory nucleic acid molecule of claim 1, comprising a sequence TCGCGTCGTTCGGCGCGCTGCCG (SEQ ID NO:30).

31. The immunostimulatory nucleic acid molecule of claim 1, comprising a sequence TCGCGACGTTCGGCGCGCTGCCG (SEQ ID NO:27).

32. An immunostimulatory nucleic acid molecule of Formula I $$Z_1[(X_1Y_1R_1) N (X_2Y_2R_2)_k Z_2]_p (S_1)_q N' (N_n) \ldots (N_2) (N_1) S_2 (N_{1\#})(N_{2\#}) \ldots (N_{n\#}) Z_3 \quad \text{(Formula I)}$$

wherein
- each of $Z_1$, $Z_2$, and $Z_3$ is independently any sequence 0 to 12 nucleotides long which optionally comprises a non-nucleotidic linker or abasic dSpacer;
- each of $X_1$ and $X_2$ is independently a nucleotide containing thymine, uracil, adenine, or a 5-substituted uracil;
- each of $Y_1$ and $Y_2$ is independently a cytosine (C) or a modified cytosine;
- each of $R_1$ and $R_2$ is independently a guanine (G) or a modified guanine;
- each of N and N' is independently any sequence 0 to 12 nucleotides long which optionally comprises a non-nucleotidic linker or abasic dSpacer;
- $S_1$ is a non-nucleotidic linker, an abasic linker (dSpacers), triethylene glycol units or hexaethylene glycol units, which optionally provides for 2'5'-, 5'5'-, 3'3'-, 2'2'-, or 2'3'-internucleoside linkages;
- $S_2$ is any non-palindromic sequence 1 to 10 nucleotides long or a non-nucleotidic linker, an abasic linker (dSpacers), triethylene glycol units or hexaethylene glycol units;
- each of $N_n, \ldots N_2, N_1$, and $N_{1\#}, N_{2\#}, \ldots N_{n\#}$ is any nucleotide or modified nucleotide wherein $N_1$ base-pairs with $N_{1\#}$, $N_2$ base-pairs with $N_{2\#}$, ... and $N_n$ base-pairs with $N_{n\#}$;
- k is an integer from 0 to 5;
- n is an integer from 2 to 16;
- p is an integer from 1 to 6; and
- q is an integer from 0 to 10, and wherein when $(N_n) \ldots (N_2)(N_1) S_2 (N_{1\#})(N_{2\#}) \ldots (N_{n\#})$ is 10 to 42 nucleotides long, $S_2$ is 4 to 10 nucleotides long, or is a non-nucleotidic linker, an abasic linker (dSpacers), triethylene glycol units or hexaethylene glycol units, and/or $(N_n) \ldots (N_2)(N_1) S_2 (N_{1\#})(N_{2\#}) \ldots (N_{n\#})$ has a GC content that is less than ⅔, wherein the immunostimulatory nuclecic acid molecule comprises a sequence chosen from:

| | |
|---|---|
| T*C*G*T*C*G*T*T*T*T*A*C*G*A*C*G*C*C*G*T*G*C*C*G, | (SEQ ID NO: 42) |
| T*C*G*T*C*G*C*T*T*T*G*C*G*A*C*G*C*C*G*T*G*C*C*G, | (SEQ ID NO: 36) |
| T*C*G*T*C*G*C*C*C*G*C*G*A*C*G*C*C*G*T*G*C*C*G, | (SEQ ID NO: 35) |
| T*C*G*T*C*G*T*T*T*T*A*C*G*G*C*G*C*C*G*T*T*G*C*C*G, | (SEQ ID NO: 44) |
| T*C*G*T*C*G*T*T*L*L*A*C*G*G*C*G*C*C*G*T*G*C*C*G, | (SEQ ID NO: 37) |
| T*C*G*T*C*G*T*T*T*T*A*C*G*G*C*G*L*L*L*T*G*C*C*G, | (SEQ ID NO: 45) |
| T*C*G*T*C*G*T*T*L*L*A*C*G*G*C*G*L*L*L*T*G*C*C*G, | (SEQ ID NO: 38) |
| T*C*G*T*C*G*T*T*T*T*C*G*G*C*G*G*L*L*C*C*G*C*C*G, | (SEQ ID NO: 54) |
| T*C*G*T*C*G*T*T*T*T*C*G*G*C*G*T*C*G*C*C*G*C*C*G, | (SEQ ID NO: 55) |
| T*C*G*T*C*G*T*T*L*L*C*G*G*C*G*C*G*G*C*G*C*C*G, | (SEQ ID NO: 39) |
| T*C*G*T*C*G*T*T*T*T*C*G*G*C*G*L*L*C*G*C*C*G, | (SEQ ID NO: 52) |
| T*C*G*T*C*G*T*T*T*T*T*A*A*T*A*T*T*T*A*T*T*A, | (SEQ ID NO: 59) |
| T*C*G*T*C_G*T*T*T*T*T*A*A*T*A*T*T*T*A*T*T*A, | (SEQ ID NO: 59) |
| T*C*G*T*C_G*T*T*T*T*C*A*A*T*A*T*T*T*A*T*T*G, | (SEQ ID NO: 50) |
| T*C*G*T*C_G*T*T*T*T*T*A*A*T*A*T*C*C*A*T*T*A, | (SEQ ID NO: 58) |
| T*C*G*T*C*G*T*T*T*T*T*A*A*T*A*L*L*T*A*T*T*A, | (SEQ ID NO: 57) |
| T*C*G*T*C_G*T*T*T*T*A*C*G*G*C*G*L*L*L*T*G*C*C*G, | (SEQ ID NO: 45) |
| T*C*G*T*C_G*T*T*L*L*A*C*G*G*C*G*L*L*L*T*G*C*C*G, and | (SEQ ID NO: 38) |
| T*C*G*T*C_G*T*T*T*T*C*G*G*C*G*G*L*L*C*C*G*C*C*G, | (SEQ ID NO: 54) | wherein L is dSpacer, * is phosphorothioate, and _ is phosphodiester.

33. The immunostimulatory nucleic acid molecule of claim 1, comprising a sequence chosen from

T*C*G*A*C*G*T*C*G_A_C*G*G*G*A*C*G*G*G,  (SEQ ID NO: 21)

T*C*G*A*C*G*T*C*G_A_C*G*T*G*A*C*G*G*G,  (SEQ ID NO: 22)

T*C*G*A*C*G*T*C*G*A*C*G*G*G*A*C*G*G*G,  (SEQ ID NO: 21)

T*C*G*A*C*G*T*C*G*A*G*G*A*G*G*T,  (SEQ ID NO: 25)

T*C*G*A*C*G*T*C*G*A*G*C*G*A*A*G*C*T,  (SEQ ID NO: 24)

T*C*G*A*C*G*T*C*G*A*C*C*G*T*T*T*T*G*T*G*G, and  (SEQ ID NO: 20)

T*C*G*A*C*G*T*C*G*A*G*A*G*T*T*G*G*G*C*T*C*T*C,  (SEQ ID NO: 23)

wherein * is phosphorothioate and _ is phosphodiester.

34. The immunostimulatory nucleic acid molecule of claim 1, comprising a sequence chosen from

T*C*G*A*C*G*T*C*G*A*C*G*T*G*A*C*G*T*G,  (SEQ ID NO: 62)

T*C*G*A*C*G*T*C*G*A*C*G*T*G*A*C*G,  (SEQ ID NO: 61)

T*C_G*T*C_G*A*C_G*T*T*C_G*G*C*G*C*C_G*T*G*C*C*G,  (SEQ ID NO: 65)

T*C*G*T*C_G*T*A*C_G*G*C*G*C*C_G*T*G*C*C*G,  (SEQ ID NO: 66)

T*C*G*T*C_G*T*T*A*C_G*G*C*G*C*C_G*T*G*C*C*G,  (SEQ ID NO: 67)

T*C*G*A*C*G*T*C*G*A*C*G*T*G*A*C*G*T*T,  (SEQ ID NO: 63)

T*C*G*T*C_G*A*C_G*A*T*C_G*G*C*G*C*C_G*T*G*C*C*G,  (SEQ ID NO: 64)

T*C*G*T*C*G*A*C*G*A_T_C*G*G*C*G*C*C*G*T*G*C*C*G,  (SEQ ID NO: 64)

T*C*G*A*C_G*T*C*G*A*C_G*T*G*A*C*G*T*T,  (SEQ ID NO: 63)

T*C*G*A*C_G*T*C*G*A*C*G*T_G*A*C*G*T*T, and  (SEQ ID NO: 63)

T*C*G*T*C_G*T*T*T*A*C_G*G*C*G*C*C_G*T*G*C*C*G*T,  (SEQ ID NO: 68)

wherein * is phosphorothioate and _ is phosphodiester.

35. The immunostimulatory nucleic acid molecule of claim 1, comprising a sequence chosen from

T*C*G*C_G*T*C*G*T*T*C_G*G*C*G*C_G*C*T*G*C*C*G,  (SEQ ID NO: 30)

T*C*G_C*G*T*C*G*T*T*C_G*G*C*G*C_G*C*T*G*C*C*G, and  (SEQ ID NO: 30)

T*C*G*C*G_T*C*G*T*T*C_G*G*C*G*C_G*C*T*G*C*C*G,  (SEQ ID NO: 30)

wherein * is phosphorothioate and _ is phosphodiester.

36. The immunostimulatory nucleic acid molecule of claim 1, comprising a sequence T*C*G*C_G*A*C*G*T*T*C_G*G*C*G*C_G*C*T*G*C*C*G (SEQ ID NO:27), wherein * is phosphorothioate and _ is phosphodiester.

37. The immunostimulatory nucleic acid molecule of claim 1, comprising a sequence chosen from

T*C_G*T*C*G*T*T*T*T*A*C*G*G*C*G*T*C*G*T*G*C*C*G,  (SEQ ID NO: 48)

T*C_G*T*C*G*T*T*T*T*A*C*G*G*C*G*T*C*G*C*G*C*G, and  (SEQ ID NO: 47)

T*C_G*T*C*G*T*T*T*T*A*C*G*G*C*G*T*C*G*C*G,  (SEQ ID NO: 46)

wherein * is phosphorothioate and _ is phosphodiester.

38. The immunostimulatory nucleic acid molecule of claim 1, comprising s a sequence T*C_G*T*C*G*T*T*T*T*A*C*G*G*C*G*T*C*G*T*G*C*C*G (SEQ ID NO:48), wherein * is phosphorothioate and _ is phosphodiester.

39. The immunostimulatory nucleic acid molecule of claim 1, wherein at least one nucleotide in the oligonucleotide is a substituted or modified purine or pyrimidine.

40. The immunostimulatory nucleic acid molecule of claim 39, wherein the substituted pyrimidine is a C5- or C6-substituted pyrimidine.

41. The immunostimulatory nucleic acid molecule of claim 39, wherein the substituted purine is a C8- or C7-substituted purine.

42. The immunostimulatory nucleic acid molecule of claim 39, wherein the substituted or modified purine or pyrimidine is selected from the group consisting of 5-substituted cytosines, 6-substituted cytosines, N4-substituted cytosines, 5-aza-cytosine, 2-mercapto-cytosine, isocytosine, pseudo-isocytosine, cytosine analogs with condensed ring systems, and uracil derivatives, thymine derivatives, 7-deazaguanine, 7-deaza-7-substituted guanine, 7-deaza-8-substituted guanine, 7-deaza-8-aza guanine, hypoxanthine, N2-substituted guanines, 5-amino-3-methyl-3H,6H-thiazolo[4,5-d]pyrimidine-2,7-dione, 2,6-diaminopurine, 2-aminopurine, purine, indole, substituted adenines, 8-substituted guanine, and 6-thioguanine.

43. The immunostimulatory nucleic acid molecule of claim 39, wherein the substituted or modified purine or pyrimidine is selected from the group consisting of 5-methyl-cytosine, 5-fluoro-cytosine, 5-chloro-cytosine, 5-bromo-cytosine, 5-iodo-cytosine, 5-hydroxy-cytosine, 6-hydroxy-cytosine, 5-hydroxymethyl-cytosine, 5-difluoromethyl-cytosine, and unsubstituted or substituted 5-alkynyl-cytosine, N4-ethyl-cytosine, N,N'-propylene cytosine, phenoxazine, 5-fluoro-uracil, 5-bromo-uracil, 5-bromovinyl-uracil, 4-thio-uracil, 5-hydroxy-uracil, 5-propynyl-uracil, 2-thiothymine, 4-thiothymine, 6-substituted thymines, 7-deaza-7-(C2-C6)alkynylguanine, N2-methyl-guanine, N6-methyl-adenine, 8-oxo-adenine, 8-hydroxyguanine, and 8-bromoguanine.

44. The immunostimulatory nucleic acid molecule of claim 39, wherein the substituted or modified purine or pyrimidine is selected from the group consisting of a universal base, an aromatic ring system, an aromatic ring system, and a hydrogen atom (dSpacer).

45. The immunostimulatory nucleic acid molecule of claim 39, wherein the substituted or modified purine or pyrimidine is selected from the group consisting of 4-methyl-indole, 5-nitro-indole, 3-nitropyrrole, P-base, and K-base, benzimidazole, dichloro-benzimidazole, 1-methyl-1H-[1,2,4]triazole-3-carboxylic acid amide, fluorobenzene, and difluorobenzene.

46. The immunostimulatory nucleic acid molecule of claim 1, wherein any of N, S, X, or Z is substituted by a residue selected from the group consisting of C6-C30 alkyl chain, bile acids, cholic acid, taurocholic acid, deoxycholate, cholesterol, oleyl litocholic acid, oleoyl cholenic acid, glycolipids, phospholipids, sphingolipids, isoprenoids, steroids, vitamins, vitamin E, saturated fatty acids, unsaturated fatty acids, fatty acid esters, triglycerides, pyrenes, porphyrins, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes, cyanine dye Cy3, cyanine dye Cy576, Hoechst 33258 dye, psoralen, and ibuprofen.

47. An immunostimulatory nucleic acid molecule comprising
  (a) a 5' end beginning with an immunostimulatory motif chosen from $(TCG)_nN$ and $RDCGY_1Y_2N$, wherein T is thymine, C is unmethylated cytosine, G is guanine, R is a purine, D is not C, each of $Y_1$ and $Y_2$ independently is a pyrimidine, n is an integer between 1 and 4, inclusive, and N is any sequence 0-12 bases long;
  (b) a 3' end terminating in an inverted repeat capable of forming a hairpin or stem-loop structure, said structure comprising
     a GC-rich stem, wherein the GC rich stem includes 5 to 6 consecutive nucleotides selected from G and C and including both C and G nucleotides, and
     at least one unmatched or mismatched base; and
  (c) a partially stabilized backbone comprising at least one phosphodiester 5'-CpG-3' linkage.

48. An immunostimulatory nucleic acid having a base sequence provided as TCGTCGTTTTACGGCGTCGT-GCCG (SEQ ID NO:48).

49. A pharmaceutical composition comprising an immunostimulatory nucleic acid molecule of claim 1 and a pharmaceutically acceptable carrier.

50. An immunostimulatory nucleic acid having a base sequence provided as TCGTCGTTTTACGGCGTCGT-GCCG (SEQ ID NO:43).

* * * * *

UNITED STATES PATENT AND TRADEMARK OFFICE
CERTIFICATE OF CORRECTION

PATENT NO. : 8,188,254 B2  
APPLICATION NO. : 10/978283  
DATED : May 29, 2012  
INVENTOR(S) : Uhlmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 928 days.

Page 1 of 1

Signed and Sealed this
Twenty-eighth Day of August, 2012

David J. Kappos
*Director of the United States Patent and Trademark Office*

SEQUENCE LISTING

```
<160> NUMBER OF SEQ ID NOS: 69

<210> SEQ ID NO 1
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 1
caatatttat tg                                                         12

<210> SEQ ID NO 2
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 2
ccgttttgtg g                                                          11

<210> SEQ ID NO 3
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 3
```

-continued cggcgccgtg ccg                                                               13

<210> SEQ ID NO 4
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 4
cggcgccgtt gccg                                                              14

<210> SEQ ID NO 5
<211> LENGTH: 12
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6)..(7)
<223> OTHER INFORMATION: abasic nucleotide
<220> FEATURE:
<221> NAME/KEY: misc_feature
<222> LOCATION: (6)..(7)
<223> OTHER INFORMATION: n is a, c, g, or t

<400> SEQUENCE: 5
cggcgnncgc cg                                                                12

<210> SEQ ID NO 6
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6)..(8)
<223> OTHER INFORMATION: abasic nucleotide
<220> FEATURE:
<221> NAME/KEY: misc_feature
<222> LOCATION: (6)..(8)
<223> OTHER INFORMATION: n is a, c, g, or t

<400> SEQUENCE: 6
cggcgnnntg ccg                                                               13

<210> SEQ ID NO 7
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: abasic nucleotide
<220> FEATURE:
<221> NAME/KEY: misc_feature
<222> LOCATION: (7)..(8)
<223> OTHER INFORMATION: n is a, c, g, or t

<400> SEQUENCE: 7
cggcggnncc gccg                                                              14

<210> SEQ ID NO 8
<211> LENGTH: 14
<212> TYPE: DNA
<213> ORGANISM: Artificial sequence
<220> FEATURE:

<223> OTHER INFORMATION: Synthetic oligonucleotide

<400> SEQUENCE: 8
cggcgtcgcc gccg                                                         14

<210> SEQ ID NO 9
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 9
cggcgtcgtg ccg                                                          13

<210> SEQ ID NO 10
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 10
cgtcgacggg acggg                                                        15

<210> SEQ ID NO 11
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 11
cgtcgacgtg acggg                                                        15

<210> SEQ ID NO 12
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 12
gagagttggg ctctc                                                        15

<210> SEQ ID NO 13
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 13
ggcgcgctgc cg                                                           12

<210> SEQ ID NO 14
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 14
gtcgaggagg t                                                            11

<210> SEQ ID NO 15

```
<211> LENGTH: 12
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6)..(7)
<223> OTHER INFORMATION: abasic nucleotide
<220> FEATURE:
<221> NAME/KEY: misc_feature
<222> LOCATION: (6)..(7)
<223> OTHER INFORMATION: n is a, c, g, or t

<400> SEQUENCE: 15
taatanntat ta                                                          12

<210> SEQ ID NO 16
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 16
taatatccat ta                                                          12

<210> SEQ ID NO 17
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 17
taatatttat ta                                                          12

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
tccaggactt ctctcaggtt                                                  20

<210> SEQ ID NO 19
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 19
tcgacgtcga                                                             10

<210> SEQ ID NO 20
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 20
tcgacgtcga ccgttttgtg g                                                21

<210> SEQ ID NO 21
```

```
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 21
tcgacgtcga cgggacggg                                                    19

<210> SEQ ID NO 22
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 22
tcgacgtcga cgtgacggg                                                    19

<210> SEQ ID NO 23
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 23
tcgacgtcga gagttgggct ctc                                               23

<210> SEQ ID NO 24
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 24
tcgacgtcga gcgaagct                                                     18

<210> SEQ ID NO 25
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 25
tcgacgtcga ggaggt                                                       16

<210> SEQ ID NO 26
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 26
tcgcgacgtt                                                              10

<210> SEQ ID NO 27
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 27
```

```
tcgcgacgtt cggcgcgctg ccg                                          23

<210> SEQ ID NO 28
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 28
tcgcgacgtt cggcgcgtcg ccg                                          23

<210> SEQ ID NO 29
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 29
tcgcgacgtt cggcggctcg ccg                                          23

<210> SEQ ID NO 30
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 30
tcgcgtcgtt cggcgcgctg ccg                                          23

<210> SEQ ID NO 31
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 31
tcgcgtcgtt cggcgcgtcg ccg                                          23

<210> SEQ ID NO 32
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 32
tcgcgtcgtt cggcggctcg ccg                                          23

<210> SEQ ID NO 33
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 33
tcggcgccgt gccgtcgtcg ttt                                          23

<210> SEQ ID NO 34
<211> LENGTH: 10
<212> TYPE: DNA
<213> ORGANISM: Artificial sequence
<220> FEATURE:
```

```
<223> OTHER INFORMATION: Synthetic oligonucleotide

<400> SEQUENCE: 34
tcgtcgacga                                                                 10

<210> SEQ ID NO 35
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 35
tcgtcgcccg gcgacgccgt gccg                                                 24

<210> SEQ ID NO 36
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 36
tcgtcgcttt gcgacgccgt gccg                                                 24

<210> SEQ ID NO 37
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (9)..(10)
<223> OTHER INFORMATION: abasic nucleotide
<220> FEATURE:
<221> NAME/KEY: misc_feature
<222> LOCATION: (9)..(10)
<223> OTHER INFORMATION: n is a, c, g, or t

<400> SEQUENCE: 37
tcgtcgttnn acggcgccgt gccg                                                 24

<210> SEQ ID NO 38
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (9)..(10)
<223> OTHER INFORMATION: abasic nucleotide
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (17)..(19)
<223> OTHER INFORMATION: abasic nucleotide
<220> FEATURE:
<221> NAME/KEY: misc_feature
<222> LOCATION: (17)..(19)
<223> OTHER INFORMATION: n is a, c, g, or t

<400> SEQUENCE: 38
tcgtcgttnn acggcgnnnt gccg                                                 24

<210> SEQ ID NO 39
```

```
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (9)..(10)
<223> OTHER INFORMATION: abasic nucleotide
<220> FEATURE:
<221> NAME/KEY: misc_feature
<222> LOCATION: (9)..(10)
<223> OTHER INFORMATION: n is a, c, g, or t

<400> SEQUENCE: 39
tcgtcgttnn cggcgcggcg ccg                                           23

<210> SEQ ID NO 40
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 40
tcgtcgtttt                                                          10

<210> SEQ ID NO 41
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 41
tcgtcgtttt a                                                        11

<210> SEQ ID NO 42
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 42
tcgtcgtttt acgacgccgt gccg                                          24

<210> SEQ ID NO 43
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 43
tcgtcgtttt acggcgccgt gccg                                          24

<210> SEQ ID NO 44
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 44
tcgtcgtttt acggcgccgt tgccg                                         25

<210> SEQ ID NO 45
```

```
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (17)..(19)
<223> OTHER INFORMATION: abasic nucleotide
<220> FEATURE:
<221> NAME/KEY: misc_feature
<222> LOCATION: (17)..(19)
<223> OTHER INFORMATION: n is a, c, g, or t

<400> SEQUENCE: 45
tcgtcgtttt acggcgnnnt gccg                                            24

<210> SEQ ID NO 46
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 46
tcgtcgtttt acggcgtcgc g                                               21

<210> SEQ ID NO 47
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 47
tcgtcgtttt acggcgtcgc gccg                                            24

<210> SEQ ID NO 48
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 48
tcgtcgtttt acggcgtcgt gccg                                            24

<210> SEQ ID NO 49
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 49
tcgtcgtttt acggcgtttt gccg                                            24

<210> SEQ ID NO 50
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 50
tcgtcgtttt caatatttat tg                                              22

<210> SEQ ID NO 51
```

```
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 51
tcgtcgtttt cggcgcgcgc cg                                              22

<210> SEQ ID NO 52
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (16)..(17)
<223> OTHER INFORMATION: abasic nucleotide
<220> FEATURE:
<221> NAME/KEY: misc_feature
<222> LOCATION: (16)..(17)
<223> OTHER INFORMATION: n is a, c, g, or t

<400> SEQUENCE: 52
tcgtcgtttt cggcgnncgc cg                                              22

<210> SEQ ID NO 53
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 53
tcgtcgtttt cggcggccgc cg                                              22

<210> SEQ ID NO 54
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (17)..(18)
<223> OTHER INFORMATION: abasic nucleotide
<220> FEATURE:
<221> NAME/KEY: misc_feature
<222> LOCATION: (17)..(18)
<223> OTHER INFORMATION: n is a, c, g, or t

<400> SEQUENCE: 54
tcgtcgtttt cggcggnncc gccg                                            24

<210> SEQ ID NO 55
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 55
tcgtcgtttt cggcgtcgcc gccg                                            24

<210> SEQ ID NO 56
<211> LENGTH: 24
<212> TYPE: DNA
<213> ORGANISM: Artificial sequence
<220> FEATURE:
```

<223> OTHER INFORMATION: Synthetic oligonucleotide

<400> SEQUENCE: 56
tcgtcgtttt gtcgttttgt cgtt                24

<210> SEQ ID NO 57
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (16)..(17)
<223> OTHER INFORMATION: abasic nucleotide
<220> FEATURE:
<221> NAME/KEY: misc_feature
<222> LOCATION: (16)..(17)
<223> OTHER INFORMATION: n is a, c, g, or t

<400> SEQUENCE: 57
tcgtcgtttt taatanntat ta                22

<210> SEQ ID NO 58
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 58
tcgtcgtttt taatatccat ta                22

<210> SEQ ID NO 59
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 59
tcgtcgtttt taatatttat ta                22

<210> SEQ ID NO 60
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 60
tgctgctttt gtgcttttgt gctt                24

<210> SEQ ID NO 61
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 61
tcgacgtcga cgtgacg                17

<210> SEQ ID NO 62
<211> LENGTH: 19
<212> TYPE: DNA
<213> ORGANISM: Artificial sequence
<220> FEATURE:

<223> OTHER INFORMATION: Synthetic oligonucleotide

<400> SEQUENCE: 62
tcgacgtcga cgtgacgtg                                                  19

<210> SEQ ID NO 63
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 63
tcgacgtcga cgtgacgtt                                                  19

<210> SEQ ID NO 64
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 64
tcgtcgacga tcggcgccgt gccg                                            24

<210> SEQ ID NO 65
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 65
tcgtcgacgt tcggcgccgt gccg                                            24

<210> SEQ ID NO 66
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 66
tcgtcgtacg gcgccgtgcc g                                               21

<210> SEQ ID NO 67
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 67
tcgtcgttac ggcgccgtgc cg                                              22

<210> SEQ ID NO 68
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 68
tcgtcgttta cggcgccgtg ccgt                                            24

<210> SEQ ID NO 69

```
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 69
tcgcgtcgtt                                                          10
```